United States Patent
Cazaux et al.

(10) Patent No.: US 9,790,556 B2
(45) Date of Patent: Oct. 17, 2017

(54) SIGNATURE FOR THE DIAGNOSIS OF LUNG CANCER AGGRESSIVENESS AND GENETIC INSTABILITY

(71) Applicant: CENTRE NATIONAL DE LA RECHERCHE SCIENTIFIQUE (CNRS), Paris (FR)

(72) Inventors: Christophe Cazaux, Plaisance du Touch (FR); Jean-Sébastien Hoffmann, Toulouse (FR)

(73) Assignee: CENTRE NATIONAL DE LA RECHERCHE SCIENTIFIQUE (CNRS), Paris (FR)

(*) Notice: Subject to any disclaimer, the term of this patent is extended or adjusted under 35 U.S.C. 154(b) by 11 days.

(21) Appl. No.: 14/370,695

(22) PCT Filed: Jan. 7, 2013

(86) PCT No.: PCT/EP2013/050153
§ 371 (c)(1),
(2) Date: Jul. 3, 2014

(87) PCT Pub. No.: WO2013/102680
PCT Pub. Date: Jul. 11, 2013

(65) Prior Publication Data
US 2014/0378338 A1 Dec. 25, 2014

(30) Foreign Application Priority Data
Jan. 5, 2012 (EP) .................................... 12305012

(51) Int. Cl.
*C12Q 1/68* (2006.01)

(52) U.S. Cl.
CPC ...... *C12Q 1/6886* (2013.01); *C12Q 2600/118* (2013.01); *C12Q 2600/158* (2013.01)

(58) Field of Classification Search
None
See application file for complete search history.

(56) References Cited

FOREIGN PATENT DOCUMENTS

| EP | 2 322 658 A1 | 5/2011 |
|---|---|---|
| KR | 10-2008-0112764 A | 12/2008 |
| WO | WO 2004/080976 A1 | 9/2004 |
| WO | WO 2005/053662 A1 | 6/2005 |
| WO | WO 2007/001684 A2 | 1/2007 |
| WO | WO 2008/082856 A1 | 7/2008 |
| WO | WO 2009/046205 A1 | 4/2009 |
| WO | WO 2010/064702 A1 | 6/2010 |
| WO | WO 2011/058143 A1 | 5/2011 |
| WO | WO 2011/160118 A2 | 12/2011 |
| WO | WO 2012/006447 A2 | 1/2012 |

OTHER PUBLICATIONS

WO2010/064702 A1 translation; obtained Sep. 30, 2015; https://patentscope.wipo.int/search/en/detail.jsf?docId=WO2010064702&recNum=2&maxRec=2&offi.*

Rom et al.; Molecular and Genetic Aspects of Lung Cancer; American Journal of Respiratory and Critical Care Medicine; vol. 161, No. 4, pp. 1355-1367, Apr. 2000.*
Nguewa et al.; Identification of Importin 8 (IPO8) as the most accurate reference gene for the clinicopathological analysis of lung specimens; BMC Molecular Biology 2008, 9:103, pp. 1-11.*
Andriani et al., "Inactivation of Both FHIT and p53 Cooperate in Deregulating Proliferation-Related Pathways in Lung Cancer", Journal of Thoracic Oncology, vol. 7, Issue 4, Apr. 2012, pp. 631-642, Abstract only provided.
Arentson et al., "Oncogenic potential of the DNA replication licensing protein CDT1", Oncogene, vol. 21, 2002, pp. 1150-1158.
Bartkova et al., "Oncogene-induced senescence is part of the tumorigenesis barrier imposed by DNA damage checkpoints", Nature, vol. 444, Nov. 30, 2006, pp. 633-637.
Bertwistle et al., "Functions of the BRCA1 and BRCA2 genes", Curr. Opin. Genet. Dev., vol. 8, 1998, pp. 14-20.
Capp et al., "Involvement of DNA polymerase μ in the repair of a specific subset of DNA double-strand breaks in mammalian cells", Nucleic Acids Research, vol. 35, No. 11, 2007 (published online May 5, 2007), pp. 3551-3560.
Courbet et al., "Replication fork movement sets chromatin loop size and origin choice in mammalian cells", Nature, vol. 455, Sep. 25, 2008, pp. 557-560.
Eisenberg et al., "Human housekeeping genes are compact", Trends in Genetics, vol. 19, No. 7, Jul. 2003, pp. 362-365.
Esposito et al., "Prognostic value of p53 in non-small cell lung cancer: relationship with proliferating cell nuclear antigen and ciagarette smoking", Hum Pathol, vol. 28, No. 2, Feb. 1997, pp. 233-237.
Extended European Search Report for European Application No. 12305012.2 dated Jul. 10, 2012.
Fong et al., "Tumor Progression and Loss of Heterozygosity at 5q and 18q in Non-Small Cell Lung Cancer", Cancer Research, vol. 55, Jan. 15, 1995, pp. 220-223.
Glover et al., "Mechanisms of common fragile site instability", Human Molecular Genetics, vol. 14, Review Issue 2, 2005, pp. R197-R205.
Hayakawa et al., "MRG15 binds directly to PALB2 and stimulates homology-directed repair of chromosomal breaks", Journal of Cell Science, vol. 123, 2010, pp. 1124-1130 (14 pages).

(Continued)

*Primary Examiner* — Antonio Galisteo Gonzalez
(74) *Attorney, Agent, or Firm* — Birch, Stewart, Kolasch & Birch, LLP

(57) ABSTRACT

The present invention relates to a method for diagnosing aggressiveness of a lung cancer in a patient from a lung cancer sample of the patient, comprising: a) detecting in vitro an expression profile of the DNA replication stress signature, the signature comprising the CDC6, CLASPIN, PLK1, and POLQ genes, as well as, optionally, RAD51; b) comparing the the expression profile to a reference expression profile, and d) diagnosing cancer aggressiveness from the comparison. Dedicated microarrays and kits are also described, as well as a method of selecting or adapting a suitable treatment.

Figure 1A:
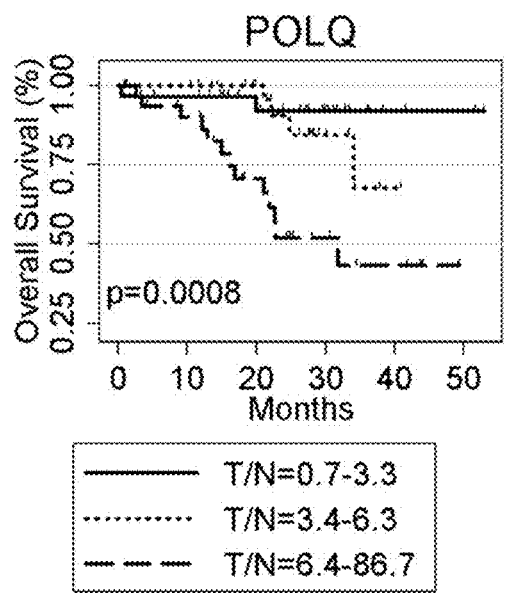
Figure 1B:
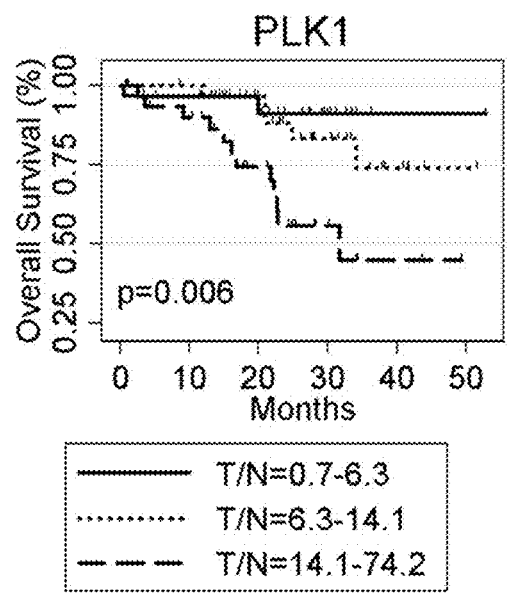
Figure 1C:
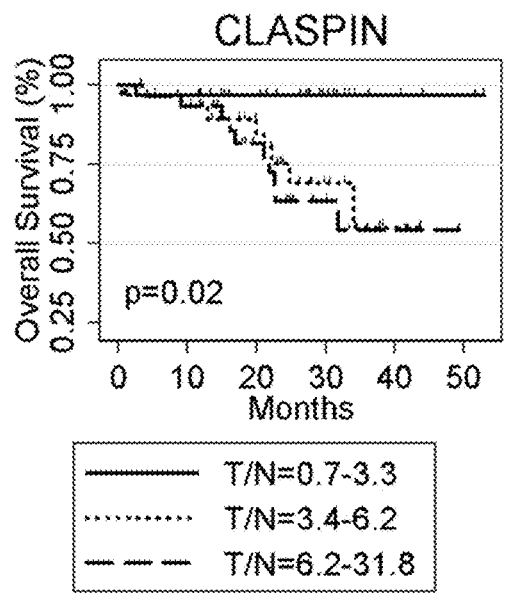
Figure 1D:
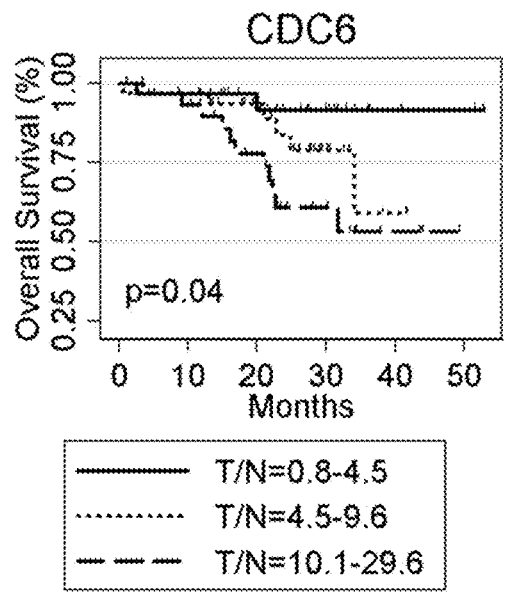
Figure 1E:
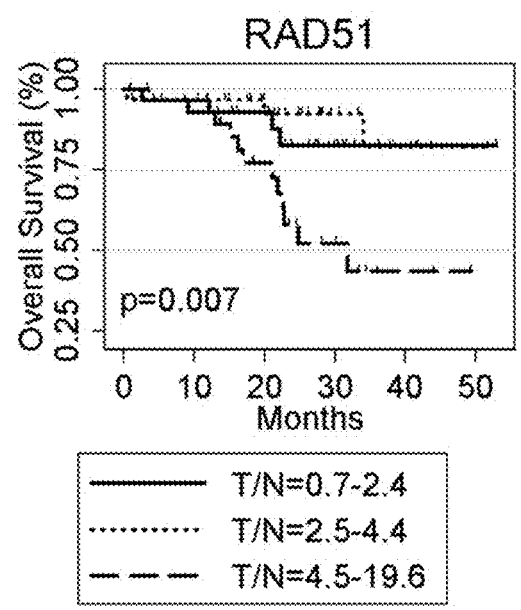

14 Claims, 4 Drawing Sheets
(1 of 4 Drawing Sheet(s) Filed in Color)

(56) References Cited

OTHER PUBLICATIONS

He et al., "CBP/p300 and SIRT1 Are Involved in Transcriptional Regulation of S-Phase Specific Histone Genes", PLOS one, vol. 6, Issue 7, Jul. 2011, 14 pages.
Hoffmann et al., "Aberrant expression of alternative DNA polymerases: A source of mutator phenotype as well as replicative stress in cancer", Seminars in Cancer Biology, vol. 20, 2010, pp. 312-319.
Honeycutt et al., "Deregulated minichromosomal maintenance protein MCM7 contributes to oncogene driven tumorigenesis", Oncogene, vol. 25, 2006 (published online Mar. 6, 2006), pp. 4027-4032.
Inglis, "DNA Replication and Human Disease", Cold Spring Harbor Laboratory Press, 2006, pp. i-xvii.
International Search Report for International Application No. PCT/EP2013/050153 (Forms PCT/ISA/220 and PCT/ISA/210) dated Mar. 19, 2013.
Kahli et al., "HMGA proteins modify the replication program during senescence", Biology, 2011, 2 pages, with an English translation.
Kawamura et al., "DNA Polymerase θ is Preferentially Expressed in Lymphoid Tissues and Upregulated in Human Cancers", Int. J. Cancer., vol. 109, 2004, pp. 9-16.
Kim et al., "Time-course analysis of DNA damage response-related genes after in vitro radiation in H460 and H1229 lung cancer cell lines", Experimental and Molecular Medicine, vol. 43, No. 7, Jul. 2011 (available online Jun. 2, 2011), pp. 419-426.
Kunkel, "Considering the cancer consequences of altered DNA polymerase function", Cancer Cell, vol. 3, Feb. 2003, pp. 105-110.
Lemée et al., "DNA polymerase θ up-regulation is associated with poor survival in breast cancer, perturbs DNA replication, and promotes genetic instability", PNAS, vol. 107, No. 30, Jul. 27, 2010, pp. 13390-13395.
Lin et al., "SHPRH and HLTF Act in a Damage-Specific Manner to Coordinate Different Forms of Postreplication Repair and Prevent Mutagenesis", Molecular Cell, vol. 42, Apr. 22, 2011, pp. 237-249.
Lutzmann et al., "MCM9 Binds Cdt1 and Is Required for the Assembly of Prereplication Complexes", Molecular Cell, vol. 31, Jul. 25, 2008, pp. 190-200.
MacAlpine et al., "*Drosophila* ORC localizes to open chromatin and marks sites of cohesin complex loading", Genome Research, vol. 20, (published online Dec. 7, 2009), 2010, pp. 201-211.
Maiorano et al.,"MCM8 Is an MCM2-7-Related Protein that Functions as a DNA Helicase during Replication Elongation and Not Initiation", Cell, vol. 120, Feb. 11, 2005, pp. 315-328.
Mao et al., "SIRT6 Promotes DNA Repair Under Stress by Activating PARP1", Science, vol. 332, Jun. 17, 2011, pp. 1443-1446.
Marra et al., "Hereditary Nonpolyposis Colorectal Cancer: the Syndrome, the Genes, and Historical Perspectives", Journal of the National Cancer Institute, vol. 87, No. 15, Aug. 2, 1995, pp. 1114-1125.
Masutani et al., "The XPV (xeroderma pigmentosum variant) gene encodes human DNA polymerase", Nature, vol. 399, Jun. 17, 1999, pp. 700-701.
Matakidou et al., "Genetic variation in the DNA repair genes is predictive of outcome in lung cancer", Human Molecular Genetics, vol. 16, No. 19, 2007, pp. 2333-2340.
Minard et al., "SWI/SNF and Asf1 Independently Promote Derepression of the DNA Damage Response Genes under Conditions of Replication Stress", PLOS One, vol. 6, No. 6, Jun. 27, 2011, 10 pages.
Mitchell et al., "Divide and conquer: nucleotide excision repair battles cancer and ageing", Current Opinion in Cell Biology, vol. 15, 2003, pp. 232-240.
Pillaire et al.,"A 'DNA replication' signature of progression and negative outcome in colorectal cancer", Oncogene, vol. 29, 2010 (published online Nov. 9, 2009), pp. 876-887.
Qiao et al., "High-level expression of Rad51 is an independent prognostic marker of survival in non-small-cell lung cancer patients", British Journal of Cancer, vol. 93, 2005 (published online Jun. 14, 2005), pp. 137-143.
Rey et al., "Human DNA Polymerase η Is Required for Common Fragile Site Stability during Unperturbed DNA Replication", Molecular and Cellular Biology, vol. 29, No. 12, Jun. 2009, pp. 3344-3354.
Sancar, "Mechanisms of DNA Excision Repair", Science, vol. 266, No. 5193, Dec. 23, 1994, pp. 1954-1956.
Seki et al., "High-efficiency bypass of DNA damage by human DNA polymerase Q", The EMBO Journal, vol. 23, 2004 (published online Oct. 21, 2004), pp. 4484-4494.
Sobol et al., "Requirement of mammalian DNA polymerase-β in base-excision repair", Nature, vol. 379, Jan. 11, 1996, pp. 183-186.
Thomae et al., "Interaction between HMGA1a and the origin recognition complex creates site-specific replication origins", PNAS, Feb. 5, 2008, vol. 105, No. 5, pp. 1692-1697.
Venkatesan et al., "Mutation at the Polymerase Active Site of Mouse DNA Polymerase Increases Genomic Instability and Accelerates Tumorigenesis", Molecular and Cellular Biology, vol. 27, No. 21, Nov. 2007, pp. 7669-7682.
Wang et al., "Overexpression of polo-like kinase 1 and its clinical significance in human non-small cell lung cancer", The International Journal of Biochemistry & Cell Biology, vol. 44, 2012 (Available Online Nov. 3, 2011), pp. 200-210.
Yim et al., "Regulation of the final stage of mitosis by components of the pre-replicative complex and a polo kinase", Cell Cycle, vol. 10, Issue 9, May 1, 2011, pp. 1374-1377.
Zheng et al., "DNA Synthesis and Repair Genes RRM1 and ERCC1 in Lung Cancer", The New England Journal of Medicine, vol. 356, No. 8, Feb. 22, 2007, pp. 800-808.

* cited by examiner

| Pearson coefficient | CLASPIN | CDC6 | PLK1 | RAD51 | POLQ |
|---|---|---|---|---|---|
| CLASPIN | 1.00 | | | | |
| CDC6 | 0.76 | 1.00 | | | |
| PLK1 | 0.81 | 0.86 | 1.00 | | |
| RAD51 | 0.74 | 0.80 | 0.80 | 1.00 | |
| POLQ | 0.77 | 0.80 | 0.80 | 0.75 | 1.00 |

SIGNATURE FOR THE DIAGNOSIS OF LUNG CANCER AGGRESSIVENESS AND GENETIC INSTABILITY

This application is a national phase application of PCT International Application No. PCT/EP2013/050153 filed on Jan. 7, 2013, which claims the benefit of Patent Application No. 12305012.2, filed in the European Patent Office on Jan. 5, 2012. The entire contents of all of the above applications are hereby incorporated by reference into the present application.

FIELD OF THE INVENTION

The present invention is in the field of lung cancer management, including diagnosis of aggressiveness of said cancer, and selection of an appropriate treatment. The invention is based on the finding that overexpression of a signature comprising the CDC6, CLASPIN, PLK1, and POLQ genes, as well as, optionally, the RAD51 gene, is highly related to aggressiveness of a tumor, and thus to survival of the patient.

BACKGROUND ART

Cancer is a multi-faceted disease in which a group of cells display uncontrolled growth, invasion that intrudes upon and destroys adjacent tissues, and sometimes metastasis, or spreading to other locations in the body via lymph or blood. These three malignant properties of cancers differentiate them from benign tumors, which do not invade or metastasize.

Lung cancer—predominantly non-small lung cancer (NSCLC)—is the first cause of cancer deaths worldwide, resulting in about 1 million deaths each year. Its incidence increases especially for non-smoking women. Despite advances in prevention, screening, resection methodology and chemotherapy strategies, only about 15% of patients survive more than 5 years.

The selection of an appropriate treatment is crucial for the patient. It is essential to know when to use immediately a heavy and aggressive treatment protocol in order to prevent extension of an aggressive cancer. In contrast, performing a heavy and aggressive treatment when it is not necessitated by the tumor carried by the patient is also disadvantageous for the patient. Indeed, heavy and aggressive treatments always lead to adverse toxicities that may significantly affect the patient's quality of life. In addition, such heavy and aggressive treatments are usually very costly, and should thus be performed only when it is necessary.

Currently, treatment selection for solid tumors is based on tumor staging, which is usually performed using the Tumor/Node/Metastasis (TNM) test from the American Joint Committee on Cancer (AJCC). The TNM system assigns a number based on three categories. "T" denotes the tumor size, "N" the degree of lymphatic node involvement, and "M" the degree of metastasis. The broader stage of a cancer is usually quoted as a number I, II, III, IV derived from the TNM value grouped by prognosis; a higher number indicates a more advanced cancer and likely a worse outcome.

It is commonly acknowledged that, while this test and staging system provides some valuable information concerning the stage at which solid cancer has been diagnosed in the patient, it is imprecise and insufficient. In particular, it fails to identify the earliest stages of tumor progression. In addition, the TNM test does not give information on the tumor aggressiveness and its usefulness for prognosis is thus limited. According to clinicians and pathologists, the current clinical staging "Tumor Node Metastasis" (TNM) system is thus not sufficient for predicting the outcome of patients.

There is a real need for better prognosis tests of cancer, not only to improve patient global survival, but also to improve their quality of life and to keep aggressive and costly chemotherapies for patients who will really benefit from them. In particular, there is a need for novel robust prognosis markers which can be used reliably for the prognosis of lung cancer.

In an attempt to identify predictors of patient prognosis and response to therapy, many studies profiling gene expression in lung cancer have been completed or are in progress. So far, these genetic tests add modest prognostic information to standard prediction methods. Indeed these multi-gene signatures were mostly obtained from unbiased micro-array based screenings of thousands of genes and therefore mostly include "endpoint" selected cell proliferation-related genes i.e. genes that drive at the latest stages of tumorigenesis either cell cycle progression or tumor differentiation. However these two latter features were already estimated by the standard clinico-pathological markers e.g. histological grade, mitotic count, Ki67 index, etc., which also capture the proliferation status.

Since the conventional clinical staging classification is not sufficient to predict the survival of patients who suffer from lung cancer, additional prognostic factors are needed to better forecast their outcome. The present inventors have shown that a DNA replication stress signature is a predictor of the cancer survival.

DESCRIPTION OF THE INVENTION

The present inventors have identified a DNA replication stress signature, and have shown that this signature is associated with a poor prognosis in lung cancer. More specifically, a group of genes comprising CDC6, CLASPIN, PLK1, and POLQ are overexpressed in lung cancer and this overexpression gives information about the patient prognosis. For example, these four genes were found to be overexpressed in most of 93 lung cancers. This overexpression was associated to the patient survival, whatever the survival term examined (overall survival, relapse-free survival, disease-free survival). Remarkably, the statistical link between this 4-gene signature and patient survival is independent of the tumor stage and of the treatment, and this correlation was even better when RAD51 was included within the signature.

The present invention thus provides a DNA replication stress gene signature for diagnosing the aggressiveness of a lung cancer in a patient, the said signature comprising the CDC6, CLASPIN, PLK1, and POLQ genes. Advantageously, the said signature further comprises the RAD51 gene. In a preferred embodiment, the said signature consists of the CDC6, CLASPIN, PLK1, and POLQ genes. In a further preferred embodiment, the said signature consists of the CDC6, CLASPIN, PLK1, POLQ, and RAD51 genes.

In another aspect, the present invention also relates to a method for diagnosing the aggressiveness of a lung cancer in a patient. According to the method of the invention, elevated expression levels of the genes of the DNA replication stress gene signature indicate aggressiveness of said cancer.

Therefore, the present invention provides a method for diagnosing aggressiveness of a lung cancer in a patient, comprising the steps of:
a) detecting from a biological sample of said patient an expression profile of the DNA replication stress gene signature, said signature comprising the CDC6, CLASPIN, PLK1, and POLQ genes;

b) comparing the expression profile of step a) with at least one reference expression profile, and c) diagnosing aggressiveness or non-aggressiveness of the lung cancer from the said comparison.

In a preferred embodiment of the methods of the invention, the signature further comprises the RAD51 gene. In another preferred embodiment of the methods of the invention, the signature consists of the CDC6, CLASPIN, PLK1, and POLQ genes. In an even further preferred embodiment, the said signature consists of the CDC6, CLASPIN, PLK1, POLQ, and RAD51 genes.

As used herein, the terms "cancer" and "cancerous" refer to or describe the physiological condition in mammals that is typically characterized by unregulated cell growth. The terms "cancer" and "cancerous" as used herein are meant to encompass all stages of the disease. Thus, a "cancer" as used herein may include both benign and malignant tumors.

A "lung cancer" according to the present invention is a non-small-cell lung cancer or small cell lung cancer. Preferably, the lung cancer of the invention is a non-small-cell lung cancer (NSCLC). More preferably, the NSCLC of the invention is selected among the group comprising squamous cell carcinoma, large cell carcinoma, adenocarcinoma, pleomorphic carcinoma, carcinoid tumor and unclassified lung carcinoma. Most preferably, the NSCLC is a squamous cell carcinoma, a large cell carcinoma, or an adenocarcinoma.

As used herein, the term "POLQ" refers to the human gene encoding the DNA polymerase theta (Entrez Gene ID number: 10721; mRNA sequence reference: NM_199420.3; protein sequence reference: NP_955452.3); the term "PLK1" to the human gene encoding the polo-like kinase 1 (mRNA sequence reference: NM_005030; protein sequence reference: NP_005021.2); the term "CLASPIN" to the human gene encoding the regulator of Chk1, said gene being also designated CLSPN (mRNA sequence reference: NM_001190481.1; protein sequence reference: NP_001177410.1); the term "CDC6" to the human gene encoding a protein required for replication initiation (mRNA sequence reference: NM_001254.3; protein sequence reference: NP_001245.1); and the term "RAD51" to the human gene encoding a protein which assists in repair of DNA double strand breaks (mRNA sequence reference: NM_002875; protein sequence reference: NP_002866).

In addition, the invention encompasses all the isoforms of the said genes. Isoform, as used herein, refers to all the different forms of the said genes and may be produced by mutations, or may arise from the same gene by alternative splicing. A large number of isoforms are caused by single nucleotide polymorphisms or SNPs, small genetic differences between alleles of the same gene. These occur at specific individual nucleotide positions within a gene. Also included within this definition is the situation where different versions of messenger RNA are created from the same gene by employing different promoters, which causes transcription to skip certain exons. Thus, it is understood that the methods of the invention are not restricted to the said CDC6, CLASPIN, PLK1, POLQ, and RAD51 per se, but also encompass one or several of the isoforms of one or several of the said genes. According to methods of the invention, the level of the expression of the said gene and/or one or several of its isoforms is measured, and expression profiles determined.

According to the present invention, "aggressiveness" of a lung cancer is intended to mean the propensity of said lung cancer to invade the neighboring tissues and to generate metastases and the rapidity with which said invasions may appear.

According to the method of the invention, a cancer is aggressive when the expression profile of step a) is different from the at least one reference expression profile of step b). For example, if the said reference profile of step b) is obtained from a healthy, non-cancerous sample, a cancer is aggressive if the said expression profile of step a) is increased by comparison to the said reference expression profile of step b). In other words, if, for example, the said reference profile of step b) is obtained from a healthy, non-cancerous sample, a cancer is aggressive if the genes of the signature of the invention are more expressed in the sample from the patient tested than in the healthy, non-cancerous, reference sample.

Aggressiveness of the lung cancer is obviously correlated to survival, and the above method may be used for prognosing survival of the patient, in which case diagnosing of aggressiveness results in a bad survival prognosis and diagnosis of the absence of aggressiveness results in a good survival prognosis.

Thus the present invention also relates to a method for evaluating survival of a patient suffering from lung cancer, comprising the steps of:

a) detecting from a biological sample of said patient an expression profile of the DNA replication stress gene signature, said signature comprising the CDC6, CLASPIN, PLK1, and POLQ genes;

b) comparing the expression profile of step a) with at least one reference expression profile, and c) evaluating the survival prognosis of the said patient from the said comparison.

In a preferred embodiment of the methods of the invention, the signature further comprises the RAD51 gene. In another preferred embodiment of the methods of the invention, the signature consists of the CDC6, CLASPIN, PLK1, and POLQ genes. In an even further preferred embodiment, the said signature consists of the CDC6, CLASPIN, PLK1, POLQ, and RAD51 genes.

By "expression profile" is meant the expression levels of the genes of the DNA replication stress signature, including CDC6, CLASPIN, PLK1, and POLQ, as well as, optionally, RAD51. In a preferred embodiment, the expression profile consists of the CDC6, CLASPIN, PLK1, and POLQ genes, since the expression patterns of these genes have been demonstrated to be particularly relevant for assessing the aggressiveness of a lung cancer of the said lung cancer. In a most preferred embodiment, the expression profile for diagnosing if the said lung cancer is aggressive further includes the RAD51 gene.

The expression profile according to the invention may be determined by any technology known by a man skilled in the art. Preferably, the determination of the expression profile according to the invention involves measuring the expression level of each of the gene of the DNA replication stress signature. In particular, each gene expression level may be measured at the genomic and/or nucleic and/or protein level. In a preferred embodiment, the expression profile is determined by measuring the amount of nucleic acid transcripts of each gene. In another embodiment, the expression profile is determined by measuring the amount of protein produced by each of the genes.

The diagnosis of the aggressiveness of a lung cancer is carried out thanks to the comparison of the obtained expression profile with at least one reference expression profile in step (b).

A "reference expression profile" is a predetermined expression profile, obtained from a reference sample. Preferably, the said reference expression profile is obtained by measuring the expression level of each of the genes of the said signature in the said reference sample. A "reference sample" according to the invention is a biological sample associated with a specific outcome class. In one embodiment, the reference expression profile may be obtained from a reference sample associated with a poor survival outcome. For example, such a reference sample may be made of cancerous tissue at a specific, well-identified stage. In another embodiment, the reference expression profile may be obtained from a reference sample associated with a good survival outcome. An example of such a biological sample associated with a good survival outcome is a biological sample made of healthy, non-cancerous lung tissue. Said healthy, non-cancerous lung tissue may be composed of only one subject's healthy lung tissue, or may be a pooled sample made of several subject's healthy lung tissue. When the sample is made from only one subject's healthy lung tissue, said subject may be either the tested patient or another subject. Advantageously, the said biological sample is obtained from the lung-cancer patient to be diagnosed. Indeed, as mentioned above, even in a cancerous patient, lung tissue still comprises non tumor healthy tissue. In particular, when the lung cancer sample is taken from a surgical resection therapy, adjacent, non-tumor, healthy lung tissue of the patient to be diagnosed is generally available and may be used as healthy control sample. In that case, observed variations in gene expression between the tested cancerous biological sample and the reference healthy sample may be ascribed principally to the lung cancer, and not to inter-personal and/or inter-tissue variations in gene expression.

The above methods are performed using a cancer sample of the patient to be tested. In some cases, the methods according to the invention may further comprise a preliminary step of taking a cancer sample from the patient. By a "cancer sample" or "lung cancer sample", it is referred to a lung tumor sample. Even in a cancerous patient, the lung tissue which is the site of the tumor still comprises non tumor healthy tissue. The "cancer sample" should thus be limited to tumor tissue taken from the patient. Said "cancer sample" may be a biopsy lung sample or a lung sample taken from a surgical resection therapy of the patient.

In addition, the methods according to the invention may comprise another preliminary step, between the taking of the sample from the patient and steps a) as defined above, corresponding to the transformation of the cancer sample (and optionally of the healthy tissue sample) into a mRNA (or corresponding cDNA) sample or into a protein sample, which is then ready to use for in vitro measuring of genes expression levels in step a). Preparation or extraction of mRNA (as well as retrotranscription into cDNA) or proteins from a tissue sample is only routine procedure well known to those skilled in the art.

Once a ready-to-use cancer mRNA (or corresponding cDNA) or protein sample is available, the measure of the expression levels of the signature genes, including or consisting of CDC6, CLASPIN, PLK1, and POLQ, and optionally RAD51, may be performed, depending on the type of transformation and the available ready-to-use sample, either at the mRNA (i.e. based on the mRNA content of the sample) or at the protein level (i.e. based on the protein content of the sample). In some embodiments, the expression levels of some of the genes may be measured at the mRNA level, while the expression levels of other genes are measured at the protein level. In this case, part of the cancer sample taken from the patient has been transformed into an mRNA (or corresponding cDNA) sample and another part has been transformed into a protein sample. In other embodiments, the expression levels of all tested genes are measured either at the mRNA or at the protein level.

Methods for quantifying mRNA are well known in the art. Indeed, when expression levels are measured at the mRNA level, it may be notably performed using well known technologies such as quantitative PCR or nucleic acid microarray technologies (including cDNA and oligonucleotide microarrays). These technologies are now used routinely by those skilled in the art and thus need not to be detailed here. Examples of embodiments using quantitative PCR are described in the experimental section. Alternatively, any known or future technology permitting to assess genes expression levels based on mRNA contents may be used. For instance, tissue microarrays coupled to fluorescent in situ hybridization may be used. Tissue microarrays (also known as TMAs) consist of paraffin blocks in which up to 1000 separate tissue cores are assembled in array fashion to allow multiplex histological analysis. In the tissue microarray technique, a hollow needle is used to remove tissue cores as small as 0.6 mm in diameter from regions of interest in paraffin-embedded tissues such as clinical biopsies or tumor samples. These tissue cores are then inserted in a recipient paraffin block in a precisely spaced, array pattern. Sections from this block are cut using a microtome, mounted on a microscope slide and then analyzed by any method of standard histological analysis. Each microarray block can be cut into 100-500 sections, which can be subjected to independent tests. Tests commonly employed in tissue microarray include immunohistochemistry, and fluorescent in situ hybridization. For analysis at the mRNA level, tissue microarray technology may be coupled to fluorescent in situ hybridization.

When expression levels are measured at the protein level, it may be notably performed using specific antibodies, in particular using well known technologies such as western blot, ELISA or ELISPOT, antibodies microarrays, or tissue microarrays coupled to immunohistochemistry. Other suitable techniques include FRET or BRET, single cell microscopic or histochemistry methods using single or multiple excitation wavelength and applying any of the adapted optical methods, such as electrochemical methods (voltammetry and amperometry techniques), atomic force microscopy, and radio frequency methods, e.g. multipolar resonance spectroscopy, confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry), cell ELISA, flow cytometry, radioisotopic, magnetic resonance imaging, analysis by mass spectrometry (MS), tandem mass spectrometry (MS-MS), MS 3; matrix-assisted laser desorption/ionization time-of-flight (MALDI-TOF) mass spectrometry; polyacrylamide gel electrophoresis (SDS-PAGE); H PLC-Mass Spectroscopy; Liquid Chromatography/Mass Spectrometry/Mass Spectrometry (LC-MS/MS)). All these techniques are well known in the art and need not be further detailed here.

The comparison of a tested patient expression profile with a reference expression profile allows the determination of whether the said expression profiles are similar or different. The person of skills in the art will appreciate that this comparison will depend upon the reference sample used. For example, if the reference sample is made of cancerous lung tissue obtained from a subject known to have poor prognosis, and there is a difference in the expression profiles (e.g. lower expression levels), then the tested lung cancer can be diagnosed as not aggressive, and the tested patient can be prognosed or classified in a good survival group. Likewise, if the expression profiles in that situation are similar, then the tested cancer can be diagnosed as aggressive, and the patient prognosed or classified in a poor survival group. On the other hand, if the reference sample is made of healthy tissue, and there is a difference in the expression profiles (e.g. higher expression levels), then the tested cancer can be diagnosed as aggressive, and the tested patient prognosed or classified in a poor survival group; whereas, if there is no difference in the expression profiles, then the tested cancer can be diagnosed as not aggressive, and the tested patient prognosed to a good survival group.

The term "differentially expressed" or "differential expression" as used herein refers to a difference in the level of expression of the genes of the invention that can be assayed by measuring the level of expression of the products of the said genes, such as the difference in level of messenger RNA transcript expressed or proteins expressed of the said genes. In a preferred embodiment, the difference is statistically significant. The term "difference in the level of expression" refers to an increase or decrease in the measurable expression level of a given gene as measured by the amount of messenger RNA transcript and/or the amount of protein in the test sample as compared with the measurable expression level of a given gene in a reference sample. The term "similarity in expression" as used herein means that there is no or little difference in the level of expression of the biomarkers between the test sample and the control or reference profile. For example, similarity can refer to a fold difference compared to a control. In a preferred embodiment, there is no statistically significant difference in the level of expression of the biomarkers.

The comparison of the expression profiles can be performed in a number of ways. Statistical analysis may be used. For example, comparison can be performed using the PLS regression (Partial Least Square) which aim is to extract components, which are linear combinations of the explanatory variables (the genes), in order to model the variable response (e.g.: 0 if not aggressive, 1 if aggressive). The PLS regression is particularly relevant to give prediction in the case of small reference samples. The comparison may also be performed using Support Vector Machines (SVM), logistic regression, Linear Discriminant Analysis, Random Forests, k-NN (k=3, 4, 5, 6) or PAM (predictive analysis of microarrays) statistical methods. Preferably Fisher's Linear Discriminant Analysis.

Preferably, the comparison of the expression profiles is performed by calculating an expression level ratio between the expression level in the test biological sample and the expression level in the reference sample for each of the genes of the signature, comprising or consisting of CDC6, CLASPIN, PLK1, and POLQ, and optionally RAD51.

The diagnosis of aggressiveness of the said lung cancer can be then obtained by comparing the obtained expression level ratio to a corresponding threshold value.

Therefore, the present invention provides a method for diagnosing aggressiveness of a lung cancer in a patient, comprising the steps of:
a) measuring an expression level in a biological sample of said patient for each of the genes of the DNA replication stress gene signature, said signature comprising the CDC6, CLASPIN, PLK1, and POLQ genes;
b) measuring an expression level in a reference sample of said patient for each of the said genes of the DNA replication stress gene signature;
c) calculating an expression level ratio between the expression level in the test biological sample and the expression level in the reference sample for each of the genes of the DNA replication stress gene signature, and
d) diagnosing aggressiveness or non-aggressiveness of the lung cancer by comparing the obtained expression level ratio to a corresponding threshold value.

In a preferred embodiment of the methods of the invention, the signature further comprises the RAD51 gene. In another preferred embodiment of the methods of the invention, the signature consists of the CDC6, CLASPIN, PLK1, and POLQ genes. In an even further preferred embodiment, the said signature consists of the CDC6, CLASPIN, PLK1, POLQ, and RAD51 genes.

A lung cancer is thus diagnosed to be aggressive if the ratio of each of the genes is superior to their corresponding threshold value when the reference sample is made of healthy tissue, or if the ratio of each of these genes is inferior to their corresponding threshold value when the reference sample is made of cancerous lung tissue. As mentioned above, it is advantageous to use a reference sample made of healthy lung tissue from the tested patient. In that particular embodiment, a lung cancer is diagnosed as aggressive, if the ratio of each of the said genes is superior to a threshold value.

In some embodiments, the method of the invention further comprises a step of normalizing the expression levels of the said signature genes with respect to the expression levels of one or more control genes, prior to calculating the expression level ratios. A "control gene", according to the present invention, is a gene which is expressed in all cell types. More specifically, the control gene according to the invention is a gene which is expressed in all the cells of the lung. In another aspect, the expression level of the control gene is not affected by the state of the cell, i.e. the control gene is expressed to the same level in a healthy lung cell and in a cancerous lung cell. In a specific embodiment, the control gene is a housekeeping gene. A housekeeping gene is a gene expressed in all cell types, which provides a basic function needed for sustenance of all cell types. A list of human housekeeping genes may be found in Eisenberg et al. (Trends in Genetics 19: 362-365, 2003). A preferred housekeeping gene according to the invention is a gene selected in the group consisting of B2M, TFRC, YWHAZ, RPLO, 18S, GUSB, UBC, TBP, GAPDH, PPIA, POLR2A, ACTB, PGK1, HPRT1, IPO8 and HMBS. A further preferred housekeeping gene according to the invention is selected from the group consisting of IPO8, HMBS, GUSB, and UBC.

In this embodiment, the expression levels of the said control gene are also measured in the tested lung-cancer sample and in the reference sample. The expression level is then normalized to the expression level of the control gene for each of the signature genes and for each sample. Then the expression level ratio is calculated between the normalized expression level in the lung-cancer sample and the normalized expression level in the reference sample. As mentioned above, aggressiveness is diagnosed by comparing the obtained expression level ratio to a corresponding threshold value.

According to the present invention, a "threshold value" is intended to mean a value that permits to discriminate samples in which the expression level ratio of the gene of interest corresponds to an expression level of said gene of interest in the patient's lung cancer sample that is low or high. In particular, when the reference sample is made of healthy lung tissue from the tested patient, if a gene expression level ratio is inferior or equal to the threshold value, then the expression level of this gene in the patient's lung cancer sample is considered low, whereas if a gene expression level ratio is superior to the threshold value, then the expression level of this gene in the patient's lung cancer sample is considered high. For each gene, and depending on the method used for measuring the expression level of the genes, the optimal threshold value may vary. However, it may be easily determined by a skilled artisan based on the analysis of several control cancer samples in which the expression level (low or high) is known for this particular gene, and on the comparison thereof with the expression of a control gene, e.g. a housekeeping gene.

The present invention further relates to a microarray dedicated to the implementation of the methods according to the invention, comprising at most 500, preferably at most 300, at most 200, more preferably at most 150, at most 100, even more preferably at most 75, at most 50, at most 40, at most 30, at most 20, at most 10 distinct probes, at least 4 of which specifically binds to the mRNA (or corresponding cDNA) or protein produced by the genes of the DNA replication stress signature of the invention.

In a preferred embodiment, said microarray is a nucleic acid microarray, comprising at most 500, preferably at most 300, at most 200, more preferably at most 150, at most 100, even more preferably at most 75, at most 50, at most 40, at most 30, at most 20, at most 10 distinct probes (thus excluding for instance pangenomic microarrays), at least 4 of which specifically hybridizes to the mRNA (or corresponding cDNA) produced by the genes of the DNA replication stress signature of the invention. Thus, in a more preferred embodiment, said microarray is a nucleic acid microarray, comprising at most 500, preferably at most 300, at most 200, more preferably at most 150, at most 100, even more preferably at most 75, at most 50, at most 40, at most 30, at most 20, at most 10 distinct probes, at least 4 of which specifically hybridizes to the mRNA (or corresponding cDNA) produced by the CDC6, CLASPIN, PLK1, and POLQ genes. In an even more preferred embodiment, said microarray is a nucleic acid microarray, comprising at most 500, preferably at most 300, at most 200, more preferably at most 150, at most 100, even more preferably at most 75, at most 50, at most 40, at most 30, at most 20, at most 10 distinct probes, at least 5 of which specifically hybridizes to the mRNA (or corresponding cDNA) produced by the CDC6, CLASPIN, PLK1, POLQ, and RAD51 genes. Said microarray may also contain at least one probe which specifically hybridizes to a housekeeping gene in addition to the probes specifically hybridizing to the genes of the DNA replication stress signature of the invention. In one embodiment, said housekeeping gene is selected in the group consisting of B2M, TFRC, YWHAZ, RPLO, 18S, GUSB, UBC, TBP, GAPDH, PPIA, POLR2A, ACTB, PGK1, HPRT1, IPO8 and HMBS. More preferentially, the housekeeping gene is selected from the group consisting of the IPO8, HMBS, GUSB, and UBC genes. According to the invention, a "nucleic microarray" consists of different nucleic acid probes that are attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes can be nucleic acids such as cDNAs ("cDNA microarray") or oligonucleotides ("oligonucleotide microarray", the oligonucleotides being about 25 to about 60 base pairs or less in length).

Alternatively, in another embodiment, said microarray may be an antibodies microarray, comprising at most 500, preferably at most 300, at most 200, more preferably at most 150, at most 100, even more preferably at most 75, at most 50, at most 40, at most 30, at most 20, at most 10 distinct antibodies, at least 4 of which specifically bind to the proteins produced by the genes of the DNA replication stress signature of the invention. Preferably, said microarray may be an antibodies microarray, comprising at most 500, preferably at most 300, at most 200, more preferably at most 150, at most 100, even more preferably at most 75, at most 50, at most 40, at most 30, at most 20, at most 10 distinct antibodies, at least 4 of which specifically bind to the proteins produced by the CDC6, CLASPIN, PLK1, and POLQ genes. More preferably, said microarray may be an antibodies microarray, comprising at most 500, preferably at most 300, at most 200, more preferably at most 150, at most 100, even more preferably at most 75, at most 50, at most 40, at most 30, at most 20, at most 10 distinct antibodies, at least 4 of which specifically bind to the proteins produced by the CDC6, CLASPIN, PLK1, POLQ, and RAD51 genes. Said microarray may also contain at least one antibody which specifically binds to a housekeeping protein, in addition to the antibodies specifically binding to the proteins produced by the genes of the DNA replication stress signature of the invention. In one embodiment, said housekeeping protein is selected in the group consisting of proteins produced by the B2M, TFRC, YWHAZ, RPLO, 18S, GUSB, UBC, TBP, GAPDH, PPIA, POLR2A, ACTB, PGK1, HPRT1, IPO8 and HMBS genes. In a preferred embodiment, said housekeeping protein is selected from the group consisting of the proteins produced by the IPO8, HMBS, GUSB, and UBC genes.

Alternatively to nucleic acid or antibody microarray technology, quantitative PCR may be used and amplification primers specific for the genes to be tested are thus also very useful for performing the methods according to the invention. The present invention thus further relates to a kit for diagnosing aggressiveness of a lung cancer in a patient from a lung cancer sample of said patient, comprising a dedicated microarray as described above or amplification primers specific for the genes of the DNA replication stress signature of the invention. Here also, when the kit comprises amplification primers, while said kit may comprise amplification primers specific for other genes, said kit preferably comprises at most 100, at most 75, 50, at most 40, at most 30, preferably at most 25, at most 20, at most 15, more preferably at most 10, at most 8, at most 6, even more preferably at most 5, at most 4, at most 3 or even 2 or one or even zero couples of amplification primers specific for other genes than the genes of the DNA replication stress signature of the invention. For example, said kit may comprise at least a couple of amplification primers for at least one housekeeping gene in addition to the primers for the genes of the DNA replication stress signature of the invention. In one embodiment, said housekeeping gene is selected in the group consisting of B2M, TFRC, YWHAZ, RPLO, 18S, GUSB, UBC, TBP, GAPDH, PPIA, POLR2A, ACTB, PGK1, HPRT1, IPO8 and HMBS. In a preferred embodiment, said housekeeping gene is selected from the group consisting of the IPO8, HMBS, GUSB, and UBC genes.

As mentioned above, the ability of prognosing lung cancer evolution, which is linked to its aggressiveness, is very important for selecting a suitable treatment, since heavy and costly treatments with potentially severe adverse effects should be used, in addition to traditional surgical treatment, each time they are necessary, but only when they are necessary.

The present invention thus provides a method for determining whether a lung cancer is susceptible to treatment with radiotherapy and/or a chemotherapeutic agent, comprising:
a) diagnosing or not aggressiveness of said lung cancer in said patient according to the methods to the invention as described above, and
b) determining that the said lung cancer is susceptible to treatment with radiotherapy and/or said chemotherapeutic agent if said lung cancer is diagnosed as aggressive in step a).

The chemotherapeutic agents of the invention include without any limitations, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and antifolate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors. In addition, the methods of the invention can be combined with another anti-cancer treatment, anti-angiogenic agent, or chemotherapeutic agent or radiation therapy. A preferred example is docetaxel or taxotere. Other examples include, gemcitabine, cisplatin diterpenoids and vinca alkaloids, paclitaxel, vinblastine, vincristine, and vinorelbine, carboplatin, cyclophosphamide, melphalan, and chlorambucil, busulfan, carmustine, dacarbazine, cyclophosphamide, melphalan, chlorambucil, busulfan, carmustine, dacarbazine, anti-neoplastic agents including, but not limited to, actinomycins such as dactinomycin, anthrocyclins such as daunorubicin and doxorubicin, bleomycins, epipodophyllotoxins, etoposide and teniposide; antimetabolite neoplastic agents, 5-fluorouracil, methotrexate, cytarabine, mecaptopurine, thioguanine, camptothecins, irinotecan HCl, and topotecan HCl.

A variety of different chemotherapeutic agents or anti-cancer polypeptides can also be selected. Information sources such as, world wide web clinical trials.gov, world wide web ncbi.nlm.nih and world wide web drugs.com, include references to polypeptides and agents that can be selected.

Preferably, the chemotherapeutic agent of the invention has been approved by at least one health authority for treating lung cancer. Example of such chemotherapeutic drugs which are particularly useful for treating lung cancer comprise Methotrexate, Pemetrexed Disodium, Bevacizumab, Carboplatin, Cisplatin, Methotrexate, Crizotinib, Erlotinib, Gemcitabine-Cisplatin, Gefitinib, Paclitaxel, Carboplatin, Pemetrexed, Cisplatin, Crizotinib, Etoposide, and Topotecan In another preferred embodiment, the chemotherapeutic agent is genotoxic. This embodiment is particularly advantageous, since overexpression of any of the genes of the signature is expected to interfere with DNA replication, thus inducing hypersensitivity to genotoxic agent. Preferably, the said genotoxic agent is an inhibitor of DNA repair, DNA replication/damage checkpoint, or DNA replication licensing/initiation.

According to the invention, a "DNA repair inhibitor" is intended to mean a molecule that is able to inhibit repair of DNA breaks, in particular double stranded DNA breaks. While this expression should not be understood as limitative, examples of DNA repair inhibitors include inhibitors of DNA repair protein PARP (see e.g. WO 2004080976, WO 2005/053662, WO 2009/046205), inhibitors of histone deacetylase, such as those described in PCT application WO 2008/082856, and inhibitors of DNA polymerase β (see WO 2007/001684). A "DNA replication/damage checkpoint inhibitor" is a molecule which is capable of blocking the activity of any of the proteins involved in the DNA replication checkpoint or in the DNA damage checkpoint. Examples of such proteins include ATM/ATR, Chk2 and Chk1. A "DNA replication licensing/initiation inhibitor". is a molecule capable of blocking the activity of any of the proteins involved in DNA replication licensing, such as Cdt1, Mcm1-7, and other known to the skilled person.

In another aspect, the present invention also concerns a method for choosing a suitable treatment for a patient with a lung cancer, comprising:
a) diagnosing or not aggressiveness of said lung cancer in said patient according to the methods to the invention as described above, and
b) adding adjuvant radiotherapy and/or chemotherapeutic agent to surgical treatment if said cancer is diagnosed as aggressive in step a).

The term "adjuvant chemotherapy" as used herein means treatment of cancer with chemotherapeutic agents after surgery where all detectable disease has been removed, but where there still remains a risk of small amounts of remaining cancer.

The invention also relates to a method for designing a treatment with radiotherapy and/or a chemotherapeutic agent for a lung cancer-suffering subject, said method comprising the steps of:
a) diagnosing or not aggressiveness of said lung cancer in said patient according to the methods to the invention as described above, and
b) determining the dose of radiotherapy or chemotherapeutic agent treatment according to the diagnosis of step a).

For the purpose of the application, it is understood that when the lung cancer is diagnosed as being aggressive, the dose of step b) is greater than when the lung cancer is diagnosed as non-aggressive.

Optionally, the dose of radiotherapy or chemotherapeutic agent determined in step (b) is administered to the subject.

The invention also refers to the use of a chemotherapeutic agent for manufacturing a medicament for the treatment of lung cancer, comprising the steps of:
a) diagnosing or not aggressiveness of said lung cancer in said patient according to the methods to the invention as described above, and
b) determining the dose of chemotherapeutic agent treatment according to the diagnosis of step a).

Optionally, the dose of chemotherapeutic agent determined in step (b) is administered to the subject.

The invention also relates to a chemotherapeutic agent for use in treating lung cancer, wherein the chemotherapeutic agent is administered to a lung cancer-suffering subject whose lung cancer has been diagnosed as aggressive using a method according to the invention.

More specifically, the invention relates to a chemotherapeutic agent for use in treating colorectal cancer in a subject suffering from a lung cancer, wherein:

a) the aggressiveness or on-aggressiveness of the said lung cancer is determined according to the method of the invention,
b) the dose of chemotherapeutic agent treatment is determined according to said identified chemotherapeutic agent-responding or non-responding phenotype, and
c) the dose of the chemotherapeutic agent which is determined in step b) is administered to the said subject.

The invention is also drawn to a method for adapting the treatment of a lung cancer-suffering subject with radiotherapy or a chemotherapy agent, comprising:
a) diagnosing or not aggressiveness of said lung cancer in said patient according to the methods to the invention as described above, and
b) adapting the radiotherapy or chemotherapeutic agent treatment according to the diagnosis of step a).

Said adaptation of the chemotherapeutic agent treatment may consist in:
a reduction or suppression of the said radiotherapy or chemotherapeutic agent treatment if the lung cancer has been diagnosed as non-aggressive, or
the continuation of the said treatment with said radiotherapy or chemotherapeutic agent if the said lung cancer has been diagnosed as aggressive.

The present invention also relates to a method for treating a patient suffering from a lung cancer, comprising diagnosing or not aggressiveness of said lung cancer in said patient according to the methods to the invention as described above, and subjecting said patient to radiotherapy and/or administering to said patient an effective amount of one or more DNA repair inhibitors.

The practice of the invention employs, unless other otherwise indicated, conventional techniques or protein chemistry, molecular virology, microbiology, recombinant DNA technology, and pharmacology, which are within the skill of the art. Such techniques are explained fully in the literature. (See Ausubel et al., Current Protocols in Molecular Biology, Eds., John Wiley & Sons, Inc. New York, 1995; Remington's Pharmaceutical Sciences, 17th ed., Mack Publishing Co., Easton, Pa., 1985; and Sambrook et al., Molecular cloning: A laboratory manual 2nd edition, Cold Spring Harbor Laboratory Press—Cold Spring Harbor, N.Y., USA, 1989).

Other characteristics and advantages of the invention appear in the continuation of the description with the examples and the figures whose legends are represented below.

FIGURES LEGENDS

The patent or application file contains at least one color drawing. Copies of this patent or patent application publication with color drawing will be provided by the USPTO upon request and payment of the necessary fee.

FIG. 1A-1E. Effect of CDC6, CLASPIN, PLK1, POLQ, and RAD51 gene expression level on cancer-specific survival of patients. Kaplan-Meier overall survival of pulmonary adenocarcinoma patients, according to level of DNA POLQ (A), PLK1 (B), CLASPIN (C), CDC6(D), and RAD51 (E) expression in the primary tumor compared to adjacent normal tissue. Patients: n=93; p values taken from each log-rank test are indicated.

Figures 2A, 2B:
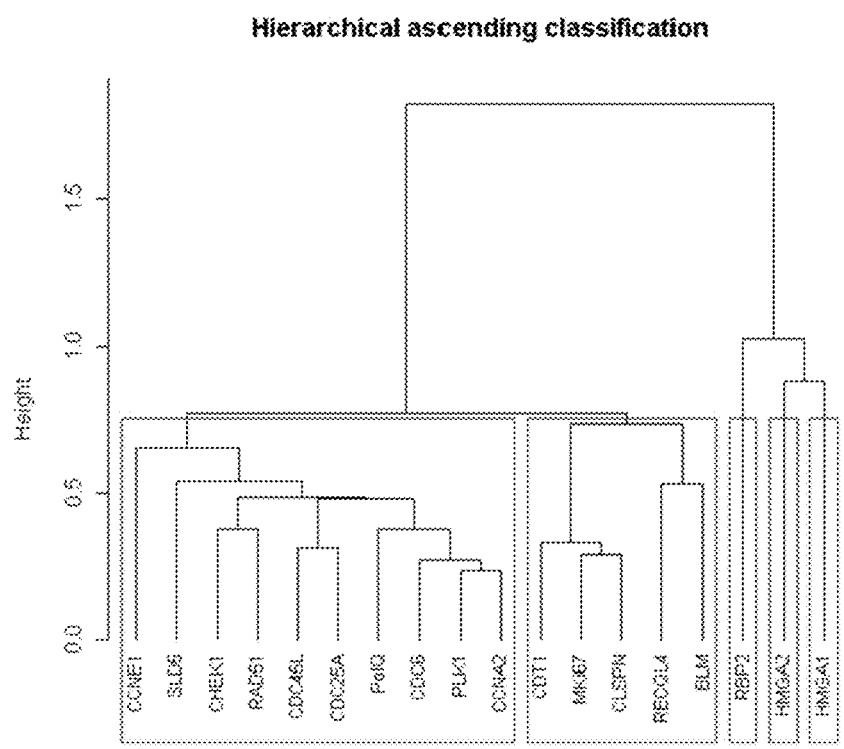

FIG. 2A-2B. Concomitant expression of the CDC6, CLASPIN, PLK1, POLQ, and RAD51 genes in primary tumors. Pearson test analysis (A) and hierarchical ascending classification (B).

EXAMPLES

Material and Methods
Patients, Tumor Samples

Coupled tumor samples (n=93) were surgically collected from 2006 to 2010 from patients diagnosed at the Rangueil-Larrey Toulouse hospital (France) with untreated (at the moment of the biopsy) primary lung adenocarcinoma from stage I to III. Samples were immediately snap-frozen in liquid nitrogen. Normal lung tissues were taken from the surgical specimens, at more than 3 cm of distance from the tumor. Eligibility criteria included our ability to get frozen tumor and adjacent healthy tissues as well as extracted RNAs of high quality. Exclusion criteria include non-adenocarcinoma tumors, stages IIIb and IV and tumoral cellularity below 70% tumor cells. The tumor stages and morphology were defined from frozen tissues by a pathologist according to the Tumor, Node, Metastasis (TNM) staging classification following 2010 WHO guidelines and Hematoxylin-Eosin staining, respectively. The characteristics of the patients and tumors for both cohorts are described in Table S1.

RNA Extraction and Quantification

Thick frozen sections of tissues were obtained by using a LEICA CM3050S cryostat. 10 μm (n=60) and 300 μm (n=3-5) thick sections of the frozen tissue were crisped during 90 s by using 5-mm diameter stainless steal beads and a tissue lyser (Qiagen), then total RNA was extracted with the RNeasy extraction kit according to the manufacturer (Qiagen). The quality of total RNA (DO260/DO280>1.7) was assessed with the Agilent 2100 bio-analyzer using the RNA Nano Lab chip, 6000 Nano Assay kit (Agilent Technologies). Its quantity was estimated with Nanodrop (Thermoscientific). The four most stable control housekeeping genes (GUSB, 1PO8, HMBS, UBS) were selected by the GeNorm and BestKeeper softwares among 16 tested on the TaqMan Low Density Human Edogenous Control Array (Applied Biosystems) after amplifying in triplicate 800 ng cDNA from 4 coupled biopsies using the TaqMan Universal PCR Master Mix, the TaqMan Low Density Array technology (Applied Biosystems) and the 7900HT fast real time PCR system.

To quantify RNAs from tumour and normal tissues, cDNAs were first pre-amplified in the presence of the 3R probes (TaqMan gene Expression Assays, Applied Biosystems) in TaqMan Preamp Master Mix (Early Access, Applied Biosystems). These products were then amplified using the Dynamic Array technology (Fluidigm, BioMark). Pre-amplified products were incubated in DNA Binding Sample Loading reagent (BioMark), Master Mix (Applied) and probes then injected in nanotubes-containing Integrated Fluidic Circuit loader then amplified with the BioMark amplifier. Fluidigm data were analyzed with the GenEx software after normalizing in tumor (T) and normal (N) tissues the levels of transcripts to the mean level of the 4 selected stable genes. Relative levels of expression in the tumor sample compared to the adjacent normal tissue were expressed by T/N ratios. T/N>1 indicates a higher expression in the tumour sample compared to the adjacent normal tissue. T/N<1 means a lower expression in cancers than in control tissues.

Statistical Analysis

Statistical analyses were performed using the free statistical software R (version 2.9.2) including the "Survival", "DiagnosisMed" and "rpart" packages (R development Team, http://crans-project.org/) and Stata SE 11.2 software (Stata Corporation, College Station, Tex., USA). When comparing the expressions in cancer tissues the major parameters were the individual T/N ratios. The probability to observe more than 50% of patients overexpressing or underexpressing 3R genes (threshold: T/N>1 for overexpression and T/N<1/2 for underexpression) was assessed by a binomial test. Other thresholds were tested in the same way (T/N>5 or T/N<1/5, T/N>4 or T/N<1/4, T/N>3 or T/N<1/3, and T/N>2 or T/N<1/2). Correlations between genes were assessed with a Pearson correlation coefficient. A clustering algorithm was also applied: hierarchical ascending classification (HAC). This clustering was carried out for genes using Ward's method of linkage and correlation distance as a metric. Expression levels were classified in 3 categories according to the terciles of the T/N distribution. Expression levels were compared by chi-square or Fisher's exact test in relation to the treatment (surgery only, surgery-chemotherapy-radiotherapy, or surgery-chemotherapy), to the tumor grade (N or TNM), of the tumor differentiation (poorly-, moderately-, or well-differentiated), of the presence of emboli, and of the smoking habits. Survival probabilities were estimated using Kaplan Meier method (overall survival, disease free survival and relapse free survival). The Log Rank test was used to compare survival curves. Survival rates in relation to the expression levels was estimated according to the Kaplan-Meier method and a multivariate Cox's proportional hazards regression model adjusted on sex, age, treatment, tumor grade, and expression level of Ki67 and PCNA genes. We explored the association between gene expression and overall survival using a recursive partitioning procedure. It appeared that the first three genes that gave the best split at the first node were strongly correlated and had also been identified as significantly associated with the overall survival in multivariate Cox regression models. A final multivariate Cox regression model has been computed to test the combination of either one of these three gene expression greater than the thresholds given by the recursive partitioning procedure.

P-values for binomial test were one-sided. All other p-values were two-sided. For all statistical tests, differences were considered significant at the 5% level.

Results

In this study, we assessed in primary tumors and adjacent normal tissues from a series of 93 NSCLC patients the expression of 78 genes involved in DNA replication. We found that many of these genes were significantly deregulated in tumors. More importantly the misregulation of some of them is a determinant of survival after surgical treatment, independently of the therapeutic strategies or tumour stages. Indeed, a 4-gene signature including CDC6, CLASPIN, PLK1, and POLQ genes separated patients to high-risk and low-risk subgroups with significantly different survival and independently of treatments or node status (hazard ratio [HR], 36.31 (95% CI 2.6-517.4 P=0.04), [HR], 23.49 (95% CI 1.9-288.4 P=0.01), [HR], 18.50 (95% CI 1.3-267.4 P=0.01) and [HR], 20.65 (95% CI 1.5-275.9 P=0.05), respectively).

Most of DNA Replication Genes are Deregulated in Coupled Lung Tumors

Gene expression profiles of 93 coupled primary lung adenocarcinomas at different early or mid-stages of progression (Table 1) were generated from a selection of 78 genes involved in the course of genome replication i.e. initiation/licensing at replication origins, translesional (TLS) or conventional DNA elongation, S-phase associated DNA damage response (DDR), DNA fork protection or replication-induced double-stranded break (DSB) repair (Table 2). We then identified which of these genes were up- or down-regulated in tumors (T) compared to adjacent control tissues (N). Deregulated genes were stratified in two groups based on the number of tumors in which T/N expression ratio was either over or under two. Knowing that we did not find any gene more than 2-fold down-regulated (data not shown), we also evidenced those which displayed a ½<T/N<2 ratio i.e. almost unchanged or less than 2-fold down-regulated (Table 2). Individual levels of expression in all the 93 coupled tumors were also shown for some representative DNA replication genes (FIG. S2).

TABLE 1

| baseline characteristics of patients (n = 93) | |
|---|---|
| Smoking, n (%) | |
| No smoker | 30 (33.33) |
| Smoker | 60 (66.67) |
| Presurgery chemotherapy, n (%) | |
| No | 84 (90.32) |
| Yes | 9 (9.68) |
| Presurgery radiotherapy, n (%) | |
| No | 93 (100) |
| Yes | 0 (0) |
| Postsurgery chemotherapy, n (%) | |
| No | 52 (55.91) |
| Yes | 41 (44.09) |
| Postsurgery radiotherapy, n (%) | |
| No | 82 (88.17) |
| Yes | 11 (11.83) |
| WHO type, n (%) | |
| Mixt | 59 (64.13) |
| Acinar | 15 (16.3) |
| Papillary | 4 (4.35) |
| Massive | 13 (14.13) |
| Bronchioloalveolar | 1 (1.09) |
| Tumor differentiation, n (%) | |
| Low | 16 (17.39) |
| Medium | 43 (46.74) |
| High | 33 (35.87) |
| Emboli, n (%) | |
| No | 45 (50) |
| Yes | 45 (50) |
| TNM stage, n (%) | |
| 0 | 1 (1.08) |
| IA | 26 (27.96) |
| IB | 33 (35.48) |
| IIA | 3 (3.23) |
| IIB | 10 (10.75) |
| IIIA | 20 (21.51) |
| Age (years), mean ± standard deviation | 61.60 ± 10.2 |
| Number pack/year, mean ± standard deviation | 36.64 ± 16.8* |

ND: not determined

As controls we first confirmed (Table 2) as already published the inhibition of the APC (11) and p53 (12) tumor suppressors as well as the ERCC1 DNA repair gene (13). Conversely and as expected, KI67, which is involved in ribosome biogenesis and currently used by pathologists as a proliferative marker was over-expressed.

TABLE 2

Differential expression of 78 "DNA replication" genes in 93 coupled NSCLC tumors

| DNA replication genes | DNA transaction | Coupled tumors total n | Slightly over-expressed or downregulated expression | | | | Over-expression T/N > 2 | | Uncorrected P-value |
|---|---|---|---|---|---|---|---|---|---|
| | | | 0.5 < T/N < 1 | | 1 < T/N < 2 | | | | |
| | | | n | (%) | n | (%) | n | (%) | |
| APC | Wnt signaling (control) | 93 | 93 | (100.0%) | 0 | (0.0%) | 0 | (0.0%) | <0.000001* |
| KI67 | Cell proliferation (control) | 93 | 2 | (2.2%) | 9 | (9.7%) | 82 | (88.2%) | <0.000001* |
| REV3 (POLZ) | TLS DNA replication | 93 | 89 | (95.7%) | 4 | (4.3%) | 0 | (0.0%) | <0.00001* |
| Polk | TLS DNA replication | 93 | 82 | (88.2%) | 11 | (11.8%) | 0 | (0.0%) | <0.000001* |
| PolI | TLS DNA replication | 93 | 78 | (83.9%) | 15 | (16.1%) | 0 | (0.0%) | <0.000001* |
| PolG | TLS DNA replication | 93 | 74 | (79.6%) | 18 | (19.4%) | 1 | (1.1%) | <0.000001* |
| SHPRH | TLS DNA replication | 93 | 73 | (78.5%) | 19 | (20.4%) | 1 | (1.1%) | <0.000001* |
| REV1 | TLS DNA replication | 93 | 78 | (83.9%) | 13 | (14.0%) | 2 | (2.2%) | <0.000001* |
| PolH | TLS DNA replication | 93 | 58 | (62.4%) | 32 | (34.4%) | 3 | (3.2%) | <0.000001* |
| PolL | TLS DNA replication | 93 | 59 | (63.4%) | 31 | (33.3%) | 3 | (3.2%) | <0.000001* |
| PolM | TLS DNA replication/DNA repair | 93 | 29 | (31.2%) | 51 | (54.8%) | 13 | (14.0%) | <0.000001* |
| PolB | TLS DNA replication/DNA repair | 93 | 27 | (29.0%) | 45 | (48.4%) | 21 | (22.6%) | <0.000001* |
| RAD6 | TLS DNA replication | 93 | 42 | (45.2%) | 48 | (51.6%) | 3 | (3.2%) | <0.000001* |
| RAD18 | TLS DNA replication | 93 | 36 | (38.7%) | 52 | (55.9%) | 5 | (5.4%) | <0.000001* |
| PolQ | TLS DNA replication | 93 | 3 | (3.2%) | 15 | (16.1%) | 75 | (80.6%) | <0.000001* |
| ORC4 | Initiation/Licensing | 93 | 55 | (59.1%) | 37 | (39.8%) | 1 | (1.1%) | <0.000001* |
| CUL4 | Initiation/Licensing | 93 | 52 | (55.9%) | 38 | (40.9%) | 3 | (3.2%) | <0.000001* |
| DBF4 | Initiation/Licensing | 93 | 28 | (30.1%) | 41 | (44.1%) | 24 | (25.8%) | 0.000003* |
| MCM7 | Initiation/Licensing | 93 | 21 | (22.6%) | 43 | (46.2%) | 29 | (31.2%) | 0.0004* |
| CDC7 | Initiation/Licensing | 93 | 24 | (25.8%) | 35 | (37.6%) | 34 | (36.6%) | 0.01 |

TABLE 2-continued

Differential expression of 78 "DNA replication" genes in 93 coupled NSCLC tumors

| Gene | Function | n | | | | | | | p-value |
|---|---|---|---|---|---|---|---|---|---|
| GEMININ | Initiation/Licensing | 93 | 3 | (3.2%) | 39 | (41.9%) | 51 | (54.8%) | 0.41 |
| TIMELESS | Initiation/Licensing | 93 | 2 | (2.2%) | 36 | (38.7%) | 55 | (59.1%) | 0.10 |
| SLD5 | Initiation/Licensing | 93 | 4 | (4.3%) | 23 | (24.7%) | 66 | (71.0%) | 0.00006* |
| CYCLIN E | Initiation/Licensing | 93 | 4 | (4.3%) | 19 | (20.4%) | 70 | (75.3%) | 0.000001* |
| CYCLIN A | Initiation/Licensing | 93 | 3 | (3.2%) | 11 | (11.8%) | 79 | (84.9%) | <0.000001* |
| CDC45 | Initiation/Licensing | 93 | 0 | (0.0%) | 9 | (9.7%) | 84 | (90.3%) | <0.000001* |
| PLK1 | Initiation/Licensing | 93 | 3 | (3.2%) | 4 | (4.3%) | 86 | (92.5%) | <0.000001* |
| CDC6 | Initiation/Licensing | 93 | 1 | (1.1%) | 4 | (4.3%) | 88 | (94.6%) | <0.000001* |
| HMGA1 | Initiation/Licensing | 93 | 4 | (4.3%) | 15 | (16.1%) | 74 | (79.6%) | <0.000001* |
| HMGA2 | Initiation/Licensing | 93 | 23 | (24.7%) | 4 | (4.3%) | 66 | (71.0%) | 0.00006* |
| TIP60 | DSB repair | 93 | 90 | (96.8%) | 3 | (3.2%) | 0 | (0.0%) | <0.000001* |
| XLF | DSB repair | 93 | 75 | (80.6%) | 18 | (19.4%) | 0 | (0.0%) | <0.000001* |
| Lig4 | DSB repair | 93 | 60 | (64.5%) | 30 | (32.3%) | 3 | (3.2%) | <0.000001* |
| XRCC1 | DSB repair | 93 | 51 | (54.8%) | 38 | (40.9%) | 4 | (4.3%) | <0.000001* |
| P300 | DNA repair/Chromatin assembly | 93 | 71 | (76.3%) | 20 | (21.5%) | 2 | (2.2%) | <0.000001* |
| Lig3 | DSB repair | 93 | 28 | (30.1%) | 55 | (59.1%) | 10 | (10.8%) | <0.000001* |
| XRCC4 | DSB repair | 17 | 6 | (35.3%) | 9 | (52.9%) | 2 | (11.8%) | 0.002* |
| LAMIN B | DSB repair | 93 | 13 | (14.0%) | 53 | (57.0%) | 27 | (29.0%) | 0.00006* |
| DNAPKcs | DSB repair | 93 | 16 | (17.2%) | 46 | (49.5%) | 31 | (33.3%) | 0.002* |
| RAD51 | DSB repair | 93 | 2 | (2.2%) | 21 | (22.6%) | 70 | (75.3%) | 0.000001* |
| PCNA | DNA replication/DNA repair | 93 | 13 | (14.0%) | 57 | (61.3%) | 23 | (24.7%) | 0.000001* |
| PolA | DNA replication | 93 | 50 | (53.8%) | 35 | (37.6%) | 8 | (8.6%) | <0.000001* |
| PolE | DNA replication | 93 | 34 | (36.6%) | 39 | (41.9%) | 20 | (21.5%) | <0.000001* |
| PolD | DNA replication | 93 | 35 | (37.6%) | 35 | (37.6%) | 23 | (24.7%) | 0.000001* |
| MCM8 | DNA replication | 93 | 21 | (22.6%) | 39 | (41.9%) | 33 | (35.5%) | 0.007* |
| CHTF18 | DNA replication | 93 | 16 | (17.2%) | 43 | (46.2%) | 34 | (36.6%) | 0.01 |
| SIRT1 | DNA repair/DDR | 93 | 78 | (83.9%) | 14 | (15.1%) | 1 | (1.1%) | <0.000001* |

TABLE 2-continued

Differential expression of 78 "DNA replication" genes in 93 coupled NSCLC tumors

| Gene | Category | N | T/N>2 | | T/N≈1 | | T/N<2 | | P-value† |
|---|---|---|---|---|---|---|---|---|---|
| MORF4 | DNA repair/DDR | 38 | 17 | (44.7%) | 4 | (10.5%) | 17 | (44.7%) | 0.63 |
| ERCC1 | DNA repair (control) | 93 | 68 | (73.1%) | 25 | (26.9%) | 0 | (0.0%) | <0.000001* |
| SIRT6 | DNA repair/DDR | 93 | 54 | (58.1%) | 39 | (41.9%) | 0 | (0.0%) | <0.000001* |
| BACH1 | DNA fork protection | 93 | 85 | (91.4%) | 8 | (8.6%) | 0 | (0.0%) | <0.000001* |
| RECQ1 | DNA fork protection | 93 | 75 | (80.6%) | 15 | (16.1%) | 3 | (3.2%) | <0.000001* |
| SMC5 | DNA fork protection | 93 | 73 | (78.5%) | 19 | (20.4%) | 1 | (1.1%) | <0.000001* |
| SMARCAL1 | DNA fork protection | 93 | 44 | (47.3%) | 48 | (51.6%) | 1 | (1.1%) | <0.000001* |
| FANCM | DNA fork protection | 93 | 39 | (41.9%) | 45 | (48.4%) | 9 | (9.7%) | <0.000001* |
| SLX4 | DNA fork protection | 93 | 27 | (29.0%) | 54 | (58.1%) | 12 | (12.9%) | <0.000001* |
| RUVBL1 | DNA fork protection | 93 | 15 | (16.1%) | 55 | (59.1%) | 23 | (24.7%) | 0.000001* |
| BRCA2 | DNA fork protection | 93 | 18 | (19.4%) | 44 | (47.3%) | 31 | (33.3%) | 0.002* |
| DSCC1 | DNA fork protection | 93 | 23 | (24.7%) | 28 | (30.1%) | 42 | (45.2%) | 0.41 |
| BLM | DNA fork protection | 93 | 8 | (8.6%) | 21 | (22.6%) | 64 | (68.8%) | 0.0004* |
| RECQ4 | DNA fork protection | 93 | 2 | (2.2%) | 16 | (17.2%) | 75 | (80.6%) | <0.000001* |
| P53 | DDR (control) | 93 | 74 | (79.6%) | 15 | (16.1%) | 4 | (4.3%) | <0.000001* |
| MRGX | DDR | 93 | 89 | (95.7%) | 4 | (4.3%) | 0 | (0.0%) | <0.000001* |
| ASF1 | DDR | 93 | 72 | (77.4%) | 21 | (22.6%) | 0 | (0.0%) | <0.000001* |
| ATM | DDR | 93 | 63 | (67.7%) | 29 | (31.2%) | 1 | (1.1%) | <0.000001* |
| MCM9 | DDR | 93 | 68 | (73.1%) | 24 | (25.8%) | 1 | (1.1%) | <0.000001* |
| RPA | DDR | 93 | 56 | (60.2%) | 35 | (37.6%) | 2 | (2.2%) | <0.000001* |
| RAD17 | DDR | 93 | 47 | (50.5%) | 44 | (47.3%) | 2 | (2.2%) | <0.000001* |
| RAD9 | DDR | 93 | 32 | (34.4%) | 52 | (55.9%) | 9 | (9.7%) | <0.000001* |
| 53BP1 | DDR | 93 | 39 | (41.9%) | 41 | (44.1%) | 13 | (14.0%) | <0.000001* |
| ATR | DDR | 93 | 23 | (24.7%) | 55 | (59.1%) | 15 | (16.1%) | <0.000001* |
| TOPBP1 | DDR | 93 | 30 | (32.3%) | 45 | (48.4%) | 18 | (19.4%) | <0.000001* |
| MRG15 | DDR | 93 | 26 | (28.0%) | 49 | (52.7%) | 18 | (19.4%) | <0.000001* |
| BRCA1 | DDR | 93 | 22 | (23.7%) | 33 | (35.5%) | 38 | (40.9%) | 0.10 |
| FANCD2 | DDR | 93 | 7 | (7.5%) | 44 | (47.3%) | 42 | (45.2%) | 0.41 |
| CDC25A | DDR | 93 | 8 | (8.6%) | 12 | (12.9%) | 73 | (78.5%) | <0.000001* |
| CHK1 | DDR | 93 | 2 | (2.2%) | 14 | (15.1%) | 77 | (82.8%) | <0.000001* |
| CLASPIN | DDR | 93 | 1 | (1.1%) | 13 | (14.0%) | 79 | (84.9%) | <0.000001* |

†Bilateral binomial tests;
*significantly more than 50% of the population have T/N > 2 or T/N < 2 according to the corrected overall critical P-value by the Benjamini and Yakutieli method (<0.0087)

The genes involved in the "initiation" and/or the "firing/licensing" of DNA replication at the about 50,000 replication origins dispersed along the genome e.g. SLD5, CYCLIN A, CYCLIN E, CDC45, CDT1, PLK1, and CDC6 and at a lesser extent DBF4 and MCM7 were mainly significantly more expressed in tumors compared to controls (Table 2). The less conventional non-histone HMGA1 and HMGA2 genes, which encode proteins that interact with the ORC origin sensors and are also directly involved in this transaction (15, 16), were also over-expressed. Interestingly, the expression of the inhibitors of the MOM-loader CDT1 i.e. GEMININ and CUL4 were conversely unchanged or inhibited, respectively. This was also the case for the ORC4 origin sensor, probably because ORC proteins play also additional roles such as chromosome cohesion (17).

Secondly we investigated the DNA polymerase family, which is in charge of either the error-prone replication of the undamaged genome (POLA, POLD, POLE) or the mostly inaccurate DNA damage bypass or repair synthesis by the translesional (TLS) nuclear (POLZ, POLK, POLI, REV1, POLH, POLL, POLM, POLB, REV1, POLQ) or the mitochondrial (POLG) DNA polymerases. We found as also observed in colorectal (14) and breast cancer (18) a mainly concomitant defective expression of POLG and all the nuclear TLS polymerases with the exception of POLB and POLM, whose biological roles are less translesion than repair synthesis following base excision and non-homologous end joining, respectively (19, 20). SHPRH, which is involved in the ubiquitination of PCNA and the recruitment onto DNA damage of the down-regulated Y-TLS POLH, POLK, POLI, and REV1 polymerases (21), was also down-regulated. In contrast, the expression of the replicative nuclear POLE and POLD DNA polymerases, as well as their PCNA processive co-factor, and the MCM8 elongating DNA helicase (22) were slightly over-expressed (Table 2). Finally, POLQ (WO/2011/058143) is the only DNA polymerase significantly over-represented in tumors compared to normal tissues.

Then we investigated the expression of genes involved in the intra S-phase DNA damage response (DDR). The DNA damage sensors were inhibited (ATM, RAD17) or slightly modified (53BP1, ATR, RAD9). The new MCM2-8 family member MCM9, which is likely to play a role in the S-phase checkpoint (23), ASF1, a histone chaperone implicated in derepression of DDR in stressed cells (24) as well as MRGX, which mediates DDR (25), were also down-regulated. Regarding DDR genes involved in the more downstream protection (the so-called "mediators") of the DNA replication forks, which are stalled by DNA damage, some (BACH1, RECQ and the SMC5 cohesin) were down-expressed whereas others where very (BLM, RECQ4) or slightly (SMARCAL1, SLMC5, FANCM, SLX4, RUVBL1, BRCA2) over-regulated.

Finally, except the RAD51 recombinase (Table 2), the expression of genes involved in DNA repair of replication-induced DNA damage such as DNA breaks i.e. TIP60, XLF, LIG4, XRCC1, LIG3, XRCC4, DNAPKcs, LAMIN B, all involved in conventional or alternative Non Homologous End Joining of DNA breaks, POLB, the Base Excision Repair DNA polymerase, Sirtuin 6 (SIRT6), which promotes DNA repair under stress (26), p300 and SIRT1, the two latter being involved in the histone expression and regulation of DDR genes (27), were inhibited or almost unchanged (Table 2).

Whereas exact binomial tests indicated that inhibited genes were no more than 2-fold down-expressed in tumors compared to normal tissues (data not shown and Table 2), seventeen genes were in contrast more than 2-fold overexpressed in tumors (Table 3). They include CYCLIN A, RECQ4, POLQ, CLASPIN and CHK1 from one hand and CDC45, CDC6, the positive control KI67, HMGA2 and CDT1 from the other, which were significantly expressed over a T/N threshold of 3 and 4, respectively. The PLK1 gene encoding the Polo-like-kinase (PLK1), which is recruited by the S-phase checkpoint Timeless protein and phosphorylates CDC6, playing probably a key role in the switch between mitotic exit and DNA replication licensing (28), was even more than 5-times over-expressed in lung tumors compared to healthy tissues.

TABLE 3 exact binomial tests after setting 4 different T/N thresholds

| Replication genes | DNA transaction | n | Under expression n (T/N < 1/Th)* | Neither over- nor under-expression * | Over expression (T/N > Th)* | Uncorrected P value** | T/N threshold (Th) |
|---|---|---|---|---|---|---|---|
| PLK1 | Initiation/Licensing | 93 | 0 | 25 | 68 | 4.69E−06 | 5 |
| CDC45 | Initiation/Licensing | 93 | 0 | 23 | 70 | 5.51E−07 | 4 |
| CDC6 | Initiation/Licensing | 93 | 0 | 24 | 69 | 1.65E−06 | 4 |
| CDT1 | Initiation/Licensing | 93 | 0 | 27 | 66 | 0.000032 | 4 |
| HMGA2 | DNA elongation | 93 | 10 | 26 | 57 | 0.000013 | 4 |
| Ki67 | Cell proliferation | 93 | 0 | 24 | 69 | 1.65E−06 | 4 |
| CYCLIN A | Initiation/Licensing | 93 | 0 | 21 | 72 | 5.19E−08 | 3 |
| CLASPIN | DDR | 93 | 0 | 28 | 65 | 0.000079 | 3 |
| RECQ4 | DNA fork protection | 93 | 0 | 26 | 67 | 0.000013 | 3 |
| POLQ | TLS | 93 | 0 | 27 | 66 | 0.000032 | 3 |
| CHK1 | DDR | 93 | 0 | 29 | 64 | 0.000183 | 3 |
| CYCLIN E | Initiation/Licensing | 93 | 0 | 23 | 70 | 5.51E−07 | 2 |
| SLD5 | Initiation/Licensing | 93 | 0 | 27 | 66 | 0.000032 | 2 |
| CDC25A | DDR | 93 | 1 | 19 | 73 | 3.86E−09 | 2 |
| BLM | DNA fork protection | 93 | 0 | 29 | 64 | 0.000183 | 2 |
| RAD51 | DSB repair | 93 | 0 | 23 | 70 | 5.51E−07 | 2 |
| HMGA1 | DNA elongation | 93 | 0 | 19 | 74 | 3.86E−09 | 2 |

*T/N > Th means a more than Th-fold over-expression.
**Significant over-expression compared to the corrected overall p-value by Benjamini and Yekutielli method ($p < 0.00021$ for Th = 5; $p < 0.00074$ for Th = 4; $p < 0.0013$ for Th = 3; and $p < 0.0019$ for Th = 2)

To investigate whether the overexpression of these genes was related or not to the proliferating status of the cancer tissues, we used a Pearson test to compare these misregulation levels with that of the Ki67 proliferation marker (data not shown). We found that among over-expressed genes, misregulation in tumors of HMGA2 (rho=0.1) as well as SLD5, CYCLIN E, RECQ4 and HMGA1 (all four rhos=0.6) were not dependent on this proliferation status.

Deregulated 3R Expression is Associated with a Poor Prognosis

The ultimate goal of our study was to identify DNA replication genes whose expression level in tumors could be informative about the patient's survival. A log-rank test for equality of survivor functions indicated that 9 DNA replication genes including POLQ (p=0.0008), PLK1 (p=0.0062), RAD51 (p=0.007), CYCLIN A (p=0.0128), CDC25A (p=0.0196), CLASPIN (p=0.0233), CDC6 (p=0.0404), POLL (p=0.0464) and RPA (p=0.0458) were associated with a lower overall survival morbidity (Table 4). It was also the case as already published for the DNA repair ERCC1 gene control (p=0.0256, (13)). Disease-free survival was also significantly associated with misregulation of the control Ki67 proliferation and prognosis marker (p=0.0051), as well as the CLASPIN (p=0.0005), TIMELESS (p=0.0127), CHK1 (p=0.0003), CYCLIN A (p=0.0017), 53BP1 (p=0.0339), SIRT1 (p=0.0056), BRCA1 (p=0.0008) and CDC25A (p=0.011) DDR genes, the CDC45 (p=0.0025), CYCLIN E (p=0.0405), CDC6 (p=0.0103), CDT1 (p=0.0101), PLK1 (p=0.0001) and GEMININ (p<0.0005) initiation/licensing DNA replication genes, the REV1 (p=0.0215), PolI (p=0.0018) and PolQ (p=0.0033) TLS DNA polymerases, the RAD51 (p=0.0001), SLX4 (p=0.0347) and BLM (p=0.0013) genes involved in the protection of stalled replication forks as well as the MCM8 (p=0.0418) DNA helicase (Table 4). When finally relapse-free survival of patients was investigated, we confirmed that except CYCLIN A and CDC25A (DDR), all these genes were again significantly related to the outcome of patients (p<0.05, Table S2). Conversely, the misexpression of the licensing MCM7 gene (p<0.0283) and the p300 histone acetyl transferase (p<0.0117) were associated with the relapse-free but not the disease-free survival rate.

TABLE 4

DNA replication genes associated with the patients' outcome

| DNA replication genes | Terciles ($\Delta$ Ct) | N | Overall survival | | | Disease-free survival | | | Relapse-free survival | | |
|---|---|---|---|---|---|---|---|---|---|---|---|
| | | | Events | % | P value (Log Rank) | Events | % | P value (Log Rank) | Events | % | P value (Log Rank) |
| CDC25A | [−1.06,1.36] | 31 | 4 | 12.9 | 0.0196 | 12 | 38.71 | 0.011 | 10 | 32.36 | 0.073 |
| | (1.36, 2.53] | 31 | 3 | 9.68 | | 11 | 35.48 | | 10 | 32.36 | |
| | (2.53, 4.73] | 31 | 12 | 38.71 | | 22 | 70.97 | | 17 | 54.84 | |
| CHK1 | [−0.0717, 1.61] | 31 | 3 | 9.68 | 0.0824 | 9 | 29.03 | 0.0003 | 8 | 25.81 | 0.0001 |
| | (1.61, 2.6] | 31 | 6 | 19.35 | | 15 | 48.39 | | 10 | 32.26 | |
| | (2.6, 4.78] | 31 | 10 | 32.26 | | 21 | 67.74 | | 19 | 61.29 | |
| CLASPIN | [−0.431, 1.74] | 31 | 1 | 3.23 | 0.0233 | 7 | 22.58 | 0.0005 | 6 | 19.35 | 0.0024 |
| | (1.74, 2.63] | 31 | 8 | 25.81 | | 17 | 54.84 | | 14 | 45.16 | |
| | (2.63, 4.99] | 31 | 10 | 32.26 | | 21 | 67.74 | | 17 | 54.84 | |
| RPA | [−1.3, −0.386] | 31 | 10 | 32.26 | 0.0458 | 18 | 58.06 | 0.1076 | 14 | 45.16 | 0.1421 |
| | (−0.386, 0.0473] | 31 | 2 | 6.45 | | 10 | 32.26 | | 8 | 25.81 | |
| | (0.0473, 1.09] | 31 | 7 | 22.58 | | 17 | 54.84 | | 15 | 48.39 | |
| SIRT1 | [−1.96, 0.811] | 31 | 9 | 29.03 | 0.3225 | 22 | 70.97 | 0.0056 | 19 | 61.29 | 0.0049 |
| | (−0.811, −0.394] | 31 | 4 | 12.9 | | 11 | 35.48 | | 8 | 25.81 | |
| | (−0.394, 1.12] | 31 | 6 | 19.35 | | 12 | 38.71 | | 10 | 32.26 | |
| TIMELESS | [−0.255, 0.774] | 31 | 3 | 9.68 | 0.0945 | 8 | 25.81 | 0.0127 | 7 | 22.58 | 0.0303 |
| | (0.774, 1.62] | 31 | 5 | 16.13 | | 17 | 54.84 | | 13 | 41.94 | |
| | (1.62, 2.77] | 31 | 11 | 35.48 | | 20 | 64.52 | | 17 | 54.84 | |
| 53BP1 | [−4.23, −1.53] | 31 | 7 | 22.58 | 0.6493 | 18 | 58.06 | 0.0339 | 15 | 48.39 | 0.0486 |
| | (−1.53, 0.836] | 31 | 7 | 22.58 | | 18 | 58.06 | | 15 | 48.39 | |
| | (−0.836, 2.79] | 31 | 5 | 16.13 | | 9 | 29.03 | | 7 | 22.58 | |
| MCM8 | [−2.18, 0.37] | 31 | 4 | 12.9 | 0.3283 | 15 | 48.39 | 0.0418 | 14 | 45.16 | 0.0164 |
| | (0.37, 1.07] | 31 | 6 | 19.3.5 | | 10 | 32.26 | | 6 | 19.35 | |
| | (1.07, 2.42] | 31 | 9 | 29.03 | | 20 | 64.52 | | 17 | 54.84 | |
| BLM | [−0.579, 1.02] | 31 | 5 | 16.13 | 0.1533 | 11 | 35.48 | 0.0013 | 8 | 25.81 | 0.003 |
| | (1.02, 1.72] | 31 | 4 | 12.9 | | 13 | 41.94 | | 10 | 32.26 | |
| | (1.72, 3.65] | 31 | 10 | 32.26 | | 21 | 67.74 | | 19 | 61.29 | |
| BRCA1 | [−1.11, 0.326] | 31 | 3 | 9.68 | 0.2815 | 9 | 29.03 | 0.0008 | 7 | 22.58 | 0.0003 |
| | (0.326, 1.14] | 31 | 7 | 22.58 | | 14 | 45.16 | | 10 | 32.26 | |
| | (1.14, 2.4] | 31 | 9 | 29.03 | | 22 | 70.97 | | 20 | 64.52 | |
| SLX4 | [−1.55, 0.0371] | 31 | 5 | 16.13 | 0.1065 | 16 | 51.61 | 0.0347 | 14 | 45.16 | 0.0256 |
| | (0.0371, 0.484] | 31 | 4 | 12.9 | | 10 | 32.26 | | 7 | 22.58 | |
| | (0.484, 2.37] | 31 | 10 | 32.26 | | 19 | 61.29 | | 16 | 51.61 | |
| P300 | [−2.1, −0.532] | 31 | 5 | 16.13 | 0.3838 | 21 | 67.74 | 0.0824 | 20 | 64.52 | 0.0117 |
| | (−0.532, −0.13] | 31 | 9 | 29.03 | | 12 | 38.71 | | 8 | 25.81 | |
| | (−0.13, 2.1] | 31 | 5 | 16.13 | | 12 | 38.71 | | 9 | 29.03 | |
| CYCLIN A | [−0.37, 1.94] | 31 | 2 | 6.45 | 0.0128 | 12 | 38.71 | 0.0166 | 11 | 35.48 | 0.0803 |
| | (1.94, 3.07] | 31 | 5 | 16.13 | | 12 | 38.71 | | 10 | 32.26 | |
| | (3.07, 5.85] | 31 | 12 | 38.71 | | 21 | 67.74 | | 16 | 51.61 | |
| CYCLIN E | [−0.849,1.32] | 31 | 4 | 12.9 | 0.3447 | 11 | 35.48 | 0.0405 | 8 | 25.81 | 0.0322 |
| | (1.32, 2.39] | 31 | 6 | 19.35 | | 14 | 45.16 | | 12 | 38.71 | |
| | (2.39, 6.27] | 31 | 9 | 29.03 | | 20 | 64.52 | | 17 | 54.84 | |
| CDC45 | [0.106, 2.28] | 31 | 4 | 12.9 | 0.4772 | 11 | 35.48 | 0.0025 | 10 | 32.26 | 0.0018 |
| | (2.28, 3.65] | 31 | 6 | 19.35 | | 12 | 38.71 | | 8 | 25.81 | |
| | (3.65,6.03] | 31 | 9 | 29.03 | | 22 | 70.97 | | 19 | 61.29 | |
| CDC6 | [−0.405, 2.18] | 31 | 2 | 6.45 | 0.0404 | 10 | 32.26 | 0.0103 | 9 | 29.03 | 0.0323 |
| | (2.18, 3.29] | 31 | 6 | 19.35 | | 14 | 45.16 | | 11 | 35.48 | |
| | (3.29, 4.89] | 31 | 11 | 35.48 | | 21 | 67.74 | | 17 | 54.84 | |
| CDT1 | [−1.12, 2.13] | 31 | 5 | 16.13 | 0.7449 | 8 | 25.81 | 0.0101 | 6 | 19.35 | 0.0123 |
| | (2.13, 3.33] | 31 | 5 | 16.13 | | 16 | 51.61 | | 13 | 41.94 | |
| | (3.33, 6.87] | 31 | 9 | 29.03 | | 21 | 67.74 | | 18 | 58.06 | |

TABLE 4-continued

DNA replication genes associated with the patients' outcome

| DNA replication genes | Terciles (Δ Ct) | N | Overall survival | | | Disease-free survival | | | Relapse-free survival | | |
|---|---|---|---|---|---|---|---|---|---|---|---|
| | | | Events | % | P value (Log Rank) | Events | % | P value (Log Rank) | Events | % | P value (Log Rank) |
| GEMININ | [−0.197, 0.803] | 31 | 3 | 9.68 | 0.0968 | 6 | 19.35 | <0.0005 | 5 | 16.13 | <0.0005 |
| | (0.803, 1.54] | 31 | 6 | 19.35 | | 17 | 54.84 | | 13 | 41.94 | |
| | (1.54, 3.57] | 31 | 10 | 32.26 | | 22 | 70.97 | | 19 | 61.29 | |
| MCM7 | [−0.712, 0.254] | 31 | 5 | 16.13 | 0.8746 | 13 | 41.94 | 0.0833 | 11 | 35.48 | 0.0283 |
| | (0.254, 0.963] | 31 | 6 | 19.35 | | 12 | 38.71 | | 8 | 25.81 | |
| | (0.963, 2.57] | 31 | 8 | 25.81 | | 20 | 64.51 | | 18 | 58.06 | |
| PLK1 | [−0.558, 2.65] | 31 | 2 | 6.45 | 0.0062 | 6 | 19.35 | 0.0001 | 5 | 16.13 | 0.001 |
| | (2.65, 3.82] | 31 | 5 | 16.13 | | 18 | 58.06 | | 16 | 51.61 | |
| | (3.82, 6.21] | 31 | 12 | 38.71 | | 21 | 67.74 | | 16 | 51.61 | |
| Ki67 | [−0.927, 2.22] | 31 | 3 | 9.68 | 0.143 | 6 | 19.35 | 0.0051 | 5 | 16.13 | 0.0214 |
| | (2.22, 3.33] | 31 | 5 | 16.13 | | 17 | 54.84 | | 15 | 48.38 | |
| | (3.33, 7.63] | 31 | 11 | 35.48 | | 22 | 70.97 | | 17 | 54.84 | |
| POLI | [−3.87, −1] | 31 | 8 | 25.81 | 0.27 | 22 | 70.97 | 0.0018 | 18 | 58.06 | 0.007 |
| | (−1, −0.403] | 31 | 7 | 22.58 | | 13 | 41.94 | | 10 | 32.26 | |
| | (−0.403, 0.866] | 31 | 4 | 12.9 | | 10 | 32.26 | | 9 | 29.03 | |
| POLQ | [−0.508, 1.75] | 31 | 2 | 6.45 | 0.0008 | 8 | 25.81 | 0.0033 | 7 | 22.58 | 0.0359 |
| | (1.75, 2.67] | 31 | 4 | 12.9 | | 17 | 54.84 | | 16 | 51.61 | |
| | (2.67, 6.44] | 31 | 13 | 41.94 | | 20 | 64.52 | | 14 | 45.16 | |
| REV1 | [−2.67, −1.01] | 31 | 6 | 19.35 | 0.2782 | 18 | 58.06 | 0.0215 | 16 | 51.61 | 0.0113 |
| | (−1.01, −0.392] | 31 | 9 | 29.03 | | 18 | 58.06 | | 15 | 48.39 | |
| | (−0.392, 1.59] | 31 | 4 | 12.9 | | 9 | 29.03 | | 6 | 19.35 | |
| POLL | [−3.23, −0.371] | 31 | 4 | 12.9 | 0.0464 | 16 | 51.61 | 0.3534 | 15 | 48.39 | 0.689 |
| | (−0.371, 0.049] | 31 | 4 | 12.9 | | 12 | 38.71 | | 11 | 35.48 | |
| | (0.049, 1.62] | 31 | 11 | 35.48 | | 17 | 54.84 | | 11 | 35.48 | |
| RAD51 | [−0.514, 1.3] | 31 | 4 | 12.9 | 0.007 | 9 | 29.03 | 0.0001 | 7 | 22.58 | 0.0009 |
| | (1.3, 2.15] | 31 | 3 | 9.68 | | 13 | 41.94 | | 12 | 38.71 | |
| | (2.15, 4.3] | 31 | 12 | 38.71 | | 23 | 74.19 | | 18 | 58.06 | |
| ERCC1 | [−2.07, −0.456] | 31 | 11 | 35.48 | 0.0256 | 20 | 64.52 | 0.0679 | 14 | 45.16 | 0.4487 |
| | (−0.456, −0.0618] | 31 | 4 | 12.9 | | 14 | 45.16 | | 13 | 41.94 | |
| | (−0.0618, 0.735] | 31 | 4 | 12.9 | | 11 | 35.48 | | 10 | 32.26 | |

Taken together, these data indicate (Table 5) that the expression of 5 genes i.e. CDC6, CLASPIN, PLK1, POLQ and RAD51 was associated at once to low overall, disease-free and relapse-free survivals. FIG. 1 shows the Kaplan-Meir curves of the overall survivals according to the level of these genes in the primary tumor. By using a Pearson test we investigated whether deregulation in a tumor of a given DNA replication gene from this cluster could be concomitant to that of another one from the same group. FIG. S2A indicates that expressions of these 5 genes are concomitant (rho>0.7), revealing a potential 5-gene DNA replication prognosis signature. A hierarchical ascending classification (FIG. S2B) confirmed this data for 4 genes out of 5 i.e. POLQ, PLK1, RAD51 and CDC6. CLASPIN expression also correlated even at a lesser extent, while CDC45, CYCLIN E, CYCLIN A and CDC25A (which are associated with two out of free measured survival features), were likely to be included in this "metamarker".

TABLE 5

Survival of patients according to the level of 3R gene expression

| Replication Genes | DNA transactions | Terciles T/N limits) | n | Overall survival | | | Disease-free survival | | | Relapse-free survival | | |
|---|---|---|---|---|---|---|---|---|---|---|---|---|
| | | | | Events | % | P value (Log Rank) | Events | % | P value (Log Rank) | Events | % | P value (Log Rank) |
| CLASPIN | DDR | (0.74, 3.27) | 31 | 1 | 3.23 | 0.02 | 7 | 22.58 | 0.0005 | 6 | 19.35 | 0.002 |
| | | (3.39, 6.15) | 31 | 8 | 25.81 | | 17 | 54.84 | | 14 | 45.16 | |
| | | (6.25, 31.81) | 31 | 10 | 32.26 | | 21 | 67.74 | | 17 | 54.84 | |
| RAD51 | DSB repair | (0.70, 2.40) | 31 | 4 | 12.9 | 0.007 | 9 | 29.03 | 0.0001 | 7 | 22.58 | 0.0009 |
| | | (2.48, 4.40) | 31 | 3 | 9.68 | | 13 | 41.94 | | 12 | 38.71 | |
| | | (4.46, 19.65) | 31 | 12 | 38.71 | | 23 | 74.19 | | 18 | 58.06 | |
| PLK1 | Initiation/ Licensing | (0.68, 6.28) | 31 | 2 | 6.45 | 0.006 | 6 | 19.35 | 0.0001 | 5 | 16.13 | 0.001 |
| | | (6.31, 14.12) | 31 | 5 | 16.13 | | 18 | 58.06 | | 16 | 51.61 | |
| | | (14.13, 74.19) | 31 | 12 | 38.71 | | 21 | 67.74 | | 16 | 51.61 | |
| POLQ | TLS | (0.70, 3.34) | 31 | 2 | 6.45 | 0.0008 | 8 | 25.81 | 0.003 | 7 | 22.58 | 0.04 |
| | | (3.36, 6.31) | 31 | 4 | 12.9 | | 17 | 54.84 | | 16 | 51.61 | |
| | | (6.42, 86.70) | 31 | 13 | 41.94 | | 20 | 64.52 | | 14 | 45.16 | |

TABLE 5-continued

Survival of patients according to the level of 3R gene expression

| Replication Genes | DNA transactions | Terciles T/N limits) | n | Overall survival | | | Disease-free survival | | | Relapse-free survival | | |
|---|---|---|---|---|---|---|---|---|---|---|---|---|
| | | | | Events | % | P value (Log Rank) | Events | % | P value (Log Rank) | Events | % | P value (Log Rank) |
| CDC6 | Initiation/Licensing | (0.75, 4.47) | 31 | 2 | 6.45 | 0.04 | 10 | 32.26 | 0.01 | 9 | 29.03 | 0.03 |
| | | (4.55, 9.62) | 31 | 6 | 19.35 | | 14 | 45.16 | | 11 | 35.48 | |
| | | (10.08, 29.65) | 31 | 11 | 35.48 | | 21 | 67.74 | | 17 | 54.84 | |

Finally we used a Cox multivariate regression model to further examine the relationship between survival distribution and the following covariates: age, sex, tumor stage as well as the expression of Ki67 and PCNA tumor proliferation clinical markers. Table 6 indicates that a close correlation between the overall survival of patients and the expression of CDC6, CLASPIN, PLK1, and POLQ still remained after adjusting the survival data by taking into account each potential confounder. Very interestingly, patients with tumors that strongly overexpress these four genes had a much higher risk of death i.e. a 36.3-fold (95% Cl 2.6-517.4 P=0.04), 23.49-fold (95% Cl 1.9-288.4 P=0.01), 18.50-fold (95% Cl 1.3-267.4 P=0.01) and 20.65-fold (95% Cl 1.5-275.9 P=0.05) increased risk, compared to patients who harbour tumors that present normal levels of those genes, respectively (Table 6). This prognostic effect was then independent on age, sex, treatment, stage classification and expression of proliferation markers.

The Prognosis Potential of the DNA Replication Markers Included in the 5-gene Cluster is Independent of Either Treatment or Node Status We finally used a log-rank test to further examine the dependence between survival distribution and either treatment (chemotherapy, chemotherapy plus radiotherapy or no adjuvant treatment) or node stages (N). This bi-varied analysis did not show any significant correlation (p>0.05, Table 7) between the expression of CDC6, CLASPIN, PLK1, POLQ, or RAD51 DNA replication genes from the identified DNA replication prognosis signature and the therapeutic strategy or the number of metastasis-containing nodes.

TABLE 6

Multivaried Cox regression analysis of the relationship between survival and DNA replication gene expression by taking into account age, sex, treatment (in 3 categories: none/chemotherapy/chemotherapy and radiotherapy), T classification (2 categories: T0 or T1/T2 or T3), KI67 and PCNA clinical markers.

| | T/N (terciles) | Overall survival | | | Disease-free survival | | | Relapse-free survival | | |
|---|---|---|---|---|---|---|---|---|---|---|
| | | HR | (95% CI) | P Value | HR | (95% CI) | P Value | HR | (95% CI) | P Value |
| POLQ | 0.70-3.34 (ref) | 1.00 | | 0.004 | 1.00 | | 0.67 | 1.00 | | 0.99 |
| | 3.36-6.31 | 4.59 | (0.56-37.69) | | 1.07 | (0.35-3.29) | | 0.93 | (0.27-3.15) | |
| | 6.42-86.70 | 36.31 | (2.55-517.38) | | 1.57 | (0.40-6.18) | | 0.94 | (0.20-4.41) | |
| PLK1 | 0.68-6.28 (ref) | 1.00 | | 0.01 | 1.00 | | 0.001 | 1.00 | | 0.007 |
| | 6.31-14.12 | 4.43 | (0.50-39.56) | | 3.10 | (0.78-12.32) | | 3.26 | (0.73-14.53) | |
| | 14.13-74.19 | 23.49 | (1.91-288.38) | | 11.14 | (2.35-52.75) | | 11.11 | (1.97-62.70) | |
| RAD51 | 0.70-2.40 (ref) | 1.00 | | 0.13 | 1.00 | | 0.02 | 1.00 | | 0.04 |
| | 2.48-4.40 | 0.72 | (0.11-4.74) | | 0.98 | (0.31-3.13) | | 1.08 | (0.30-3.98) | |
| | 4.46-19.65 | 2.94 | (0.51-16.84) | | 3.44 | (1.00-11.83) | | 4.00 | (0.96-16.68) | |
| CLASPIN | 0.74-3.27 (ref) | 1.00 | | 0.01 | 1.00 | | 0.007 | 1.00 | | 0.03 |
| | 3.39-6.15 | 18.44 | (1.52-223.05) | | 4.68 | (1.51-14.55) | | 4.23 | (1.23-14.56) | |
| | 6.25-31.81 | 18.50 | (1.28-267.42) | | 4.93 | (1.50-16.17) | | 4.73 | (1.30-17.25) | |
| CDC6 | 0.75-4.47 (ref) | 1.00 | | 0.05 | 1.00 | | 0.55 | 1.00 | | 0.42 |
| | 4.55-9.62 | 5.77 | (0.97-34.29) | | 1.25 | (0.44-3.56) | | 0.98 | (0.30-3.23) | |
| | 10.08-29.65 | 20.65 | (1.54-275.91) | | 2.25 | (0.46-10.92) | | 2.34 | (0.38-14.33) | |

TABLE 7

Bivaried analysis between the expression of replication genes and treatment or stages

| DNA replication gene [T/N terciles limits] | No adjuvant treatment (n = 46) | Radiotherapy plus chemotherapy (n = 11) | Only chemotherapy (n = 36) | P-value |
|---|---|---|---|---|
| CLASPIN, n (%) | | | | |
| [0.74, 3.27] | 18 (39.1) | 1 (9.1) | 12 (33.3) | 0.4340 |
| [3.39, 6.15] | 14 (30.4) | 5 (45.5) | 12 (33.3) | |
| [6.25, 31.81] | 14 (30.4) | 5 (45.5) | 12 (33.3) | |
| RAD51, n (%) | | | | |
| [0.70, 2.40] | 18 (39.1) | 2 (18.2) | 11 (30.6) | 0.6938 |
| [2.48, 4.40] | 15 (32.6) | 4 (36.4) | 12 (33.3) | |
| [4.46, 19.65] | 13 (28.3) | 5 (45.5) | 13 (36.1) | |
| PLK1, n (%) | | | | |
| [0.68, 6.28] | 19 (41.3) | 3 (27.3) | 9 (25.0) | 0.5136 |
| [6.31, 14.12] | 12 (26.1) | 4 (36.4) | 15 (41.7) | |
| [14.13, 74.19] | 15 (32.6) | 4 (36.4) | 12 (33.3) | |
| POLQ, n (%) | | | | |
| [0.70, 3.34] | 20 (43.5) | 2 (18.2) | 9 (25.0) | 0.3480 |
| [3.36, 6.31] | 13 (28.3) | 4 (36.4) | 14 (38.9) | |
| [6.42, 86.70] | 13 (28.3) | 5 (45.5) | 13 (36.1) | |
| CDC6, n (%) | | | | |
| [0.75, 4.47] | 19 (41.3) | 4 (36.4) | 8 (22.2) | 0.2733 |
| [4.55, 9.62] | 16 (34.8) | 3 (27.3) | 12 (33.3) | |
| [10.08, 29.65] | 11 (23.9) | 4 (36.4) | 16 (44.4) | |

| DNA replication gene | Stage N0 (n = 61) | Stage N1 (n = 11) | Stages N2-N3 (n = 21) | P value |
|---|---|---|---|---|
| CLASPIN, n (%) | | | | |
| [0.74, 3.27] | 23 (37.7) | 4 (36.4) | 4 (19.0) | 0.4287 |
| [3.39, 6.15] | 20 (32.8) | 2 (18.2) | 9 (42.9) | |
| [6.25, 31.81] | 18 (29.5) | 5 (45.5) | 8 (38.1) | |
| RAD51, n (%) | | | | |
| [0.70, 2.40] | 24 (39.3) | 2 (18.2) | 5 (23.8) | 0.5345 |
| [2.48, 4.40] | 19 (31.1) | 4 (36.4) | 8 (38.1) | |
| [4.46, 19.65] | 18 (29.5) | 5 (45.5) | 8 (38.1) | |
| PLK1, n (%) | | | | |
| [0.68, 6.28] | 22 (36.1) | 4 (36.4) | 5 (23.8) | 0.6641 |
| [6.31, 14.12] | 18 (29.5) | 3 (27.3) | 10 (47.6) | |
| [14.13, 74.19] | 21 (34.4) | 4 (36.4) | 6 (28.6) | |
| POLQ, n (%) | | | | |
| [0.70, 3.34] | 22 (36.1) | 5 (45.5) | 4 (19.0) | 0.4682 |
| [3.36, 6.31] | 20 (32.8) | 2 (18.2) | 9 (42.9) | |
| [6.42, 86.70] | 19 (31.2) | 4 (36.4) | 8 (38.1) | |
| CDC6, n (%) | | | | |
| [0.75, 4.47] | 20 (32.8) | 4 (36.4) | 7 (33.3) | 1.0000 |
| [4.55, 9.62] | 21 (32.4) | 3 (27.3) | 7 (33.3) | |
| [10.08, 29.65] | 20 (32.8) | 4 (36.4) | 7 (33.3) | |

In contrast the level of other DNA replication genes such as CDC25B (p=0.0307), GEMININ (p=0.0263) and the control APC (p=0.0404) on one hand, and CDC25B (p=0.0344), SLX4 (p=0.0466), GEMININ (p=0.0192) and MCM7 (p=0.0364) on the other, were associated with anti-cancer treatment and clinical classification, respectively (Table 8).

TABLE 8

Bivaried analysis between the expression of replication genes and treatment or stages.

| DNA replication genes [T/N tercile limits] | No adjuvant treatment (n = 46) | Radiotherapy plus chemotherapy (n = 11) | Only chemotherapy (n = 36) | P-value |
|---|---|---|---|---|
| CDC25B, n (%) | | | | |
| [0.25, 0.61] | 21 (45.7) | 2 (18.2) | 8 (22.2) | 0.0307 |
| [0.66, 1.32] | 15 (32.6) | 6 (54.5) | 10 (27.8) | |
| [1.34, 6.48] | 10 (21.7) | 3 (27.3) | 18 (50.0) | |
| GEMININ, n (%) | | | | |
| [0.87, 1.72] | 21 (45.7) | 0 (0) | 10 (27.8) | 0.0263 |
| [1.76, 2.90] | 11 (23.9) | 6 (54.5) | 14 (38.9) | |
| [2.93, 11.92] | 14 (30.4) | 5 (45.5) | 12 (33.3) | |
| APC, n (%) | | | | |
| [0.13, 0.39] | 11 (23.9) | 5 (45.5) | 15 (41.7) | 0.0404 |
| [0.39, 0.53] | 22 (47.8) | 3 (27.3) | 6 (16.7) | |
| [0.53, 0.95] | 13 (28.3) | 3 (27.3) | 15 (41.7) | |

| DNA replication gene | Stage N0 (n = 61) | Stage N1 (n = 11) | Stages N2-N3 (n = 21) | P value |
|---|---|---|---|---|
| CDC25B, n (%) | | | | |
| [0.25, 0.61] | 25 (41.0) | 1 (9.1) | 5 (23.8) | 0.0344 |
| [0.66, 1.32] | 19 (31.1) | 2 (18.2) | 10 (47.6) | |
| [1.34, 6.48] | 17 (27.9) | 8 (72.7) | 6 (28.6) | |
| SLX4, n (%) | | | | |
| [0.34, 1.02] | 20 (32.8) | 5 (45.5) | 6 (28.6) | 0.0466 |
| [1.03, 1.39] | 23 (37.7) | 5 (45.5) | 3 (14.3) | |
| [1.41, 5.17] | 18 (29.5) | 1 (9.1) | 12 (57.1) | |
| GEMININ, n (%) | | | | |
| [0.87, 1.72] | 27 (44.3) | 2 (18.2) | 2 (9.5) | 0.0192 |
| [1.76, 2.90] | 15 (24.6) | 5 (45.5) | 11 (52.4) | |
| [2.93, 11.92] | 19 (31.1) | 4 (36.4) | 8 (38.1) | |
| MCM7, n (%) | | | | |
| [0.61, 1.18] | 18 (29.5) | 5 (45.5) | 8 (38.1) | 0.0364 |
| [1.20, 1.94] | 26 (42.6) | 0 (0.0) | 5 (23.8) | |
| [1.97, 5.95] | 17 (27.9) | 6 (54.6) | 8 (38.1) | |

In this study, we report that over-expression of CDC6, CLASPIN, PLK1, POLQ and RAD51 genes was associated to survival of patients, whatever the means this survival was measured. Since oncogene deregulation has been shown to modify the replicative program, thus inducing DNA damage during S phase and creating genetic instability in the absence of functional checkpoints (1), these data suggest that this deregulation could affect different and non-redundant DNA metabolism pathways such as replicative bypass of DNA lesions (POLQ), DNA repair of post-replicative DNA breaks (RAD51), maintenance of stalled DNA replication forks (CLASPIN), DNA replication/mitosis connexion (PLK1) as well as the firing of replication origins (CDC6, PLK1). Therefore DNA hyper-replication (increased firing and DNA elongation) induces more DNA damage that might lead to genetic instability in the absence of functional S-phase checkpoint or DNA repair pathways, as observed in our cohort. Alongside the identification of individual markers, our work thus identifies that subsets of "DNA replication" genes as useful cancer prognostic "metamarkers".

REFERENCES

1. Bartkova, J., et al. (2006) Oncogene-induced senescence is part of the tumorigenesis barrier imposed by DNA damage checkpoints. *Nature* 444: 633-637.
2. Bertwistle, D. & Ashworth, A. (1998) Functions of the BRCA1 and BCRA2 genes *Curr. Opin. Genet. Dev.* 8: 14-20.
3. Marra, G. & Boland, C. R. (1995) Hereditary nonpolyposis colorectal cancer (HNPCC): the syndrome, the genes and historical perspectives. *J. Nat. Cancer Inst.* 87: 1114-1125.
4. Sancar, A. (1994) Mechanisms of DNA excision repair *Science* 266: 1954-1956.
5. Masutani, C., et al. (1999) The XPV (xeroderma pigmentosum variant) gene encodes human DNA polymerase eta. *Nature* 399: 700-704.
6. Kunkel, T. A. (2003) Considering the cancer consequences of altered DNA polymerase function. *Cancer Cell* 3: 105-110.
7. Mitchell, J. R., Hoeijmakers, J. H. & Niedernhofer, L. J. (2003) Divide and conquer: nucleotide excision repair battles cancer and ageing. *Curr. Opin. Cell Biol.* 15: 232-240.
8. Venkatesan, R. N., et al. (2007) Mutation at the polymerase active site of mouse DNA polymerase delta increases genomic instability and accelerates tumorigenesis. *Mol Cell Biol* 27: 7669-7682.
9. Arentson, E., et al. (2002) Oncogenic potential of the DNA replication licensing protein Cdt1 *Oncogene* 21: 1150-1158.

10. Honeycutt, K. A., et al. (2006) Deregulated minichromosomal maintenance protein MCM7 contributes to oncogene driven tumorigenesis. *Oncogene* 25: 4027-4032.
11. Fong, K., Zimmerman, P.& Smith, P. (1995) Tumor progression and loss of heterozygosity at 5 q and 18 q in non-small cell lung cancer. *Cancer Res* 55: 220-223.
12. Esposito, V., et al. (1997) Prognostic value of p53 in non-small cell lung cancer: relationship with proliferating cell nuclear antigen and cigarette smoking. *Hum Pathol* 28: 233-237.
13. Zheng, Z., et al. (2007) DNA synthesis and repair genes RRM1 and ERCC1 in Lung Cancer *The New England J Medecine* 356: 800-808.
14. Pillaire, M. J., et al. (2010) A 'DNA replication' signature of progression and negative outcome in colorectal cancer. *Oncogene* 29: 816-887.
15. Kahli, M., et al. (2011) A direct role of HMGA proteins in changes occuring in the replication program during senescence Submitted.
16. Thomae, A., et al. (2008) Interaction between HMGA1a and the origin recognition complex creates site-specific replication origins. *Proc Natl Acad Sci USA* 105: 1692-1697.
17. MacAlpine, H., Gordan, R., Powell, S., Hartemink, A.& MacAlpine, D. (2010) Drosophila ORC localizes to open chromatin and marks sites of cohesin complex loading. Genome Research 20: 201-211.
18. Lemee, F., et al. (2010) DNA polymerase theta is associated with poor survival in breast cancer, perturbs DNA replication, and promotes genetic instability *Proc Natl Acad Sci USA* 107: 13390-13395.
19. Sobol, R. W., et al. (1996) Requirement of mammalian DNA polymerase-beta in base-excision repair *Nature* 379: 183-6.
20. Capp, J. P., et al. (2007) Involvement of DNA polymerase mu in the repair of a specific subset of DNA double strand breaks in mammalian cells *Nucl. Acids Res.* 35: 3551-3560.
21. Lin, J., Zeman, M., Chen, J., Yee, M.& Cimprich, K. (2011) SHPRH and HLTF act in a damage-specific manner to coordinate different forms of postreplication repair and prevent mutagenesis. *Mol Cell* 42: 237-249.
22. Maiorano, D., Cuvier, 0., Danis, E.& Mechali, M. (2005) MCM8 is an MCM2-7-related protein that functions as a DNA helicase during replication elongation and not initiation. *Cell* 120: 315-328.
23. Lutzmann, M. & Mechali, M. (2008) MCM9 binds Cdt1 and is required for the assembly of pre-replication complexes *Mol Cell* 31: 190-200.
24. Minard, L., Lin, L & Schultz, M. (2011) SWI/SNF and Asf1 Independently Promote Derepression of the DNA Damage Response Genes under Conditions of Replication Stress. *PLoS One* 6(6): e21633.
25. Hayakawa, T., et al. (2010) MRG15 binds directly to PALB2 and stimulates homology-directed repair of chromosomal breaks. *J Cell Sci* 123: 1124-1130.
26. Mao, Z., et al. (2011) SIRT6 promotes DNA repair under stress by activating PARP1. *Science* 332: 1443-1446.
27. He, H., Yu, F., Sun, C. & Luo, Y. (2011) CBP/p300 and SIRT1 are involved in transcriptional regulation of S-phase specific histone genes *PLoS One* 6: e22088.
28. Yim, H.& Erikson, R. (2011) Regulation of the final stage of mitosis by components of the pre-replicative complex and a polo kinase *Cell Cycle* 10: 1374-1377.
29. (2006) DNA replication and human disease (Inglis J, Cold Spring Harbor).
30. Glover, T., Arlt, M., Casper, A.& Durkin, S. (2005) Mechanisms of common fragile site instability. *Hum Mol Genet* 15: 197-205.
31. Rey, L., et al. (2009) Human DNA polymerase eta is required for common fragile site stability during unperturbed DNA replication *Mol Cell Biol* 29: 3344-3354.
32. Courbet, S., et al. (2008) Replication fork movement sets chromatin loop size and origin choice in mammalian cells. *Nature* 455: 557-560.
33. Hoffmann, J. & Cazaux, C. (2010) Aberrant expression of alternative DNA polymerases: a source of mutator phenotype as well as replicative stress in cancer. *Semin Cancer Biol* 20: 312-319.
34. Kawamura, K., et al. (2004) DNA polymerase theta is preferentially expressed in lymphoid tissues and up-regulated in human cancers. *Int. J. Cancer* 109: 9-16.
35. Seki, M., et al. (2004) High-efficiency bypass of DNA damage by human DNA polymerase Q. *EMBO J.* 23: 4484-4494.

The invention claimed is:

1. A method for diagnosing and treating aggressiveness of a lung cancer in a patient, comprising the steps of:
    a) detecting from a biological sample of said patient an expression profile of one or more DNA replication stress gene signature, wherein said one or more DNA replication stress gene signature is selected from the group consisting of CDC6, CLASPIN, PLK1, POLQ and RAD51 genes,
        wherein at least one DNA replication stress gene signature is the CLASPIN gene;
    b) comparing the expression profile of step a) with at least one reference expression profile,
    c) diagnosing aggressiveness of the lung cancer by overexpression of the one or more DNA replication stress gene signature in the biological sample compared with at least one reference expression profile; and
    d) administering a chemotherapeutic agent to treat the patient diagnosed with aggressive lung cancer, wherein the chemotherapeutic agent is at least one cytotoxic agent selected from the group consisting of an inhibitor of DNA repair, DNA replication/damage checkpoint and DNA replication licensing/initiation.

2. The method according to claim 1, wherein the detection of the expression profile according to step a) is performed by measuring the expression level of each of said DNA replication stress gene signature.

3. The method according to claim 1, wherein the said reference expression profile is obtained by measuring the expression level of each of the genes of the said signature in a reference sample.

4. The method of claim 3, wherein the said reference expression sample is a healthy lung tissue sample from the said patient.

5. The method according to claim 1, wherein the comparison of step b) is performed by calculating an expression level ratio between the expression level in the test biological sample and the expression level in the reference sample for each of the genes of the signature.

6. The method according to claim 1, wherein the diagnosis is obtained by calculating an expression level ratio between the expression level in the biological sample and the expression level in the at least one reference sample, and comparing the obtained expression level ratio to a corresponding threshold value.

7. The method according to claim 1, comprising a step of normalizing the expression level of each gene of the said signature to the expression level of a control gene.

8. The method of claim 7, wherein said control gene is a housekeeping gene.

9. The method of claim 8, wherein said housekeeping gene is a gene selected in the group consisting of B2M, TFRC, YWHAZ, RPLO, 18S, GUSB, UBC, TBP, GAPDH, PPIA, POLR2A, ACTB, PGK1, HPRT1, IPO8 and HMBS.

10. The method of claim 9, wherein said gene is selected from the group consisting of IPO8, HMBS, GUSB, and UBC.

11. The method according to claim 1, wherein said expression level is measured at the mRNA level.

12. The method of claim 11, wherein said expression level is measured using quantitative PCR or microarray technology.

13. The method according to claim 1, wherein said expression level is measured at the protein level.

14. The method of claim 13, wherein said expression level is measured using specific antibodies.

* * * * *

SEQUENCE LISTING

```
<160> NUMBER OF SEQ ID NOS: 10

<210> SEQ ID NO 1
<211> LENGTH: 8787
<212> TYPE: DNA
<213> ORGANISM: homo sapiens
<220> FEATURE:
<221> NAME/KEY: misc_feature
<223> OTHER INFORMATION: POLQ gene

<400> SEQUENCE: 1
gggcgggccg ggaggtttga gtttgaagac tggcgggaag atgtccgcag ctgttgccag      60
gccagggttc tcccgagagg gaggacgctg ggactgtggc ttgccctgat cggccgagaa     120
gagtttgcca tgaatcttct gcgtcggagt gggaaacggc ggcgttcaga atcaggctca     180
gattcgttct cgggaagcgg cggtgacagc agtgccagcc cccagttcct ctccgggtcc     240
gtgctgagcc cgccgcccgg ccttggtcgc tgcctgaagg ccgcagctgc aggagaatgc     300
aagcctacag ttcctgacta cgaaagagac aagctactat tggcaaactg gggacttcct     360
```

```
aaagcagttc tggaaaaata ccacagtttt ggtgtaaaaa agatgtttga atggcaggca    420
gagtgccttt tgcttggaca agtcctggaa ggaaagaatt tagtttattc agctcctaca    480
agtgctggga agactcttgt ggcagaatta cttattttga agcgggtttt ggaaatgcgg    540
aagaaagctt tgtttattct tccctttgtt tctgtggcta aagagaagaa atactacctc    600
cagagtctgt ttcaggaagt aggaataaaa gtagacggtt atatgggcag cacctctcca    660
tcaaggcatt tctcttcatt ggatattgca gtctgcacaa ttgagagagc caatggtctg    720
atcaatcgcc tcatagagga aaataagatg gatctgttag aatggtggt tgtggatgaa     780 ttacatatgc tgggagactc tcaccgaggg tatctgctgg aacttttgct gaccaagatt    840
tgctatatta ctcggaaatc agcatcttgt caggcagatc tagccagttc tctgtctaat    900
gctgtgcaaa tcgttggcat gagtgctacc cttcctaatt tggagcttgt ggcttcctgg    960
ttgaatgctg aactctacca taccgacttt cgccctgtac cgcttttgga gtcagtaaaa   1020
gttggaaatt ccatatatga ctcttcaatg aaacttgtga gggaatttga gcccatgcta   1080
caagtgaagg gagatgagga ccatgttgtt agtttatgtt atgagacgat tgtgataac    1140 cattcagtat tacttttttg tccatcaaag aaatggtgtg agaagctggc agatatcatt   1200
gctcgagagt tttataatct acatcatcaa gctgagggat tggtgaaacc ctctgaatgc   1260
ccaccagtaa ttctggaaca aaaagaactc ctggaagtga tggatcagtt aagacgtttg   1320
ccttcaggac tggactctgt attacagaaa actgtaccat ggggagtagc atttcatcat   1380
gcaggtctta cttttgagga gagggatatc attgaaggag cctttcgtca aggtctcatt   1440
cgggtcttgg cggcaacttc tactctttct tctggggtga atttacctgc acgtcgtgtg   1500
attattcgaa cccctatttt tggtggtcga cctctagata ttcttactta taagcagatg   1560
gttggccgtg ctggcaggaa aggagtggac acagtaggcg agagtatctt aatttgtaag   1620
aactctgaga atcaaaagg catagctctc cttcagggtt ctctaaagcc tgttcgcagc    1680
tgtctgcaaa gacgagaagg agaagaagta actggcagca tgatacgagc tattctggag   1740
ataatagttg gtggagtggc aagtacatca caagatatgc atacttatgc tgcctgcaca   1800 ttttggctg caagtatgaa agaagggaag caaggaattc agagaaatca agagtctgtt    1860
cagcttggag cgattgaggc ctgtgtgatg tggctactag aaaatgaatt catccagagt   1920
acagaagcca gtgatggaac agaaggaaag gtgtatcatc aaacacatct ggttcggcc    1980 actctttctt cttcactttc tccagctgat actttagata ttttgctga cctgcaaaga    2040 gcaatgaagg gctttgtttt agagaatgat cttcatattc tctatctggt tacacctatg   2100
tttgaggatt ggactactat tgattggtat cgattttct gtttatggga agttgcca     2160 acttcaatga aaagggtggc agagctagtg ggagttgaag aggggttctt ggcccgttgt   2220
gtgaaaggaa aagtagtagc cagaactgag agacagcatc gacaaatggc catccataaa   2280
aggtttttca ccagtcttgt gctattagat ttaatcagtg aagttccctt aagggaaata   2340
aatcagaaat atggatgcaa tcgtgggcag attcaatctt gcaacagtc agctgctgtt    2400 tatgcaggga tgattacagt attttccaac cgtctgggct ggcacaacat ggaactacta   2460 cttttcccaat ttcagaagcg tcttacgttt ggcatccaga gggagctgtg tgacctggtt   2520
cgggtatcct tactaaatgc tcagagagcc agggttctct atgcttctgg ctttcatact   2580
gtggcagacc ttgctagagc aaaatattgt gaggtgagg tgattctgaa aaatgctgtg    2640
cctttcaaaa gtgcccggaa ggcagtggat gaggaagagg aagcagttga agaacgtcgc   2700
```

```
aatatgcgaa ctatctgggt gactggcaga aaaggtttaa ctgaaaggga agcagcagcc    2760
cttatagtgg aagaagccag aatgattctg cagcaggact tagttgaaat gggagtgcaa    2820
tggaatccat gtgccctgtt acattctagt acatgctcat tgactcatag tgagtccgaa    2880
gtaaaggaac acacatttat atcccaaact aagagttctt ataaaaaatt aacatcaaag    2940
aacaaaagta acacaatatt tagtgattct tatattaagc attcaccaaa tatagtgcaa    3000
gacttaaata aaagtagaga gcatacaagt tcctttaatt gtaatttcca gaatgggaat    3060
caagaacatc agacatgttc cattttcaga gcaagaaaac gggcctcttt agatataaat    3120
aaagagaagc caggagcctc tcagaatgag gggaaaacaa gtgataagaa agttgttcag    3180 acttttcac agaaaacaaa aaaggcacct ttgaatttca attcagaaaa gatgagcaga    3240
agttttcgat cttggaaacg tagaaagcat ctaaagcgat ctaggacag cagcccctg    3300 aaagactctg gagcgtgtag aatccattta caaggacaga ctctgtctaa tcctagtctt    3360
tgtgaagacc cgtttacctt agatgagaag aaaacggaat ttagaaattc agggccattt    3420
gctaaaaatg tatctttgag tggtaaggaa aaagataata aacatcatt cccattacaa     3480 ataaagcaaa attgttcatg aacataaca ctaactaatg ataattttgt ggagcatatt    3540
gtcacaggat ctcagagtaa aaatgtgact tgtcaggcca ctagtgtggt tagtgaaaag    3600
ggcagaggag tagctgttga ggcagaaaaa ataaatgaag tgctgataca aaatggttca    3660
aaaaaccaga atgtttatat gaaacaccat gacatccatc caattaacca gtacctgcga    3720
aagcaatctc atgaacagac aagcactatt accaaacaga aaaatataat agagagacaa    3780
atgccctgtg aagcagtcag tagttacata aatagagact caaatgttac tatcaattgt    3840
gaaaggataa agcttaatac agaggaaaat aaaccaagtc attttcaggc attaggagat    3900
gatataagca gaactgtgat acccagtgaa gtacttccat cagctggagc atttagcaaa    3960
tcagaaggcc agcatgagaa ttttctaaat atttctagac tacaagaaaa aacaggtact    4020
tatacaacaa acaaaactaa aaataatcat gtttctgact taggtttagt cctctgtgat    4080
tttgaagata gtttctatct ggatactcag tcagagaaaa taatacaaca gatggcaact    4140
gaaaatgcca aactaggagc aaaggacacc aacctggcag cagggataat gcagaagagc    4200
ttagtccaac agaactcaat gaactctttt cagaaggagt gtcacattcc ttttcctgct    4260
gaacagcacc ctctaggagc gactaagata gatcatttgg accttaagac tgtaggtact    4320
atgaaacaaa gcagtgattc acatggggtt gatatcctga ctccagaaag cccgattttc    4380
cattctccaa tactattgga ggaaaatggt ctttttttaa aaagaatga agtttctgtt    4440 actgattcac aattaaatag ttttcttcaa ggttatcaaa cacaagaaac tgtgaaacca    4500
gttatacttc tgattcctca aaagagaact cccactggtg tagaaggaga atgtcttcca    4560
gttcctgaaa caagtttgaa tatgagtgat agtttactat tgatagctt cagtgatgac    4620 tatctagtaa agaacaatt acctgatatg caaatgaaag aacccttcc ttcagaagta     4680 acatcaaacc attttagtga ttctctgtgt ctacaagaag acctaattaa aaaatcaaat    4740
gtaaatgaga atcaagatac ccaccagcag ttgacttgtt ccaatgatga atctattata    4800
ttttcagaaa tggattctgt tcagatggtt gaagctttgg acaatgtgga tatatttcct    4860
gtccaagaga agaatcatac tgtagtatct cctagagcat tagaactaag tgatccagta    4920
cttgatgagc accaccaagg tgatcaagat ggaggagatc aagatgaaag ggctgaaaaa    4980
tcaaaattaa ctgggaccag gcaaaatcat tcattcatat ggtcagggc atcatttgat    5040 ctaagtccag gactgcaaag gattttagat aaagtatcca gtcctctaga aaatgaaaag    5100
```

```
ctaaaatcaa tgactataaa cttttccagt ttgaatagaa aaaatacaga gttaaatgaa    5160
gaacaagaag ttatttcaaa cttggagaca aaacaagtgc agggaatttc attttcttct    5220
aataatgaag taaaaagcaa gattgagatg ctagaaaaca atgccaatca tgatgaaacc    5280
tcatccctct tacctcgtaa agaaagtaat atagttgatg ataatggtct cattcctcct    5340
acacccattc caacatctgc ttctaagctg acatttccag ggattcttga aacacctgta    5400
aacccttgga aaactaataa tgttttacaa cctggtgaaa gttatttatt tggctcacct    5460
tcagatatta aaaaccacga tttaagtcca gggagtagaa atgggttcaa agacaacagc    5520
cctattagtg acacaagctt ttcacttcag ttatcacagg atggattaca gttaactcca    5580
gcctcaagca gttcagaaag tttgtccata attgatgtag caagtgacca aaatctttc    5640 caaacattca ttaaggagtg gcggtgcaaa aagcgatttt ccatctcact ggcttgtgaa    5700
aagattagaa gtttgacatc ttctaaaact gctactattg gcagtaggtt taagcaagct    5760
agctcacctc aggaaattcc tattagagat gatggatttc ccattaaagg ttgtgatgac    5820
accttggtgg ttgactggc agtatgctgg ggtggaaggg atgcctatta ttttcactg    5880 cagaaggaac aaaagcattc tgaaattagt gccagtttgg ttccaccttc tttagatcca    5940
agcctgactt tgaaagacag gatgtggtac cttcaatctt gcttgcgaaa ggaatctgat    6000
aaagaatgtt ctgttgtcat ctatgacttc atccagagct ataaaattct tcttctttct    6060
tgtggcatct ccttggagca agttatgaa atcctaagg tggcatgctg ttactagat    6120 ccagattctc aggagccgac tcttcatagc atagttacca gttttcttcc tcatgagctt    6180
ccactcctag aagggatgga gaccagccaa gggattcaaa gcctggggct aaatgctggc    6240
agtgagcatt ctgggcgata cagagcatct gtggagtcca ttctcatctt caactctatg    6300
aatcagctca actctttgtt gcagaaggaa aaccttcaag atgttttccg taaggtggaa    6360
atgccctctc agtactgctt ggccttgcta gaactaaatg gaattggctt tagtactgca    6420
gaatgtgaaa gtcagaaaca tataatgcaa gccaagctgg atgcaattga gacccaggcc    6480
tatcaactag ctggccacag ttttctcttc accagttcag atgacatcgc tgaggtttta    6540
tttttggaat tgaagttgcc cccaaataga gagatgaaaa accaaggcag caagaaaact    6600
ctgggttcta ccagaagagg gattgacaat ggacgcaagc taaggctggg aagacagttc    6660
agcactagta aggacgtttt aaataaatta aaggcattac atcctttacc aggcttgata    6720
ttagaatgga gaagaatcac taatgctatt accaaagtgg tctttcccct tcagcgggaa    6780
aagtgtctta atccttttct tggaatggaa agaatctatc ctgtatcaca gtcgcacact    6840
gctacaggac gaataacctt tacagaacca atattcaga atgtgccaag agattttgaa    6900
atcaaaatgc caacactagt aggagaaagc ccaccttctc aagctgtagg caaaggccta    6960
cttcccatgg gcagaggaaa atataagaag ggtttcagcg tgaatcctag atgccaggca    7020
cagatggagg agagagctgc agacagagga atgccatttt caattagcat gcgacatgcc    7080
tttgtgcctt tcccaggtgg ttcaatactg gctgctgact actctcagct tgaactgagg    7140
atcttggctc atttatccca tgatcgtcgt ctcattcaag tgttaaacac tggagctgat    7200
gttttcagga gcattgcagc agagtggaag atgattgagc agagtctgt tggggatgat    7260 ctgaggcagc aggcaaaaca gatttgctat gggatcattt atggaatggg agctaaatct    7320
ttgggagagc agatgggcat taagaaaaat gatgctgcat gctatattga ctccttcaaa    7380
tccagataca cagggattaa tcaattcatg acagagacag tgaagaattg taaaagagac    7440
```

```
ggatttgttc agaccatttt gggaaggcgt agatatttgc caggaatcaa agacaacaac    7500
ccttatcgta aagctcacgc tgagcgtcaa gctatcaaca caatagtcca aggatcagca    7560
gctgatattg tcaaaatagc cacagttaac attcagaagc aattagagac cttccactca    7620
accttcaaat cccatggtca tcgagagggt atgctccaaa gtgaccaaac aggattgtca    7680
cgaaagagaa aactgcaagg gatgttctgc ccaatcagag gaggcttctt catccttcaa    7740
ctccatgatg aactcctata tgaagtggca gaagaagatg ttgttcaggt agctcagatt    7800
gtcaagaatg aaatggaaag tgctgtaaaa ctgtctgtga aattgaaagt gaaagtgaaa    7860
ataggcgcca gctggggaga gctaaaggac tttgatgtgt aactgtgctg ttgatgaagt    7920
cctcccaggg aagcctgtgc agatgcagtc acctggaaag aacagagatt acccttcac     7980 ctacctcagc aaaacaaact ttcaagtctt gatagactta gcctagtaat tttatagtga    8040
gagtttcaaa ctatatatca gtgtctatag catcaaaaac ttctggggc gtggggaag     8100 tagaatacca agtataatag ttacattcac tttcaaagag catctatgaa tttgcctttt    8160
gtaacttact gtggctttaa acatattcag aacagatgct tgaaatatgc acttagcact    8220
ttggttccac atctgtctgg gtaaaccatg aagaaaatga agctgctgcc tcaatcgacc    8280
cagacagcag ccataggcag ataaagattt ggtttcaccc tggtggtggt aggcatcgtg    8340
tgtgactttt tttcctctaa tatcaatttt acagtacgga aatagtattt taaaatagta    8400
ttggctaata aattatgaat tctataaagt agtaagactt ggtatggttg gagtgtagga    8460
atgaatattc atgaaatgtt tcttattgct tttccttccc taattcatac aatgaatgta    8520
tttggaatac ttcatatatta taaaataaac tatacctctt caagaggtat cctgttctgt    8580
aagatcagat gtttttattg caggtcaata taatactgcc agagacagaa aatacccct     8640 tatcagtccc ttagtgcctc tttctgtttg tggcatggtg agaaaaccca tgctgaaaag    8700
attgtacttt gtgatcccaa tcagagggat ggagctaatc tttttgctgt tgaaataaaa    8760
tgaatttatg agaaacttta aaaaaaa                                        8787
```

<210> SEQ ID NO 2
<211> LENGTH: 2590
<212> TYPE: PRT
<213> ORGANISM: homo sapiens
<220> FEATURE:
<221> NAME/KEY: misc_feature
<223> OTHER INFORMATION: POLQ protein

<400> SEQUENCE: 2

```
Met Asn Leu Leu Arg Arg Ser Gly Lys Arg Arg Ser Glu Ser Gly
1               5                   10                  15

Ser Asp Ser Phe Ser Gly Ser Gly Gly Asp Ser Ser Ala Ser Pro Gln
                20                  25                  30

Phe Leu Ser Gly Ser Val Leu Ser Pro Pro Gly Leu Gly Arg Cys
        35                  40                  45

Leu Lys Ala Ala Ala Ala Gly Glu Cys Lys Pro Thr Val Pro Asp Tyr
    50                  55                  60

Glu Arg Asp Lys Leu Leu Leu Ala Asn Trp Gly Leu Pro Lys Ala Val
65                  70                  75                  80

Leu Glu Lys Tyr His Ser Phe Gly Val Lys Lys Met Phe Glu Trp Gln
                85                  90                  95

Ala Glu Cys Leu Leu Leu Gly Gln Val Leu Glu Gly Lys Asn Leu Val
            100                 105                 110

Tyr Ser Ala Pro Thr Ser Ala Gly Lys Thr Leu Val Ala Glu Leu Leu
```

```
            115                 120                 125
Ile Leu Lys Arg Val Leu Glu Met Arg Lys Lys Ala Leu Phe Ile Leu
            130                 135                 140
Pro Phe Val Ser Val Ala Lys Glu Lys Lys Tyr Tyr Leu Gln Ser Leu
145                 150                 155                 160
Phe Gln Glu Val Gly Ile Lys Val Asp Gly Tyr Met Gly Ser Thr Ser
                    165                 170                 175
Pro Ser Arg His Phe Ser Ser Leu Asp Ile Ala Val Cys Thr Ile Glu
                180                 185                 190
Arg Ala Asn Gly Leu Ile Asn Arg Leu Ile Glu Glu Asn Lys Met Asp
            195                 200                 205
Leu Leu Gly Met Val Val Asp Glu Leu His Met Leu Gly Asp Ser
210                 215                 220
His Arg Gly Tyr Leu Leu Glu Leu Leu Leu Thr Lys Ile Cys Tyr Ile
225                 230                 235                 240
Thr Arg Lys Ser Ala Ser Cys Gln Ala Asp Leu Ala Ser Ser Leu Ser
                    245                 250                 255
Asn Ala Val Gln Ile Val Gly Met Ser Ala Thr Leu Pro Asn Leu Glu
                260                 265                 270
Leu Val Ala Ser Trp Leu Asn Ala Glu Leu Tyr His Thr Asp Phe Arg
            275                 280                 285
Pro Val Pro Leu Leu Glu Ser Val Lys Val Gly Asn Ser Ile Tyr Asp
290                 295                 300
Ser Ser Met Lys Leu Val Arg Glu Phe Glu Pro Met Leu Gln Val Lys
305                 310                 315                 320
Gly Asp Glu Asp His Val Val Ser Leu Cys Tyr Glu Thr Ile Cys Asp
                    325                 330                 335
Asn His Ser Val Leu Leu Phe Cys Pro Ser Lys Lys Trp Cys Glu Lys
                340                 345                 350
Leu Ala Asp Ile Ile Ala Arg Glu Phe Tyr Asn Leu His His Gln Ala
            355                 360                 365
Glu Gly Leu Val Lys Pro Ser Glu Cys Pro Pro Val Ile Leu Glu Gln
370                 375                 380
Lys Glu Leu Leu Glu Val Met Asp Gln Leu Arg Arg Leu Pro Ser Gly
385                 390                 395                 400
Leu Asp Ser Val Leu Gln Lys Thr Val Pro Trp Gly Val Ala Phe His
                    405                 410                 415
His Ala Gly Leu Thr Phe Glu Glu Arg Asp Ile Ile Glu Gly Ala Phe
                420                 425                 430
Arg Gln Gly Leu Ile Arg Val Leu Ala Ala Thr Ser Thr Leu Ser Ser
            435                 440                 445
Gly Val Asn Leu Pro Ala Arg Arg Val Ile Ile Arg Thr Pro Ile Phe
            450                 455                 460
Gly Gly Arg Pro Leu Asp Ile Leu Thr Tyr Lys Gln Met Val Gly Arg
465                 470                 475                 480
Ala Gly Arg Lys Gly Val Asp Thr Val Gly Glu Ser Ile Leu Ile Cys
                    485                 490                 495
Lys Asn Ser Glu Lys Ser Lys Gly Ile Ala Leu Leu Gln Gly Ser Leu
                500                 505                 510
Lys Pro Val Arg Ser Cys Leu Gln Arg Arg Glu Gly Glu Glu Val Thr
            515                 520                 525
Gly Ser Met Ile Arg Ala Ile Leu Glu Ile Ile Val Gly Gly Val Ala
            530                 535                 540
```

```
Ser Thr Ser Gln Asp Met His Thr Tyr Ala Ala Cys Thr Phe Leu Ala
545                 550                 555                 560

Ala Ser Met Lys Glu Gly Lys Gln Gly Ile Gln Arg Asn Gln Glu Ser
                565                 570                 575

Val Gln Leu Gly Ala Ile Glu Ala Cys Val Met Trp Leu Leu Glu Asn
            580                 585                 590

Glu Phe Ile Gln Ser Thr Glu Ala Ser Asp Gly Thr Glu Gly Lys Val
        595                 600                 605

Tyr His Pro Thr His Leu Gly Ser Ala Thr Leu Ser Ser Ser Leu Ser
    610                 615                 620

Pro Ala Asp Thr Leu Asp Ile Phe Ala Asp Leu Gln Arg Ala Met Lys
625                 630                 635                 640

Gly Phe Val Leu Glu Asn Asp Leu His Ile Leu Tyr Leu Val Thr Pro
                645                 650                 655

Met Phe Glu Asp Trp Thr Thr Ile Asp Trp Tyr Arg Phe Phe Cys Leu
            660                 665                 670

Trp Glu Lys Leu Pro Thr Ser Met Lys Arg Val Ala Glu Leu Val Gly
        675                 680                 685

Val Glu Glu Gly Phe Leu Ala Arg Cys Val Lys Gly Lys Val Val Ala
    690                 695                 700

Arg Thr Glu Arg Gln His Arg Gln Met Ala Ile His Lys Arg Phe Phe
705                 710                 715                 720

Thr Ser Leu Val Leu Leu Asp Leu Ile Ser Glu Val Pro Leu Arg Glu
                725                 730                 735

Ile Asn Gln Lys Tyr Gly Cys Asn Arg Gly Ile Gln Ser Leu Gln
            740                 745                 750

Gln Ser Ala Ala Val Tyr Ala Gly Met Ile Thr Val Phe Ser Asn Arg
        755                 760                 765

Leu Gly Trp His Asn Met Glu Leu Leu Leu Ser Gln Phe Gln Lys Arg
    770                 775                 780

Leu Thr Phe Gly Ile Gln Arg Glu Leu Cys Asp Leu Val Arg Val Ser
785                 790                 795                 800

Leu Leu Asn Ala Gln Arg Ala Arg Val Leu Tyr Ala Ser Gly Phe His
                805                 810                 815

Thr Val Ala Asp Leu Ala Arg Ala Asn Ile Val Glu Val Glu Val Ile
            820                 825                 830

Leu Lys Asn Ala Val Pro Phe Lys Ser Ala Arg Lys Ala Val Asp Glu
        835                 840                 845

Glu Glu Glu Ala Val Glu Glu Arg Arg Asn Met Arg Thr Ile Trp Val
    850                 855                 860

Thr Gly Arg Lys Gly Leu Thr Glu Arg Glu Ala Ala Leu Ile Val
865                 870                 875                 880

Glu Glu Ala Arg Met Ile Leu Gln Gln Asp Leu Val Glu Met Gly Val
                885                 890                 895

Gln Trp Asn Pro Cys Ala Leu Leu His Ser Ser Thr Cys Ser Leu Thr
            900                 905                 910

His Ser Glu Ser Glu Val Lys Glu His Thr Phe Ile Ser Gln Thr Lys
        915                 920                 925

Ser Ser Tyr Lys Lys Leu Thr Ser Lys Asn Lys Ser Asn Thr Ile Phe
    930                 935                 940

Ser Asp Ser Tyr Ile Lys His Ser Pro Asn Ile Val Gln Asp Leu Asn
945                 950                 955                 960
```

```
Lys Ser Arg Glu His Thr Ser Ser Phe Asn Cys Asn Phe Gln Asn Gly
             965                 970                 975

Asn Gln Glu His Gln Thr Cys Ser Ile Phe Arg Ala Arg Lys Arg Ala
             980                 985                 990

Ser Leu Asp Ile Asn Lys Glu Lys Pro Gly Ala Ser Gln Asn Glu Gly
             995                 1000                1005

Lys Thr Ser Asp Lys Lys Val Val Gln Thr Phe Ser Gln Lys Thr
        1010                1015                1020

Lys Lys Ala Pro Leu Asn Phe Asn Ser Glu Lys Met Ser Arg Ser
        1025                1030                1035

Phe Arg Ser Trp Lys Arg Arg Lys His Leu Lys Arg Ser Arg Asp
        1040                1045                1050

Ser Ser Pro Leu Lys Asp Ser Gly Ala Cys Arg Ile His Leu Gln
        1055                1060                1065

Gly Gln Thr Leu Ser Asn Pro Ser Leu Cys Glu Asp Pro Phe Thr
        1070                1075                1080

Leu Asp Glu Lys Lys Thr Glu Phe Arg Asn Ser Gly Pro Phe Ala
        1085                1090                1095

Lys Asn Val Ser Leu Ser Gly Lys Glu Lys Asp Asn Lys Thr Ser
        1100                1105                1110

Phe Pro Leu Gln Ile Lys Gln Asn Cys Ser Trp Asn Ile Thr Leu
        1115                1120                1125

Thr Asn Asp Asn Phe Val Glu His Ile Val Thr Gly Ser Gln Ser
        1130                1135                1140

Lys Asn Val Thr Cys Gln Ala Thr Ser Val Val Ser Glu Lys Gly
        1145                1150                1155

Arg Gly Val Ala Val Glu Ala Glu Lys Ile Asn Glu Val Leu Ile
        1160                1165                1170

Gln Asn Gly Ser Lys Asn Gln Asn Val Tyr Met Lys His His Asp
        1175                1180                1185

Ile His Pro Ile Asn Gln Tyr Leu Arg Lys Gln Ser His Glu Gln
        1190                1195                1200

Thr Ser Thr Ile Thr Lys Gln Lys Asn Ile Ile Glu Arg Gln Met
        1205                1210                1215

Pro Cys Glu Ala Val Ser Ser Tyr Ile Asn Arg Asp Ser Asn Val
        1220                1225                1230

Thr Ile Asn Cys Glu Arg Ile Lys Leu Asn Thr Glu Glu Asn Lys
        1235                1240                1245

Pro Ser His Phe Gln Ala Leu Gly Asp Asp Ile Ser Arg Thr Val
        1250                1255                1260

Ile Pro Ser Glu Val Leu Pro Ser Ala Gly Ala Phe Ser Lys Ser
        1265                1270                1275

Glu Gly Gln His Glu Asn Phe Leu Asn Ile Ser Arg Leu Gln Glu
        1280                1285                1290

Lys Thr Gly Thr Tyr Thr Thr Asn Lys Thr Lys Asn Asn His Val
        1295                1300                1305

Ser Asp Leu Gly Leu Val Leu Cys Asp Phe Glu Asp Ser Phe Tyr
        1310                1315                1320

Leu Asp Thr Gln Ser Glu Lys Ile Ile Gln Gln Met Ala Thr Glu
        1325                1330                1335

Asn Ala Lys Leu Gly Ala Lys Asp Thr Asn Leu Ala Ala Gly Ile
        1340                1345                1350

Met Gln Lys Ser Leu Val Gln Gln Asn Ser Met Asn Ser Phe Gln
```

```
            1355                1360                1365

Lys Glu Cys His Ile Pro Phe Pro Ala Glu Gln His Pro Leu Gly
       1370                1375                1380

Ala Thr Lys Ile Asp His Leu Asp Leu Lys Thr Val Gly Thr Met
       1385                1390                1395

Lys Gln Ser Ser Asp Ser His Gly Val Asp Ile Leu Thr Pro Glu
       1400                1405                1410

Ser Pro Ile Phe His Ser Pro Ile Leu Leu Glu Glu Asn Gly Leu
       1415                1420                1425

Phe Leu Lys Lys Asn Glu Val Ser Val Thr Asp Ser Gln Leu Asn
       1430                1435                1440

Ser Phe Leu Gln Gly Tyr Gln Thr Gln Glu Thr Val Lys Pro Val
       1445                1450                1455

Ile Leu Leu Ile Pro Gln Lys Arg Thr Pro Thr Gly Val Glu Gly
       1460                1465                1470

Glu Cys Leu Pro Val Pro Glu Thr Ser Leu Asn Met Ser Asp Ser
       1475                1480                1485

Leu Leu Phe Asp Ser Phe Ser Asp Asp Tyr Leu Val Lys Glu Gln
       1490                1495                1500

Leu Pro Asp Met Gln Met Lys Glu Pro Leu Pro Ser Glu Val Thr
       1505                1510                1515

Ser Asn His Phe Ser Asp Ser Leu Cys Leu Gln Glu Asp Leu Ile
       1520                1525                1530

Lys Lys Ser Asn Val Asn Glu Asn Gln Asp Thr His Gln Gln Leu
       1535                1540                1545

Thr Cys Ser Asn Asp Glu Ser Ile Ile Phe Ser Glu Met Asp Ser
       1550                1555                1560

Val Gln Met Val Glu Ala Leu Asp Asn Val Asp Ile Phe Pro Val
       1565                1570                1575

Gln Glu Lys Asn His Thr Val Val Ser Pro Arg Ala Leu Glu Leu
       1580                1585                1590

Ser Asp Pro Val Leu Asp Glu His His Gln Gly Asp Gln Asp Gly
       1595                1600                1605

Gly Asp Gln Asp Glu Arg Ala Glu Lys Ser Lys Leu Thr Gly Thr
       1610                1615                1620

Arg Gln Asn His Ser Phe Ile Trp Ser Gly Ala Ser Phe Asp Leu
       1625                1630                1635

Ser Pro Gly Leu Gln Arg Ile Leu Asp Lys Val Ser Ser Pro Leu
       1640                1645                1650

Glu Asn Glu Lys Leu Lys Ser Met Thr Ile Asn Phe Ser Ser Leu
       1655                1660                1665

Asn Arg Lys Asn Thr Glu Leu Asn Glu Glu Gln Glu Val Ile Ser
       1670                1675                1680

Asn Leu Glu Thr Lys Gln Val Gln Gly Ile Ser Phe Ser Ser Asn
       1685                1690                1695

Asn Glu Val Lys Ser Lys Ile Glu Met Leu Glu Asn Asn Ala Asn
       1700                1705                1710

His Asp Glu Thr Ser Ser Leu Leu Pro Arg Lys Glu Ser Asn Ile
       1715                1720                1725

Val Asp Asp Asn Gly Leu Ile Pro Pro Thr Pro Ile Pro Thr Ser
       1730                1735                1740

Ala Ser Lys Leu Thr Phe Pro Gly Ile Leu Glu Thr Pro Val Asn
       1745                1750                1755
```

```
Pro Trp Lys Thr Asn Asn Val Leu Gln Pro Gly Glu Ser Tyr Leu
    1760                1765                1770

Phe Gly Ser Pro Ser Asp Ile Lys Asn His Asp Leu Ser Pro Gly
    1775                1780                1785

Ser Arg Asn Gly Phe Lys Asp Asn Ser Pro Ile Ser Asp Thr Ser
    1790                1795                1800

Phe Ser Leu Gln Leu Ser Gln Asp Gly Leu Gln Leu Thr Pro Ala
    1805                1810                1815

Ser Ser Ser Ser Glu Ser Leu Ser Ile Ile Asp Val Ala Ser Asp
    1820                1825                1830

Gln Asn Leu Phe Gln Thr Phe Ile Lys Glu Trp Arg Cys Lys Lys
    1835                1840                1845

Arg Phe Ser Ile Ser Leu Ala Cys Glu Lys Ile Arg Ser Leu Thr
    1850                1855                1860

Ser Ser Lys Thr Ala Thr Ile Gly Ser Arg Phe Lys Gln Ala Ser
    1865                1870                1875

Ser Pro Gln Glu Ile Pro Ile Arg Asp Asp Gly Phe Pro Ile Lys
    1880                1885                1890

Gly Cys Asp Asp Thr Leu Val Val Gly Leu Ala Val Cys Trp Gly
    1895                1900                1905

Gly Arg Asp Ala Tyr Tyr Phe Ser Leu Gln Lys Glu Gln Lys His
    1910                1915                1920

Ser Glu Ile Ser Ala Ser Leu Val Pro Pro Ser Leu Asp Pro Ser
    1925                1930                1935

Leu Thr Leu Lys Asp Arg Met Trp Tyr Leu Gln Ser Cys Leu Arg
    1940                1945                1950

Lys Glu Ser Asp Lys Glu Cys Ser Val Val Ile Tyr Asp Phe Ile
    1955                1960                1965

Gln Ser Tyr Lys Ile Leu Leu Leu Ser Cys Gly Ile Ser Leu Glu
    1970                1975                1980

Gln Ser Tyr Glu Asp Pro Lys Val Ala Cys Trp Leu Leu Asp Pro
    1985                1990                1995

Asp Ser Gln Glu Pro Thr Leu His Ser Ile Val Thr Ser Phe Leu
    2000                2005                2010

Pro His Glu Leu Pro Leu Leu Glu Gly Met Glu Thr Ser Gln Gly
    2015                2020                2025

Ile Gln Ser Leu Gly Leu Asn Ala Gly Ser Glu His Ser Gly Arg
    2030                2035                2040

Tyr Arg Ala Ser Val Glu Ser Ile Leu Ile Phe Asn Ser Met Asn
    2045                2050                2055

Gln Leu Asn Ser Leu Leu Gln Lys Glu Asn Leu Gln Asp Val Phe
    2060                2065                2070

Arg Lys Val Glu Met Pro Ser Gln Tyr Cys Leu Ala Leu Leu Glu
    2075                2080                2085

Leu Asn Gly Ile Gly Phe Ser Thr Ala Glu Cys Glu Ser Gln Lys
    2090                2095                2100

His Ile Met Gln Ala Lys Leu Asp Ala Ile Glu Thr Gln Ala Tyr
    2105                2110                2115

Gln Leu Ala Gly His Ser Phe Ser Phe Thr Ser Ser Asp Asp Ile
    2120                2125                2130

Ala Glu Val Leu Phe Leu Glu Leu Lys Leu Pro Pro Asn Arg Glu
    2135                2140                2145
```

-continued

Met Lys Asn Gln Gly Ser Lys Lys Thr Leu Gly Ser Thr Arg Arg
2150             2155             2160

Gly Ile Asp Asn Gly Arg Lys Leu Arg Leu Gly Arg Gln Phe Ser
2165             2170             2175

Thr Ser Lys Asp Val Leu Asn Lys Leu Lys Ala Leu His Pro Leu
2180             2185             2190

Pro Gly Leu Ile Leu Glu Trp Arg Arg Ile Thr Asn Ala Ile Thr
2195             2200             2205

Lys Val Val Phe Pro Leu Gln Arg Glu Lys Cys Leu Asn Pro Phe
2210             2215             2220

Leu Gly Met Glu Arg Ile Tyr Pro Val Ser Gln Ser His Thr Ala
2225             2230             2235

Thr Gly Arg Ile Thr Phe Thr Glu Pro Asn Ile Gln Asn Val Pro
2240             2245             2250

Arg Asp Phe Glu Ile Lys Met Pro Thr Leu Val Gly Glu Ser Pro
2255             2260             2265

Pro Ser Gln Ala Val Gly Lys Gly Leu Leu Pro Met Gly Arg Gly
2270             2275             2280

Lys Tyr Lys Lys Gly Phe Ser Val Asn Pro Arg Cys Gln Ala Gln
2285             2290             2295

Met Glu Glu Arg Ala Ala Asp Arg Gly Met Pro Phe Ser Ile Ser
2300             2305             2310

Met Arg His Ala Phe Val Pro Phe Pro Gly Gly Ser Ile Leu Ala
2315             2320             2325

Ala Asp Tyr Ser Gln Leu Glu Leu Arg Ile Leu Ala His Leu Ser
2330             2335             2340

His Asp Arg Arg Leu Ile Gln Val Leu Asn Thr Gly Ala Asp Val
2345             2350             2355

Phe Arg Ser Ile Ala Ala Glu Trp Lys Met Ile Glu Pro Glu Ser
2360             2365             2370

Val Gly Asp Asp Leu Arg Gln Gln Ala Lys Gln Ile Cys Tyr Gly
2375             2380             2385

Ile Ile Tyr Gly Met Gly Ala Lys Ser Leu Gly Glu Gln Met Gly
2390             2395             2400

Ile Lys Glu Asn Asp Ala Ala Cys Tyr Ile Asp Ser Phe Lys Ser
2405             2410             2415

Arg Tyr Thr Gly Ile Asn Gln Phe Met Thr Glu Thr Val Lys Asn
2420             2425             2430

Cys Lys Arg Asp Gly Phe Val Gln Thr Ile Leu Gly Arg Arg Arg
2435             2440             2445

Tyr Leu Pro Gly Ile Lys Asp Asn Asn Pro Tyr Arg Lys Ala His
2450             2455             2460

Ala Glu Arg Gln Ala Ile Asn Thr Ile Val Gln Gly Ser Ala Ala
2465             2470             2475

Asp Ile Val Lys Ile Ala Thr Val Asn Ile Gln Lys Gln Leu Glu
2480             2485             2490

Thr Phe His Ser Thr Phe Lys Ser His Gly His Arg Glu Gly Met
2495             2500             2505

Leu Gln Ser Asp Gln Thr Gly Leu Ser Arg Lys Arg Lys Leu Gln
2510             2515             2520

Gly Met Phe Cys Pro Ile Arg Gly Gly Phe Phe Ile Leu Gln Leu
2525             2530             2535

His Asp Glu Leu Leu Tyr Glu Val Ala Glu Glu Asp Val Val Gln

```
                2540              2545              2550
Val  Ala  Gln  Ile  Val  Lys  Asn  Glu  Met  Glu  Ser  Ala  Val  Lys  Leu
           2555                2560                2565

Ser  Val  Lys  Leu  Lys  Val  Lys  Val  Lys  Ile  Gly  Ala  Ser  Trp  Gly
     2570                2575                2580

Glu  Leu  Lys  Asp  Phe  Asp  Val
     2585                2590

<210> SEQ ID NO 3
<211> LENGTH: 2204
<212> TYPE: DNA
<213> ORGANISM: homo sapiens
<220> FEATURE:
<221> NAME/KEY: misc_feature
<223> OTHER INFORMATION: PLK1 gene

<400> SEQUENCE: 3
gagcggtgcg gaggctctgc tcggatcgag gtctgcagcg cagcttcggg agcatgagtg       60
ctgcagtgac tgcagggaag ctggcacggg caccggccga ccctgggaaa gccggggtcc      120
ccggagttgc agctcccgga gctccggcgg cggctccacc ggcgaaagag atcccggagg      180
tcctagtgga cccacgcagc cggcggcgct atgtgcgggg ccgcttttg ggcaaggggcg      240 gctttgccaa gtgcttcgag atctcggacg cggacaccaa ggaggtgttc gcgggcaaga      300
ttgtgcctaa gtctctgctg ctcaagcgc accagaggga agatgtgcc atggaaatat       360 ccattcaccg cagcctcgcc caccagcacg tcgtaggatt ccacggcttt ttcgaggaca      420
acgacttcgt gttcgtggtg ttggagctct gccgccggag gtctctcctg gagctgcaca      480
agaggaggaa agccctgact gagcctgagg ccgatacta cctacggcaa attgtgcttg      540
gctgccagta cctgcaccga aaccgagtta ttcatcgaga cctcaagctg ggcaaccttt      600
tcctgaatga agatctggag gtgaaaatag ggattttgg actggcaacc aaagtcgaat      660
atgacgggga gaggaagaag accctgtgtg ggactcctaa ttacatagct cccgaggtgc      720
tgagcaagaa agggcacagt ttcgaggtgg atgtgtggtc cattgggtgt atcatgtata      780
ccttgttagt gggcaaacca cctttttgaga cttcttgcct aaaagagacc tacctccgga      840
tcaagaagaa tgaatacagt attcccaagc acatcaaccc cgtggccgcc tccctcatcc      900
agaagatgct tcagacagat cccactgccc gcccaaccat taacgagctg cttaatgacg      960
agttctttac ttctggctat atccctgccc gtctccccat cacctgcctg accattccac     1020
caaggttttc gattgctccc agcagcctgg accccagcaa ccggaagccc ctcacagtcc     1080
tcaataaagg cttggagaac cccctgcctg agcgtccccg ggaaaaagaa gaaccagtgg     1140
ttcgagagac aggtgaggtg gtcgactgcc acctcagtga catgctgcag cagctgcaca     1200
gtgtcaatgc ctccaagccc tcggagcgtg ggctggtcag gcaagaggag ctgaggatc      1260 ctgcctgcat ccccatcttc tgggtcagca agtgggtgga ctattcggac aagtacggcc     1320
ttgggtatca gctctgtgat aacagcgtgg gggtgctctt caatgactca acacgcctca     1380
tcctctacaa tgatggtgac agcctgcagt acatagagcg tgacggcact gagtcctacc     1440
tcaccgtgag ttcccatccc aactccttga tgaagaagat cacctccctt aaatatttcc     1500
gcaattacat gagcgagcac ttgctgaagg caggtgccaa catcacgccg cgcgaaggtg     1560
atgagctcgc ccggctgccc tacctacgga cctggttccg cacccgcagc gccatcatcc     1620
tgcacctcag caacgcagc gtgcagatca acttcttcca ggatcacacc aagctcatct      1680
tgtgcccact gatggcagcc gtgacctaca tcgacgagaa gcgggacttc cgcacatacc     1740
```

-continued

```
gcctgagtct cctggaggag tacggctgct gcaaggagct ggccagccgg ctccgctacg    1800
cccgcactat ggtggacaag ctgctgagct cacgctcggc cagcaaccgt tcaaggcct     1860 cctaatagct gccctcccct ccggactggt gccctcctca ctcccacctg catctggggc    1920
ccatactggt tggctcccgc ggtgccatgt ctgcagtgtg ccccccagcc ccggtggctg    1980
ggcagagctg catcatcctt gcaggtgggg gttgctgtgt aagttatttt tgtacatgtt    2040
cgggtgtggg ttctacagcc ttgtcccct ccccctcaac cccaccatat gaattgtaca     2100
gaatatttct attgaattcg gaactgtcct ttccttggct ttatgcacat taaacagatg    2160
tgaatattca aaaaaaaaa aaaaaaaaa aaaaaaaaa aaaa                        2204
```

<210> SEQ ID NO 4
<211> LENGTH: 603
<212> TYPE: PRT
<213> ORGANISM: homo sapiens
<220> FEATURE:
<221> NAME/KEY: misc_feature
<223> OTHER INFORMATION: PLK1 protein

<400> SEQUENCE: 4

```
Met Ser Ala Ala Val Thr Ala Gly Lys Leu Ala Arg Ala Pro Ala Asp
1               5                   10                  15

Pro Gly Lys Ala Gly Val Pro Gly Val Ala Ala Pro Gly Ala Pro Ala
            20                  25                  30

Ala Ala Pro Pro Ala Lys Glu Ile Pro Glu Val Leu Val Asp Pro Arg
        35                  40                  45

Ser Arg Arg Arg Tyr Val Arg Gly Arg Phe Leu Gly Lys Gly Gly Phe
    50                  55                  60

Ala Lys Cys Phe Glu Ile Ser Asp Ala Asp Thr Lys Glu Val Phe Ala
65                  70                  75                  80

Gly Lys Ile Val Pro Lys Ser Leu Leu Leu Lys Pro His Gln Arg Glu
                85                  90                  95

Lys Met Ser Met Glu Ile Ser Ile His Arg Ser Leu Ala His Gln His
            100                 105                 110

Val Val Gly Phe His Gly Phe Phe Glu Asp Asn Asp Phe Val Phe Val
        115                 120                 125

Val Leu Glu Leu Cys Arg Arg Arg Ser Leu Leu Glu Leu His Lys Arg
    130                 135                 140

Arg Lys Ala Leu Thr Glu Pro Glu Ala Arg Tyr Tyr Leu Arg Gln Ile
145                 150                 155                 160

Val Leu Gly Cys Gln Tyr Leu His Arg Asn Arg Val Ile His Arg Asp
                165                 170                 175

Leu Lys Leu Gly Asn Leu Phe Leu Asn Glu Asp Leu Glu Val Lys Ile
            180                 185                 190

Gly Asp Phe Gly Leu Ala Thr Lys Val Glu Tyr Asp Gly Glu Arg Lys
        195                 200                 205

Lys Thr Leu Cys Gly Thr Pro Asn Tyr Ile Ala Pro Glu Val Leu Ser
    210                 215                 220

Lys Lys Gly His Ser Phe Glu Val Asp Val Trp Ser Ile Gly Cys Ile
225                 230                 235                 240

Met Tyr Thr Leu Leu Val Gly Lys Pro Pro Phe Glu Thr Ser Cys Leu
                245                 250                 255

Lys Glu Thr Tyr Leu Arg Ile Lys Lys Asn Glu Tyr Ser Ile Pro Lys
            260                 265                 270
```

```
His Ile Asn Pro Val Ala Ala Ser Leu Ile Gln Lys Met Leu Gln Thr
            275                 280                 285

Asp Pro Thr Ala Arg Pro Thr Ile Asn Glu Leu Leu Asn Asp Glu Phe
290                 295                 300

Phe Thr Ser Gly Tyr Ile Pro Ala Arg Leu Pro Ile Thr Cys Leu Thr
305                 310                 315                 320

Ile Pro Pro Arg Phe Ser Ile Ala Pro Ser Ser Leu Asp Pro Ser Asn
            325                 330                 335

Arg Lys Pro Leu Thr Val Leu Asn Lys Gly Leu Glu Asn Pro Leu Pro
            340                 345                 350

Glu Arg Pro Arg Glu Lys Glu Glu Pro Val Val Arg Glu Thr Gly Glu
            355                 360                 365

Val Val Asp Cys His Leu Ser Asp Met Leu Gln Gln Leu His Ser Val
370                 375                 380

Asn Ala Ser Lys Pro Ser Glu Arg Gly Leu Val Arg Gln Glu Glu Ala
385                 390                 395                 400

Glu Asp Pro Ala Cys Ile Pro Ile Phe Trp Val Ser Lys Trp Val Asp
                405                 410                 415

Tyr Ser Asp Lys Tyr Gly Leu Gly Tyr Gln Leu Cys Asp Asn Ser Val
            420                 425                 430

Gly Val Leu Phe Asn Asp Ser Thr Arg Leu Ile Leu Tyr Asn Asp Gly
            435                 440                 445

Asp Ser Leu Gln Tyr Ile Glu Arg Asp Gly Thr Glu Ser Tyr Leu Thr
            450                 455                 460

Val Ser Ser His Pro Asn Ser Leu Met Lys Lys Ile Thr Leu Leu Lys
465                 470                 475                 480

Tyr Phe Arg Asn Tyr Met Ser Glu His Leu Leu Lys Ala Gly Ala Asn
                485                 490                 495

Ile Thr Pro Arg Glu Gly Asp Glu Leu Ala Arg Leu Pro Tyr Leu Arg
            500                 505                 510

Thr Trp Phe Arg Thr Arg Ser Ala Ile Ile Leu His Leu Ser Asn Gly
            515                 520                 525

Ser Val Gln Ile Asn Phe Phe Gln Asp His Thr Lys Leu Ile Leu Cys
530                 535                 540

Pro Leu Met Ala Ala Val Thr Tyr Ile Asp Glu Lys Arg Asp Phe Arg
545                 550                 555                 560

Thr Tyr Arg Leu Ser Leu Leu Glu Glu Tyr Gly Cys Cys Lys Glu Leu
                565                 570                 575

Ala Ser Arg Leu Arg Tyr Ala Arg Thr Met Val Asp Lys Leu Leu Ser
            580                 585                 590

Ser Arg Ser Ala Ser Asn Arg Leu Lys Ala Ser
            595                 600

<210> SEQ ID NO 5
<211> LENGTH: 8292
<212> TYPE: DNA
<213> ORGANISM: homo sapiens
<220> FEATURE:
<221> NAME/KEY: misc_feature
<223> OTHER INFORMATION: CLASPIN gene

<400> SEQUENCE: 5
gacggcggga gccgctgctc tccggctgag ggaatcagag acagctccgt ccctagtgga      60
gcgcagggga ggcagaagtc atgacaggcg aggtgggttc tgaggttcac ctagaaatca     120
atgacccaaa cgtcatttca caagaggaag cagatagtcc ttcagatagt ggacagggca     180
```

```
gctatgaaac aattggaccc ttgagtgaag gagattcaga tgaagagata tttgtaagta      240
agaagttgaa aaacaggaag gttctacaag acagtgattc cgaaacagag gacacaaatg     300
cctctccaga gaaaactacc tatgacagtg ccgaggagga aaataaagag aatttatatg     360
ctgggaaaaa tacaaaaatc aaaaggattt acaaaactgt ggcagacagt gatgaaagtt     420
acatggaaaa gtctttgtat caggaaaatc ttgaagcgca agtgaaacct tgcttagagc     480
tgagtcttca gtctggaaac tctacagact ttaccactga cagaaagagt tccaaaaagc     540
acatacatga taaagaagga actgcaggaa aagcaaaagt aaaatcaaaa gaagacttg      600 agaaagagga gagaaaaatg gaaaaaatta gacagctaaa aagaaggaa acaaaaaacc      660 aggaagatga tgtagaacag ccatttaatg acagtggctg tcttcttgtg gataaagacc     720
tttttgaaac tggggttggag gatgaaaata actctccatt ggaagatgaa gagtcattag    780
aatcaataag agcagctgta aaaaacaaag taaaaaagca aagaaaaaa gaaccatctt      840 tggagagtgg ggtccattca tttgaggaag gaagtgagtt atcaaaagga accacgagga    900
aggaaagaaa ggcagccaga ttaagtaaag aagcattaaa acaactgcat agtgagactc    960
agcgccttat tcgagagtct gcactgaacc ttccatatca tatgcctgag aataaaacca   1020
ttcatgattt cttcaaacgt aaaccccggc ccacttgcca cggaaatgcc atggcactat   1080
tgaagtcatc taaatatcag tcaagccatc acaaagaaat catagacact gcaaatacta   1140
ctgaaatgaa cagtgatcac catagtaaag gttctgagca gacaacaggt gcagaaaatg   1200
aagtggaaac taatgcactc cctgtagttt caaaggaaac ccagatcatt actggatcag   1260
atgagtcttg caggaaggat ttggtaaaaa atgaagagct agaaattcag gagaaacaga   1320
agcagagtga cattagacct tcacctgggg acagctcagt gttgcaacag gaatccaact   1380
tcctcgggaa caatcacagt gaggaatgtc aggttggagg gcttgtagca tttgaacctc   1440
atgccctgga gggtgaaggc ccccaaaatc cagaagaaac agatgagaaa gtggaagagc   1500
ctgagcagca aaataaatca tcagcagttg ggccacctga aaaagtgaga cggtttactc   1560
tggatagact taagcaactg ggagtagatg ttttccattaa accacggcta ggtgctgatg   1620
aagattcctt tgtgatactt gaacctgaaa ccaacagagg tgaaaagctt caggtgttaa   1680
aagctaaact gcaagaagca atgaaactcc gaaggtttga ggagcgccag aagcgccaag   1740
cactgtttaa attagataat gaagatgggt ttgaggaaga ggaggaggaa gaggaagaaa   1800
tgacagatga gtctgaggaa gatggagaag agaaggtaga gaaagaagag aaagaggaag   1860
aactagagga agaggaggag aaagaagagg aggaggaaga agaaggaaat caggagactg   1920
cagaattcct tcttagtagt gaagaaatag aaacaaaaga tgaaaagaa atggataaag   1980 aaaataatga tggcagtagt gaaattggca aggcagttgg cttcctctct gttcccaagt   2040
ctctctcatc agattctact ttacttctgt ttaaggacag ctcttccaag atgggttact   2100
ttcctactga agaaaaatca gaaacagatg aaaactcagg caagcagcct agcaaactgg   2160
atgaggatga ttcatgttca ttgctaacaa aggagagcag ccacaatagc agctttgagc   2220
tgattggctc cacgattcca tcctatcagc cttgcaacag acaaacaggc cgtgggacca   2280 gtttttttccc tacagcagga ggattcagat ctccttcccc tgggctattt cgagccagtt   2340
tggtcagctc agcttctaag agttcaggga aactgtctga gccttcactt cccatagagg   2400
attcccagga tctgtataac gcctccccag agcctaagac acttttccta ggagcaggag   2460
acttccagtt ctgtttagaa gatgacactc agagccaact gttggatgca gatgggttct   2520
```

```
taaatgttag aaaccacagg aatcagtacc aagctttgaa gcctcgattg ccattggcca    2580
gtatggatga gaatgccatg gatgccaaca tggatgagct gttggatttg tgtactggaa    2640
agttcacatc tcaggctgaa aaacatctac ccaggaagag tgacaagaaa gagaacatgg    2700
aggaacttct gaacctttgt tcaggaaaat tcacttctca ggatgcctcc actccagcct    2760
catcagagtt aaataaacag gagaaggaga gcagcatggg tgatccaatg gaagaagcac    2820
ttgctctttg ctcaggctct tttcccacag acaaggaaga ggaagacgag gaggaggaat    2880
ttggagactt tcggcttgtt tcaaatgata atgagtttga tagtgatgag gatgaacaca    2940
gtgactctgg taatgatctg gcactggaag accatgaaga tgatgatgaa gagaactcc    3000 tgaagcgatc tgagaagttg aaaaggcaaa tgaggttgag gaaataccg gaggatgagg    3060 cagaggtgtc aggaagtgat gtgggaagcg aagatgagta tgatgggaa gaaattgatg    3120 aatatgaaga ggacgtaatt gatgaagtac ttccttctga tgaggaactg cagagtcaaa    3180
tcaagaaaat acacatgaaa actatgttga atgatgataa gcgacagcta cgtttatacc    3240
aagagaggta ccttgctgat ggggatctgc acagcgatgg tcctgggcga atgaggaagt    3300
ttcgatggaa aaacatagat gatgcttccc agatggactt gttccacaga gactctgatg    3360
atgatcagac tgaagaacag cttgatgagt cagaagccag gtggaggaag gagcgaattg    3420
aacgagagca gtggcttcgg gacatggcac agcagggaa aattacagct gaagaagaag    3480
aagaaattgg ggaggacagt cagtttatga tactggccaa gaaagttaca gccaaagcac    3540
tgcagaagaa tgccagtcgc cctatggtta ttcaggaatc aaagtctttg ctcagaaatc    3600
cttttgaagc catcagacca ggaagtgctc aacaggtgaa gacaggctca ctgctaaacc    3660
agcccaaagc tgtgcttcag aaactggctg ctctctctga ccataacccc agtgctcctc    3720
gaaattcaag aaactttgtc tttcatacac tttctcctgt caaggctgag gcggcaaagg    3780
aatcgtctaa gtctcaggta aagaaaaggg gtccatcttt catgacttct ccttcaccta    3840
agcacctcaa aacagatgat agcacttcag gattgacgcg aagcatcttc aaatatttgg    3900
agagctaaca ccatcaaagg tgccaaaatc tacattgaga ctgctttgag aagtttctag    3960
cactgaaagt tggaattgac actccagcca atgatccttc cttctttcat aatcaatgca    4020
ataagattgc agacagaaat tccagtgatt tctactgcac agctctggac atctcttttc    4080
ctagtattat tccctgaatt ggccactgat ttcaattctg cagtatttac aacatcaaca    4140
actcatggaa tacttgggtg aggtttcctt tttttttttt ttttaagat gggagtctca    4200 ctctgttgcc cagcttggag tgcagtgcg tgatctcggc tcaccacaat ctctgcctcc    4260
caggttcaag cgattctcct ccttcagcct cccgagtagc tgggattaca ggcatgtgcc    4320
aatacgccca gctaattttt gtattttag tagagacggg gtttcaccat gttgccagg    4380 ctggtcttga actcctgacc tcaaatgatc catccacctc ggccccacaa agtgctggtc    4440
acatgcatga gtcactgcac ctggccttgg gttaggtttc acttcctcca ttagacattt    4500
gacattttat tgtagcagct ttctgggtta atatctcttt gtgattgata gaagtggttg    4560
gaagaggaag agtagggaaa agtgtgacat tacagattaa acagtgaaaa tcagtaccat    4620
aatgactcct ttacacccat gagatacgta ccatgatgac cagggctcgg tgaaagaaag    4680 atttctttt tttttttga gatagtctca ctttgttgcc cagtctggag tgcagtggcg    4740
caatctcggc tcacggcaac ctctgcctcc cgggttcaag tgattctcct gtctcagcct    4800
cccaagtagc tgggactaca ggtgcatgcc accacacctg gctaattttt gtattttag    4860 tggagacagg gagtcaccat gttggccagg ctggtctcga tctcctgacc tcaagtgatc    4920
```

```
cagctgcctc agcctcccaa agtgctgaga ttacaggcgt gagccactgt gcccagccaa    4980
aagaacgatt tcttagatgg aggacctagg aaccaacaga tgggctgctg tattactctt    5040
acccctttca ttttcctgta tgcttcttcc caaggcagca tcaaattttg aattaatttt    5100
tgctgcttaa taaggactta aactggtacc caagtcagaa agactctgcc tctaattttc    5160
tggggcttgg ggatgaagat aaagtgttac acccagtgtt tgtccaccac agtctgtggg    5220
gcagagagac ccttcctggg actgaattct caatttgaag cactgttgtt caaagatctc    5280
ccttctgggt ctgacaagaa gaaacataac ccttatttat tgcattcttc tggcttacat    5340
acattgccct cactaatcaa tggacatttc agcatttcat tactaatttt gagagaaggc    5400
caccatggaa tttaataaaa atattattga agagaattgc catcattctc catttttccct    5460
gaactaccac aagcttctca gaattttaga caaatgtttt tcccctcaga actgagcatc    5520
agtgctgctt tggaaaaaca ttccatgtga atactgtggt ttcagtgtca ggacctgtac    5580
ttgggcagtt ggaagagagt gtgccagttt tttactggga gatgggaaca ccaatttaat    5640
tgatgcaatt aggttgtagg ttttttacag tttttctttt cttttctttt tcttttcttt    5700
ttcttttctt ttcttttttt tttttgaga cataggctgg ctctgtcacc taggctggaa    5760
tacaatggca tgatctcggc ttactgcaac ctccgcctcc taggttcaag caattctgcc    5820
tcggcctccc aaatagcagg gattacaggc acctgccacc actcccagct aattttttgt    5880
atttttatta gagatgaggt ttcgccatgt tggccaggct ggtcttgaac tcctgacctg    5940
aggtgatcca cccgtctcgg cctcccaaag tgctgggatt ataggcatga gccaccgcac    6000
ccggccggtt ttctacagtt ttctaatact caagatgttg actttgacaa tacttatgtt    6060
tgtatacttg taatcttata atggggaaaa tgtgtataaa gatgttttaa tatgtatgta    6120
gtttttcaat aaatcttaat gccttgaagg gaagatttgc tgtccagctt gaatgctcat    6180
tcttgggtca gtgcctgtct aaccttgagg agcatttcat tttcaggtta tctccatccc    6240
agggaaaccc tctgggtcta aactgagaag ctgctgcaat tgtcccctca ctggcttctc    6300
agtcctagtg aattgatcaa gttaacttac caagtggttt gggttcagct caggtgaaga    6360
ggataattga gtttacataa atggtacctt ctattatagc tctttgttta aaaaacttat    6420
tttttagaga cagtctcatt ctgttgccca ggttagagtg cagtggcaca atcatagctc    6480
actgtaccct tgaactcctg gcttcagca tcctccttcc tcaacctttg gaatagctgg    6540
gccacattac aggcatatgc caccatgccc agctaattat tttattttag tagagacagg    6600
gtcttgctgt gttgccccag ctgatcttga actcctggcc tcagtaatc ctcccacctt    6660
ggcctcccaa aatgctgggg tcacaggctc agccaccatg cccagcctgt tacagctttg    6720
attggccttt ctctttagct aagtttgtat gtacttcatt ttatccatgg gttcaagata    6780
catgtttttg cctctttctt tgaactctct aaacagttcc caaggcaaag tagcccttgc    6840
tgggcaaaag agaactgagc aggaaggcta gatatttctt ccctcttgtt tccctacatg    6900
tcttttgagg agagatagaa aagacaattg gaattgacaa ctgaggataa gaaaattcag    6960
ccaggtccgg tggctcacgc cagcacttta ggagactgag gtgggtgcat tgcttgaact    7020
caggagttcg agaccagcct gggaaacatg gtgaaatccc aactctaaaa aaaaaaaaaa    7080
aaagaaaaaa aaagaaaaat tagtgcctga gaaatccagg gagaaaatgg tttctgggct    7140
gggcgtggtg gctatgcct gtaatctcag cactttggga ggctgaggca gctggatcac    7200
ctaaggtcag gagttggaga ccagactgac caacaaggtg aaaccccgtc tctactaaaa    7260
```

-continued

```
atacaaaaat cagccaggct tggtggtggc aggtgcctgt agtcccagct acttgggagg    7320
ctgagacaag agaattgctt gaacctggga ggcagaggtt gcagtgagcc gagatcacgc    7380
cactgctctc cagcatgggc gacagagtga gactccctct caaaaaaaaa aagaaagaaa    7440
gaaaatggtt tctgattgag ctcctgggaa gaaagcactc tttggagaaa gaaaacttga    7500
gtcaaactct gggttacttt tccttatgcc aggatggctg ctataaagta agctaagcct    7560
tgatcttggt aacaggattg acatggacag tttcaatctg acccatatgc cctttgccca    7620
aagcactgag ccagcagcat cagttatgtt ttaatgaaat tgaagcccca ggacctgcca    7680
ctatggctct gaggaggact cagcttcact agcttggaaa ttacatattt ggagggatga    7740
gagcccatga gtgtgggaga tagggtaggc tcagtgtcag tgtttttgtt tcttccttgt    7800
tccatacact tgagtaggga tacatggtat aacctctttt aaacaggtct ctaatttcat    7860
ctcattaatt cacagttgca cagccatact agggtctctt ccataaacca taagatttta    7920
ttcaccaaag ctctagagac aaggtactca gatctctgtg gcatccctca tttctcaac     7980 tgcttctcta caaacttctc ctcactttga gagtttctaa tgctcaggct gggagacttt    8040 ttaggggggtg ttttttggttt ttatctccta gggttatgtc taatcactct tgtggcatcc  8100
tgtcctggga tttgtgctcc taaggataga ggagagtatt tctgggagga gtgttcccat    8160
gatactattt gattatgtca tccttgagat ggtattgtat cttctaccct tatatcctac    8220
tcatcgcctg gcacacagct tggaatgtag tggtgcctac cacagtttga ataaataaca    8280
ctacaccttt ca                                                       8292
```

<210> SEQ ID NO 6
<211> LENGTH: 1275
<212> TYPE: PRT
<213> ORGANISM: homo sapiens
<220> FEATURE:
<221> NAME/KEY: misc_feature
<223> OTHER INFORMATION: CLASPIN protein

<400> SEQUENCE: 6

```
Met Thr Gly Glu Val Gly Ser Glu Val His Leu Glu Ile Asn Asp Pro
1               5                   10                  15

Asn Val Ile Ser Gln Glu Glu Ala Asp Ser Pro Ser Asp Ser Gly Gln
            20                  25                  30

Gly Ser Tyr Glu Thr Ile Gly Pro Leu Ser Glu Gly Asp Ser Asp Glu
        35                  40                  45

Glu Ile Phe Val Ser Lys Lys Leu Lys Asn Arg Lys Val Leu Gln Asp
    50                  55                  60

Ser Asp Ser Glu Thr Glu Asp Thr Asn Ala Ser Pro Glu Lys Thr Thr
65                  70                  75                  80

Tyr Asp Ser Ala Glu Glu Glu Asn Lys Glu Asn Leu Tyr Ala Gly Lys
                85                  90                  95

Asn Thr Lys Ile Lys Arg Ile Tyr Lys Thr Val Ala Asp Ser Asp Glu
            100                 105                 110

Ser Tyr Met Glu Lys Ser Leu Tyr Gln Glu Asn Leu Glu Ala Gln Val
        115                 120                 125

Lys Pro Cys Leu Glu Leu Ser Leu Gln Ser Gly Asn Ser Thr Asp Phe
    130                 135                 140

Thr Thr Asp Arg Lys Ser Ser Lys His Ile His Asp Lys Glu Gly
145                 150                 155                 160

Thr Ala Gly Lys Ala Lys Val Lys Ser Lys Arg Leu Glu Lys Glu
                165                 170                 175
```

Glu Arg Lys Met Glu Lys Ile Arg Gln Leu Lys Lys Lys Glu Thr Lys
            180                 185                 190

Asn Gln Glu Asp Asp Val Glu Gln Pro Phe Asn Asp Ser Gly Cys Leu
        195                 200                 205

Leu Val Asp Lys Asp Leu Phe Glu Thr Gly Leu Glu Asp Glu Asn Asn
    210                 215                 220

Ser Pro Leu Glu Asp Glu Ser Leu Glu Ser Ile Arg Ala Ala Val
225                 230                 235                 240

Lys Asn Lys Val Lys Lys His Lys Lys Lys Glu Pro Ser Leu Glu Ser
                245                 250                 255

Gly Val His Ser Phe Glu Glu Gly Ser Glu Leu Ser Lys Gly Thr Thr
            260                 265                 270

Arg Lys Glu Arg Lys Ala Ala Arg Leu Ser Lys Glu Ala Leu Lys Gln
        275                 280                 285

Leu His Ser Glu Thr Gln Arg Leu Ile Arg Glu Ser Ala Leu Asn Leu
    290                 295                 300

Pro Tyr His Met Pro Glu Asn Lys Thr Ile His Asp Phe Phe Lys Arg
305                 310                 315                 320

Lys Pro Arg Pro Thr Cys His Gly Asn Ala Met Ala Leu Leu Lys Ser
                325                 330                 335

Ser Lys Tyr Gln Ser Ser His His Lys Glu Ile Ile Asp Thr Ala Asn
            340                 345                 350

Thr Thr Glu Met Asn Ser Asp His His Ser Lys Gly Ser Glu Gln Thr
        355                 360                 365

Thr Gly Ala Glu Asn Glu Val Glu Thr Asn Ala Leu Pro Val Val Ser
    370                 375                 380

Lys Glu Thr Gln Ile Ile Thr Gly Ser Asp Glu Ser Cys Arg Lys Asp
385                 390                 395                 400

Leu Val Lys Asn Glu Glu Leu Glu Ile Gln Glu Lys Gln Lys Gln Ser
                405                 410                 415

Asp Ile Arg Pro Ser Pro Gly Asp Ser Ser Val Leu Gln Gln Glu Ser
            420                 425                 430

Asn Phe Leu Gly Asn Asn His Ser Glu Glu Cys Gln Val Gly Gly Leu
        435                 440                 445

Val Ala Phe Glu Pro His Ala Leu Glu Gly Glu Gly Pro Gln Asn Pro
    450                 455                 460

Glu Glu Thr Asp Glu Lys Val Glu Glu Pro Glu Gln Gln Asn Lys Ser
465                 470                 475                 480

Ser Ala Val Gly Pro Pro Glu Lys Val Arg Arg Phe Thr Leu Asp Arg
                485                 490                 495

Leu Lys Gln Leu Gly Val Asp Val Ser Ile Lys Pro Arg Leu Gly Ala
            500                 505                 510

Asp Glu Asp Ser Phe Val Ile Leu Glu Pro Glu Thr Asn Arg Gly Glu
        515                 520                 525

Lys Leu Gln Val Leu Lys Ala Lys Leu Gln Glu Ala Met Lys Leu Arg
    530                 535                 540

Arg Phe Glu Glu Arg Gln Lys Arg Gln Ala Leu Phe Lys Leu Asp Asn
545                 550                 555                 560

Glu Asp Gly Phe Glu Glu Glu Glu Glu Glu Glu Met Thr Asp
                565                 570                 575

Glu Ser Glu Glu Asp Gly Glu Glu Lys Val Lys Glu Glu Lys
            580                 585                 590

-continued

Glu Glu Leu Glu Glu Glu Glu Lys Glu Glu Glu Glu Glu
        595                 600             605

Gly Asn Gln Glu Thr Ala Glu Phe Leu Leu Ser Ser Glu Glu Ile Glu
    610                 615                 620

Thr Lys Asp Glu Lys Glu Met Asp Lys Glu Asn Asn Asp Gly Ser Ser
625                 630                 635                 640

Glu Ile Gly Lys Ala Val Gly Phe Leu Ser Val Pro Lys Ser Leu Ser
                645                 650                 655

Ser Asp Ser Thr Leu Leu Leu Phe Lys Asp Ser Ser Lys Met Gly
            660                 665                 670

Tyr Phe Pro Thr Glu Glu Lys Ser Glu Thr Asp Glu Asn Ser Gly Lys
        675                 680                 685

Gln Pro Ser Lys Leu Asp Glu Asp Ser Cys Ser Leu Leu Thr Lys
    690                 695                 700

Glu Ser Ser His Asn Ser Ser Phe Glu Leu Ile Gly Ser Thr Ile Pro
705                 710                 715                 720

Ser Tyr Gln Pro Cys Asn Arg Gln Thr Gly Arg Gly Thr Ser Phe Phe
                725                 730                 735

Pro Thr Ala Gly Gly Phe Arg Ser Pro Ser Pro Gly Leu Phe Arg Ala
            740                 745                 750

Ser Leu Val Ser Ser Ala Ser Lys Ser Ser Gly Lys Leu Ser Glu Pro
        755                 760                 765

Ser Leu Pro Ile Glu Asp Ser Gln Asp Leu Tyr Asn Ala Ser Pro Glu
    770                 775                 780

Pro Lys Thr Leu Phe Leu Gly Ala Gly Asp Phe Gln Phe Cys Leu Glu
785                 790                 795                 800

Asp Asp Thr Gln Ser Gln Leu Leu Asp Ala Asp Gly Phe Leu Asn Val
                805                 810                 815

Arg Asn His Arg Asn Gln Tyr Gln Ala Leu Lys Pro Arg Leu Pro Leu
            820                 825                 830

Ala Ser Met Asp Glu Asn Ala Met Asp Ala Asn Met Asp Glu Leu Leu
        835                 840                 845

Asp Leu Cys Thr Gly Lys Phe Thr Ser Gln Ala Glu Lys His Leu Pro
    850                 855                 860

Arg Lys Ser Asp Lys Lys Glu Asn Met Glu Glu Leu Leu Asn Leu Cys
865                 870                 875                 880

Ser Gly Lys Phe Thr Ser Gln Asp Ala Ser Thr Pro Ala Ser Ser Glu
                885                 890                 895

Leu Asn Lys Gln Glu Lys Glu Ser Ser Met Gly Asp Pro Met Glu Glu
            900                 905                 910

Ala Leu Ala Leu Cys Ser Gly Ser Phe Pro Thr Asp Lys Glu Glu Glu
        915                 920                 925

Asp Glu Glu Glu Glu Phe Gly Asp Phe Arg Leu Val Ser Asn Asp Asn
    930                 935                 940

Glu Phe Asp Ser Asp Glu Asp Glu His Ser Asp Ser Gly Asn Asp Leu
945                 950                 955                 960

Ala Leu Glu Asp His Glu Asp Asp Glu Glu Glu Leu Leu Lys Arg
                965                 970                 975

Ser Glu Lys Leu Lys Arg Gln Met Arg Leu Arg Lys Tyr Leu Glu Asp
            980                 985                 990

Glu Ala Glu Val Ser Gly Ser Asp  Val Gly Ser Glu Asp  Glu Tyr Asp
        995                 1000                 1005

Gly Glu  Glu Ile Asp Glu Tyr  Glu Glu Asp Val Ile  Asp Glu Val

Leu Pro Ser Asp Glu Glu Leu Gln Ser Gln Ile Lys Lys Ile His
1025                1030                1035

Met Lys Thr Met Leu Asp Asp Lys Arg Gln Leu Arg Leu Tyr
1040                1045                1050

Gln Glu Arg Tyr Leu Ala Asp Gly Asp Leu His Ser Asp Gly Pro
1055                1060                1065

Gly Arg Met Arg Lys Phe Arg Trp Lys Asn Ile Asp Asp Ala Ser
1070                1075                1080

Gln Met Asp Leu Phe His Arg Asp Ser Asp Asp Gln Thr Glu
1085                1090                1095

Glu Gln Leu Asp Glu Ser Glu Ala Arg Trp Arg Lys Glu Arg Ile
1100                1105                1110

Glu Arg Glu Gln Trp Leu Arg Asp Met Ala Gln Gln Gly Lys Ile
1115                1120                1125

Thr Ala Glu Glu Glu Glu Ile Gly Glu Asp Ser Gln Phe Met
1130                1135                1140

Ile Leu Ala Lys Lys Val Thr Ala Lys Ala Leu Gln Lys Asn Ala
1145                1150                1155

Ser Arg Pro Met Val Ile Gln Glu Ser Lys Ser Leu Leu Arg Asn
1160                1165                1170

Pro Phe Glu Ala Ile Arg Pro Gly Ser Ala Gln Gln Val Lys Thr
1175                1180                1185

Gly Ser Leu Leu Asn Gln Pro Lys Ala Val Leu Gln Lys Leu Ala
1190                1195                1200

Ala Leu Ser Asp His Asn Pro Ser Ala Pro Arg Asn Ser Arg Asn
1205                1210                1215

Phe Val Phe His Thr Leu Ser Pro Val Lys Ala Glu Ala Ala Lys
1220                1225                1230

Glu Ser Ser Lys Ser Gln Val Lys Lys Arg Gly Pro Ser Phe Met
1235                1240                1245

Thr Ser Pro Ser Pro Lys His Leu Lys Thr Asp Asp Ser Thr Ser
1250                1255                1260

Gly Leu Thr Arg Ser Ile Phe Lys Tyr Leu Glu Ser
1265                1270                1275

<210> SEQ ID NO 7
<211> LENGTH: 3053
<212> TYPE: DNA
<213> ORGANISM: homo sapiens
<220> FEATURE:
<221> NAME/KEY: misc_feature
<223> OTHER INFORMATION: CDC6 gene

<400> SEQUENCE: 7
gagcgcggct ggagtttgct gctgccgctg tgcagtttgt tcagggcgtt gtggtggtga        60
gtccgagagg ctgcgtgtga gagacgtgag aaggatcctg cactgaggag gtggaaagaa       120
gaggattgct cgaggaggcc tggggtctgt gaggcagcgg agctgggtga aggctgcggg       180
ttccggcgag gctgagctg tgctgtcgtc atgcctcaaa cccgatccca ggcacaggct        240
acaatcagtt ttccaaaaag gaagctgtct cgggcattga acaaagctaa aaactccagt       300
gatgccaaac tagaaccaac aaatgtccaa accgtaacct gttctcctcg tgtaaaagcc       360
ctgcctctca gccccaggaa acgtctgggc gatgacaacc tatgcaacac tcccattta        420 cctccttgtt ctccaccaaa gcaaggcaag aaagagaatg gtccccctca ctcacataca       480

```
cttaagggac gaagattggt atttgacaat cagctgacaa ttaagtctcc tagcaaaaga   540
gaactagcca aagttcacca aaacaaaata ctttcttcag ttagaaaaag tcaagagatc   600
acaacaaatt ctgagcagag atgtccactg aagaaagaat ctgcatgtgt gagactattc   660
aagcaagaag gcacttgcta ccagcaagca aagctggtcc tgaacacagc tgtcccagat   720
cggctgcctg ccagggaaag ggagatggat gtcatcagga atttcttgag ggaacacatc   780
tgtgggaaaa aagctggaag cctttacctt tctggtgctc ctggaactgg aaaaactgcc   840
tgcttaagcc ggattctgca agacctcaag aaggaactga aaggctttaa aactatcatg   900
ctgaattgca tgtccttgag gactgcccag gctgtattcc cagctattgc tcaggagatt   960
tgtcaggaag aggtatccag gccagctggg aaggacatga tgaggaaatt ggaaaaacat  1020
atgactgcag agaagggccc catgattgtg ttggtattgg acgagatgga tcaactggac  1080
agcaaaggcc aggatgtatt gtacacgcta tttgaatggc catggctaag caattctcac  1140
ttggtgctga ttggtattgc taatacccctg gatctcacag atagaattct acctaggctt  1200
caagctagag aaaaatgtaa gccacagctg ttgaacttcc caccttatac cagaaatcag  1260
atagtcacta ttttgcaaga tcgacttaat caggtatcta gagatcaggt tctggacaat  1320
gctgcagttc aattctgtgc ccgcaaagtc tctgctgttt caggagatgt tcgcaaagca  1380
ctggatgttt gcaggagagc tattgaaatt gtagagtcag atgtcaaaag ccagactatt  1440
ctcaaaccac tgtctgaatg taaatcacct tctgagcctc tgattcccaa gagggttggt  1500
cttattcaca tatcccaagt catctcagaa gttgatggta acaggatgac cttgagccaa  1560
gaaggagcac aagattcctt ccctcttcag cagaagatct tggtttgctc tttgatgctc  1620
ttgatcaggc agttgaaaat caaagaggtc actctgggga agttatatga agcctacagt  1680
aaagtctgtc gcaaacagca ggtggcggct gtggaccagt cagagtgttt gtcactttca  1740
gggctcttgg aagccagggg catttttagga ttaaagagaa acaaggaaac ccgtttgaca  1800
aaggtgtttt tcaagattga agagaaagaa atagaacatg ctctgaaaga taaagcttta  1860
attggaaata tcttagctac tggattgcct taaattcttc tcttacaccc cacccgaaag  1920
tattcagctg gcatttagag agctacagtc ttcatttag tgctttacac attcgggcct  1980
gaaaacaaat atgacctttt ttacttgaag ccaatgaatt ttaatctata gattctttaa  2040
tattagcaca gaataatatc tttgggtctt actattttta cccataaaag tgaccaggta  2100
gacccttttt aattacattc actacttcta ccacttgtgt atctctagcc aatgtgcttg  2160
caagtgtaca gatctgtgta gaggaatgtg tgtatattta cctcttcgtt tgctcaaaca  2220
tgagtgggta ttttttttgtt tgtttttttt gttgttgttg ttttgaggc gcgtctcacc  2280 ctgttgccca ggctggagtg caatggcgcg ttctctgctc actacagcac ccgcttccca  2340
ggttgaagtg attctcttgc ctcagcctcc cgagtagctg ggattacagg tgcccaccac  2400
cgcgcccagc taattttta attttagta gagacagggt tttaccatgt tggccaggct  2460
ggtcttgaac tcctgacccct caagtgatct gcccaccttg gcctcctaa gtgctgggat  2520 tataggcgtg agccaccatg ctcagccatt aaggtatttt gttaagaact ttaagtttag  2580
ggtaagaaga atgaaaatga tccagaaaaa tgcaagcaag tccacatgga gatttggagg  2640
acactggtta agaatttat ttctttgtat agtatactat gttcatggtg cagatactac  2700
aacattgtgg catttagac tcgttgagtt tcttgggcac tcccaaggc gttgggtca  2760 taaggagact ataactctac agattgtgaa tatatttatt ttcaagttgc attctttgtc  2820
```

```
ttttttaagca atcagatttc aagagagctc aagctttcag aagtcaatgt gaaaattcct      2880
tcctaggctg tcccacagtc tttgctgccc ttagatgaag ccacttgttt caagatgact      2940
actttggggt tggttttca tctaaacaca ttttccagt cttattagat aaattagtcc        3000
atatggttgg ttaatcaaga gccttctggg tttggtttgg tggcattaaa tgg             3053
```

```
<210> SEQ ID NO 8
<211> LENGTH: 560
<212> TYPE: PRT
<213> ORGANISM: homo sapiens
<220> FEATURE:
<221> NAME/KEY: misc_feature
<223> OTHER INFORMATION: CDC6 protein

<400> SEQUENCE: 8

Met Pro Gln Thr Arg Ser Gln Ala Gln Ala Thr Ile Ser Phe Pro Lys
1               5                   10                  15

Arg Lys Leu Ser Arg Ala Leu Asn Lys Ala Lys Asn Ser Ser Asp Ala
                20                  25                  30

Lys Leu Glu Pro Thr Asn Val Gln Thr Val Thr Cys Ser Pro Arg Val
            35                  40                  45

Lys Ala Leu Pro Leu Ser Pro Arg Lys Arg Leu Gly Asp Asp Asn Leu
        50                  55                  60

Cys Asn Thr Pro His Leu Pro Pro Cys Ser Pro Pro Lys Gln Gly Lys
65                  70                  75                  80

Lys Glu Asn Gly Pro Pro His Ser His Thr Leu Lys Gly Arg Arg Leu
                85                  90                  95

Val Phe Asp Asn Gln Leu Thr Ile Lys Ser Pro Ser Lys Arg Glu Leu
            100                 105                 110

Ala Lys Val His Gln Asn Lys Ile Leu Ser Ser Val Arg Lys Ser Gln
        115                 120                 125

Glu Ile Thr Thr Asn Ser Glu Gln Arg Cys Pro Leu Lys Lys Glu Ser
    130                 135                 140

Ala Cys Val Arg Leu Phe Lys Gln Glu Gly Thr Cys Tyr Gln Gln Ala
145                 150                 155                 160

Lys Leu Val Leu Asn Thr Ala Val Pro Asp Arg Leu Pro Ala Arg Glu
                165                 170                 175

Arg Glu Met Asp Val Ile Arg Asn Phe Leu Arg Glu His Ile Cys Gly
            180                 185                 190

Lys Lys Ala Gly Ser Leu Tyr Leu Ser Gly Ala Pro Gly Thr Gly Lys
        195                 200                 205

Thr Ala Cys Leu Ser Arg Ile Leu Gln Asp Leu Lys Lys Glu Leu Lys
    210                 215                 220

Gly Phe Lys Thr Ile Met Leu Asn Cys Met Ser Leu Arg Thr Ala Gln
225                 230                 235                 240

Ala Val Phe Pro Ala Ile Ala Gln Glu Ile Cys Gln Glu Val Ser
                245                 250                 255

Arg Pro Ala Gly Lys Asp Met Met Arg Lys Leu Glu Lys His Met Thr
            260                 265                 270

Ala Glu Lys Gly Pro Met Ile Val Leu Val Leu Asp Glu Met Asp Gln
        275                 280                 285

Leu Asp Ser Lys Gly Gln Asp Val Leu Tyr Thr Leu Phe Glu Trp Pro
    290                 295                 300

Trp Leu Ser Asn Ser His Leu Val Leu Ile Gly Ile Ala Asn Thr Leu
305                 310                 315                 320
```

Asp Leu Thr Asp Arg Ile Leu Pro Arg Leu Gln Ala Arg Glu Lys Cys
            325                 330                 335

Lys Pro Gln Leu Leu Asn Phe Pro Pro Tyr Thr Arg Asn Gln Ile Val
        340                 345                 350

Thr Ile Leu Gln Asp Arg Leu Asn Gln Val Ser Arg Asp Gln Val Leu
    355                 360                 365

Asp Asn Ala Ala Val Gln Phe Cys Ala Arg Lys Val Ser Ala Val Ser
370                 375                 380

Gly Asp Val Arg Lys Ala Leu Asp Val Cys Arg Ala Ile Glu Ile
385                 390                 395                 400

Val Glu Ser Asp Val Lys Ser Gln Thr Ile Leu Lys Pro Leu Ser Glu
                405                 410                 415

Cys Lys Ser Pro Ser Glu Pro Leu Ile Pro Lys Arg Val Gly Leu Ile
            420                 425                 430

His Ile Ser Gln Val Ile Ser Glu Val Asp Gly Asn Arg Met Thr Leu
        435                 440                 445

Ser Gln Glu Gly Ala Gln Asp Ser Phe Pro Leu Gln Gln Lys Ile Leu
    450                 455                 460

Val Cys Ser Leu Met Leu Leu Ile Arg Gln Leu Lys Ile Lys Glu Val
465                 470                 475                 480

Thr Leu Gly Lys Leu Tyr Glu Ala Tyr Ser Lys Val Cys Arg Lys Gln
                485                 490                 495

Gln Val Ala Ala Val Asp Gln Ser Glu Cys Leu Ser Leu Ser Gly Leu
            500                 505                 510

Leu Glu Ala Arg Gly Ile Leu Gly Leu Lys Arg Asn Lys Glu Thr Arg
        515                 520                 525

Leu Thr Lys Val Phe Phe Lys Ile Glu Glu Lys Glu Ile Glu His Ala
    530                 535                 540

Leu Lys Asp Lys Ala Leu Ile Gly Asn Ile Leu Ala Thr Gly Leu Pro
545                 550                 555                 560

<210> SEQ ID NO 9
<211> LENGTH: 2299
<212> TYPE: DNA
<213> ORGANISM: homo sapiens
<220> FEATURE:
<221> NAME/KEY: misc_feature
<223> OTHER INFORMATION: RAD51 gene

<400> SEQUENCE: 9

```
gttacgtcga cgcgggcgtg accctgggcg agagggtttg cgggaattc  tgaaagccgc    60 tggcggaccg cgcgcagcgg ccagagaccg agccctaagg agagtgcggc gcttcccgag   120
gcgtgcagct gggaactgca actcatctgg gttgtgcgca gaaggctggg gcaagcgagt   180
agagaagtgg agcgtaagcc aggggcgttg ggggccgtgc gggtcgggcg cgtgccacgc   240
ccgcggggtg aagtcggagc gcggggcctg ctggagagag gagcgctgcg gaccgagtaa   300
tggcaatgca gatgcagctt gaagcaaatg cagatacttc agtggaagaa gaaagctttg   360
gcccacaacc catttcacgg ttagagcagt gtggcataaa tgccaacgat gtgaagaaat   420
tggaagaagc tggattccat actgtggagg ctgttgccta tgcgccaaag aaggagctaa   480
taaatattaa gggaattagt gaagccaaag ctgataaaat tctggctgag gcagctaaat   540
tagttccaat gggtttcacc actgcaactg aattccacca aaggcggtca gagatcatac   600
agattactac tggctccaaa gagcttgaca aactacttca aggtggaatt gagactggat   660
ctatcacaga aatgtttgga gaattccgaa ctgggaagac ccagatctgt catacgctag   720
```

```
ctgtcacctg ccagcttccc attgaccggg gtggaggtga aggaaaggcc atgtacattg      780
acactgaggg tacctttagg ccagaacggc tgctggcagt ggctgagagg tatggtctct      840
ctggcagtga tgtcctggat aatgtagcat atgctcgagc gttcaacaca gaccaccaga      900
cccagctcct ttatcaagca tcagccatga tggtagaatc taggtatgca ctgcttattg      960
tagacagtgc caccgccctt tacagaacag actactcggg tcgaggtgag ctttcagcca     1020
ggcagatgca cttggccagg tttctgcgga tgcttctgcg actcgctgat gagtttggtg     1080
tagcagtggt aatcactaat caggtggtag ctcaagtgga tggagcagcg atgtttgctg     1140
ctgatcccaa aaaacctatt ggaggaaata tcatcgccca tgcatcaaca accagattgt     1200
atctgaggaa aggaagaggg gaaaccagaa tctgcaaaat ctacgactct ccctgtcttc     1260
ctgaagctga agctatgttc gccattaatg cagatggagt gggagatgcc aaagactgaa     1320
tcattgggtt tttcctctgt taaaaacctt aagtgctgca gcctaatgag agtgcactgc     1380
tccctggggt tctctacagg cctcttcctg ttgtgactgc caggataaag cttccgggaa     1440
aacagctatt atatcagctt ttctgatggt ataaacagga gacaggtcag tagtcacaaa     1500
ctgatctaaa atgtttattc cttctgtagt gtattaatct ctgtgtgttt tctttggttt     1560
tggaggaggg gtatgaagta tctttgacat ggtgccttag gaatgacttg ggtttaacaa     1620
gctgtctact ggacaatctt atgtttccaa gagaactaaa gctggagaga cctgacccttt    1680 ctctcacttc taaattaatg gtaaaataaa atgcctcagc tatgtagcaa agggaatggg     1740
tctgcacaga ttcttttttt ctgtcagtaa aactctcaag caggttttta agttgtctgt     1800
ctgaatgatc ttgtgtaagg ttttggttat ggagtcttgt gccaaaccta ctaggccatt     1860
agcccttcac catctacctg cttggtcttt cattgctaag actaactcaa gataatccta     1920
gagtcttaaa gcatttcagg ccagtgtggt gtcttgcgcc tgtactccca gcactttggg     1980
aggccgaggc aggtggatcg cttgagccca ggagttttaa gtccagcttg gccaaggtgg     2040
tgaaatccca tctctacaaa aaatgcagaa cttaatctgg acacactgtt acacgtgcct     2100
gtagtcccag ctactcgata gcctgaggtg ggagaatcac ttaagcctgg aaggtggaag     2160
ttgcagtgag tcgagattgc actgctgcat tccagccagg gtgacagagt gagaccatgt     2220
ttcaaacaag aaacatttca gagggtaagt aaacagattt gattgtgagg cttctaataa     2280
agtagttatt agtagtgaa                                                  2299
```

<210> SEQ ID NO 10
<211> LENGTH: 339
<212> TYPE: PRT
<213> ORGANISM: homo sapiens
<220> FEATURE:
<221> NAME/KEY: misc_feature
<223> OTHER INFORMATION: RAD51 protein

<400> SEQUENCE: 10

Met Ala Met Gln Met Gln Leu Glu Ala Asn Ala Asp Thr Ser Val Glu
1               5                   10                  15

Glu Glu Ser Phe Gly Pro Gln Pro Ile Ser Arg Leu Glu Gln Cys Gly
            20                  25                  30

Ile Asn Ala Asn Asp Val Lys Lys Leu Glu Glu Ala Gly Phe His Thr
        35                  40                  45

Val Glu Ala Val Ala Tyr Ala Pro Lys Lys Glu Leu Ile Asn Ile Lys
    50                  55                  60

Gly Ile Ser Glu Ala Lys Ala Asp Lys Ile Leu Ala Glu Ala Ala Lys

```
            65                  70                  75                  80
Leu Val Pro Met Gly Phe Thr Thr Ala Thr Glu Phe His Gln Arg Arg
                85                  90                  95
Ser Glu Ile Ile Gln Ile Thr Thr Gly Ser Lys Glu Leu Asp Lys Leu
            100                 105                 110
Leu Gln Gly Gly Ile Glu Thr Gly Ser Ile Thr Glu Met Phe Gly Glu
            115                 120                 125
Phe Arg Thr Gly Lys Thr Gln Ile Cys His Thr Leu Ala Val Thr Cys
            130                 135                 140
Gln Leu Pro Ile Asp Arg Gly Gly Gly Glu Gly Lys Ala Met Tyr Ile
145                 150                 155                 160
Asp Thr Glu Gly Thr Phe Arg Pro Glu Arg Leu Leu Ala Val Ala Glu
                165                 170                 175
Arg Tyr Gly Leu Ser Gly Ser Asp Val Leu Asp Asn Val Ala Tyr Ala
                180                 185                 190
Arg Ala Phe Asn Thr Asp His Gln Thr Gln Leu Leu Tyr Gln Ala Ser
                195                 200                 205
Ala Met Met Val Glu Ser Arg Tyr Ala Leu Leu Ile Val Asp Ser Ala
210                 215                 220
Thr Ala Leu Tyr Arg Thr Asp Tyr Ser Gly Arg Gly Glu Leu Ser Ala
225                 230                 235                 240
Arg Gln Met His Leu Ala Arg Phe Leu Arg Met Leu Leu Arg Leu Ala
                245                 250                 255
Asp Glu Phe Gly Val Ala Val Val Ile Thr Asn Gln Val Val Ala Gln
                260                 265                 270
Val Asp Gly Ala Ala Met Phe Ala Ala Asp Pro Lys Lys Pro Ile Gly
            275                 280                 285
Gly Asn Ile Ile Ala His Ala Ser Thr Thr Arg Leu Tyr Leu Arg Lys
            290                 295                 300
Gly Arg Gly Glu Thr Arg Ile Cys Lys Ile Tyr Asp Ser Pro Cys Leu
305                 310                 315                 320
Pro Glu Ala Glu Ala Met Phe Ala Ile Asn Ala Asp Gly Val Gly Asp
                325                 330                 335
Ala Lys Asp
```